(12) United States Patent
Or et al.

(10) Patent No.: US 9,220,748 B2
(45) Date of Patent: Dec. 29, 2015

(54) MACROCYCLIC PROLINE DERIVED HCV SERINE PROTEASE INHIBITORS

(71) Applicant: Enanta Pharmaceuticals, Inc., Watertown, MA (US)

(72) Inventors: Yat Sun Or, Watertown, MA (US); Jun Ma, Belmont, MA (US); Guoqiang Wang, Belmont, MA (US); Jiang Long, Wayland, MA (US); Bin Wang, Brighton, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 14/146,161

(22) Filed: Jan. 2, 2014

(65) Prior Publication Data

US 2014/0194350 A1 Jul. 10, 2014

Related U.S. Application Data

(63) Continuation of application No. 13/237,120, filed on Sep. 20, 2011, now Pat. No. 8,648,037.

(60) Provisional application No. 61/385,058, filed on Sep. 21, 2010, provisional application No. 61/499,994, filed on Jun. 22, 2011, provisional application No. 61/504,616, filed on Jul. 5, 2011.

(51) Int. Cl.
| | |
|---|---|
| *A61K 38/12* | (2006.01) |
| *C07K 5/097* | (2006.01) |
| *C07K 5/062* | (2006.01) |
| *C07K 5/083* | (2006.01) |
| *C07K 5/08* | (2006.01) |
| *C07K 14/81* | (2006.01) |

(52) U.S. Cl.
CPC ............. *A61K 38/12* (2013.01); *C07K 5/06034* (2013.01); *C07K 5/0808* (2013.01); *C07K 5/0823* (2013.01); *C07K 5/0827* (2013.01); *C07K 14/811* (2013.01)

(58) Field of Classification Search
None
See application file for complete search history.

(56) References Cited

U.S. PATENT DOCUMENTS

| | | | |
|---|---|---|---|
| 7,368,452 | B2 | 5/2008 | Nakajima et al. |
| 7,582,605 | B2 | 9/2009 | Moore et al. |
| 8,648,037 | B2 | 2/2014 | Or et al. |
| 2004/0106559 | A1 | 6/2004 | Wang et al. |
| 2004/0266668 | A1 | 12/2004 | Nakajima et al. |
| 2007/0021330 | A1 | 1/2007 | Wu et al. |
| 2007/0054842 | A1 | 3/2007 | Blatt et al. |
| 2007/0060510 | A1 | 3/2007 | Nakajima et al. |
| 2007/0299078 | A1 | 12/2007 | Niu et al. |
| 2008/0008681 | A1 | 1/2008 | Niu et al. |
| 2008/0032936 | A1 | 2/2008 | Gai et al. |
| 2008/0039375 | A1 | 2/2008 | Moore et al. |
| 2008/0267916 | A1 | 10/2008 | Gai et al. |
| 2008/0267917 | A1 | 10/2008 | Niu et al. |
| 2008/0287449 | A1 | 11/2008 | Niu et al. |
| 2009/0075869 | A1 | 3/2009 | Holloway et al. |
| 2009/0123425 | A1 | 5/2009 | Moore et al. |

(Continued)

FOREIGN PATENT DOCUMENTS

| | | |
|---|---|---|
| WO | 0177113 A2 | 10/2001 |
| WO | 03099274 A1 | 12/2003 |

(Continued)

OTHER PUBLICATIONS

Ettmayer P. et al. J. Med. Chem. (2004) 47(10), pp. 2393-2404.*

(Continued)

*Primary Examiner* — Thomas S Heard
(74) *Attorney, Agent, or Firm* — Edgar W. Harlan; Carolyn S. Elmore, Esq.; Elmore Patent Law Group, P.C.

(57) ABSTRACT

The present invention discloses compounds of Formula I or pharmaceutically acceptable salts, esters, or prodrugs thereof:

(I)

which inhibit serine protease activity, particularly the activity of hepatitis C virus (HCV) NS3-NS4A protease. Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

15 Claims, No Drawings

(56) References Cited

U.S. PATENT DOCUMENTS

| | | |
|---|---|---|
| 2009/0142299 A1 | 6/2009 | Sun et al. |
| 2009/0180981 A1 | 7/2009 | Niu et al. |
| 2009/0180984 A1 | 7/2009 | Sun et al. |
| 2009/0180985 A1 | 7/2009 | Liu et al. |
| 2009/0191151 A1 | 7/2009 | Gai et al. |
| 2009/0197888 A1 | 8/2009 | Gai et al. |
| 2009/0238794 A1 | 9/2009 | Gai et al. |
| 2009/0274657 A1 | 11/2009 | Gai et al. |
| 2010/0003214 A1 | 1/2010 | Gai et al. |
| 2010/0029666 A1 | 2/2010 | Harper et al. |
| 2011/0033420 A1 | 2/2011 | Gai et al. |
| 2011/0123496 A1 | 5/2011 | Gai et al. |

FOREIGN PATENT DOCUMENTS

| | | |
|---|---|---|
| WO | 2006119061 A2 | 11/2006 |
| WO | 2007015787 A1 | 2/2007 |
| WO | 2007015855 A1 | 2/2007 |
| WO | 2007016441 A1 | 2/2007 |
| WO | 2007131966 A1 | 11/2007 |
| WO | 2007148135 A1 | 12/2007 |
| WO | 2008051475 A2 | 5/2008 |
| WO | 2008051477 A2 | 5/2008 |
| WO | 2008051514 A2 | 5/2008 |
| WO | 2008057208 A2 | 5/2008 |
| WO | 2008057209 A1 | 5/2008 |
| WO | 2009010804 A1 | 1/2009 |
| WO | 2009064975 A1 | 5/2009 |
| WO | 2009108507 A1 | 9/2009 |
| WO | 2009134624 A1 | 11/2009 |
| WO | 2011014487 A1 | 2/2011 |
| WO | 2012040040 A1 | 3/2012 |

OTHER PUBLICATIONS

Singh, Yashveer et al, "Recent Trends in Targeted Anticancer Prodrug and Conjugate," DesignCurr Med Chem. 2008; 15(18): 1802-1826.*

Muller, Christa E. "Prodrug Approaches for Enhancing the Bioavailability of Drugs with Low Solubility," Chemistry & Biodiversity, vol. 6 (2009), pp. 2071-2083.*

Beaumont, et, al "Design of Ester Prodrugs to Enhance Oral Absorption of Poorly Permeable Compounds: Challenges to the Discovery Scientist," Current Drug Metabolism, 2003, 4, 461-485.*

Han, H.-K.. AAPS Pharmsci. (2000) 2(1), Article 6, pp. 1-11.*

Testa Prodrug research: futile or fertile? Biochemical Pharmacology (2004) 2097-2106.*

Liverton, et al., "Moecuar Modeling Based Appoach to Poten P2-P4 Macocyclic Inhibitors of Hepatts C NS3/4A Protease," J. American Chem. Soc., 2008, 130(14) pp. 4607-4609.

International Search Report for PCT/US11/52304, dated Jan. 31, 2012.

* cited by examiner

MACROCYCLIC PROLINE DERIVED HCV SERINE PROTEASE INHIBITORS

RELATED APPLICATIONS

This application is a continuation application of U.S. application Ser. No. 13/237,120, filed on Sep. 20, 2011, which claims the benefit of U.S. Provisional Application No. 61/385,058, filed on Sep. 21, 2010, U.S. Provisional Application No. 61/499,994, filed on Jun. 22, 2011, and U.S. Provisional Application No. 61/504,616, filed on Jul. 5, 2011. The entire teachings of the above applications are incorporated herein by reference.

JOINT RESEARCH AGREEMENT

Inventions described in this application were made by or on behalf of Enanta Pharmaceuticals, Inc. and Abbott Laboratories who are parties to a joint research agreement, that was in effect on or before the date such inventions were made and such inventions were made as a result of activities undertaken within the scope of the joint research agreement.

TECHNICAL FIELD

The present invention relates to novel hepatitis C virus (HCV) protease inhibitor compounds, methods for using the same to treat HCV infection, as well as processes for making such compounds.

BACKGROUND OF THE INVENTION

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantations in the western world.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

Only two approved therapies for HCV infection are currently available. The original treatment regimen generally involves a 3-12 month course of intravenous interferon-α (IFN-α), while a new approved second-generation treatment involves co-treatment with IFN-α and the general antiviral nucleoside mimics like ribavirin. Both of these treatments suffer from interferon related side effects as well as low efficacy against HCV infections. There exists a need for the development of effective antiviral agents for treatment of HCV infection due to the poor tolerability and disappointing efficacy of existing therapies.

In a patient population where the majority of individuals are chronically infected and asymptomatic and the prognoses are unknown, an effective drug would desirably possess significantly fewer side effects than the currently available treatments. The hepatitis C non-structural protein-3 (NS3) is a proteolytic enzyme required for processing of the viral polyprotein and consequently viral replication. Despite the huge number of viral variants associated with HCV infection, the active site of the NS3 protease remains highly conserved thus making its inhibition an attractive mode of intervention. Recent success in the treatment of HIV with protease inhibitors supports the concept that the inhibition of NS3 is a key target in the battle against HCV.

HCV is a flaviridae type RNA virus. The HCV genome is enveloped and contains a single strand RNA molecule composed of circa 9600 base pairs. It encodes a polypeptide comprised of approximately 3010 amino acids.

The HCV polyprotein is processed by viral and host peptidase into 10 discreet peptides which serve a variety of functions. There are three structural proteins, C, E1 and E2. The P7 protein is of unknown function and is comprised of a highly variable sequence. There are six non-structural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease.

The NS3/4A protease is responsible for cleaving four sites on the viral polyprotein. The NS3-NS4A cleavage is autocatalytic, occurring in cis. The remaining three hydrolyses, NS4A-NS4B, NS4B-NS5A and NS5A-NS5B all occur in trans. NS3 is a serine protease which is structurally classified as a chymotrypsin-like protease. While the NS serine protease possesses proteolytic activity by itself, the HCV protease enzyme is not an efficient enzyme in terms of catalyzing polyprotein cleavage. It has been shown that a central hydrophobic region of the NS4A protein is required for this enhancement. The complex formation of the NS3 protein with NS4A seems necessary to the processing events, enhancing the proteolytic efficacy at all of the sites.

A general strategy for the development of antiviral agents is to inactivate virally encoded enzymes, including NS3, that are essential for the replication of the virus. Current efforts directed toward the discovery of NS3 protease inhibitors were reviewed by S. Tan, A. Pause, Y. Shi, N. Sonenberg, Hepatitis C Therapeutics: Current Status and Emerging Strategies, *Nature Rev. Drug Discov.* 1, 867-881 (2002).

SUMMARY OF THE INVENTION

In one aspect, the invention provides compounds represented by Formula I, or pharmaceutically acceptable salts, esters, or prodrugs thereof:

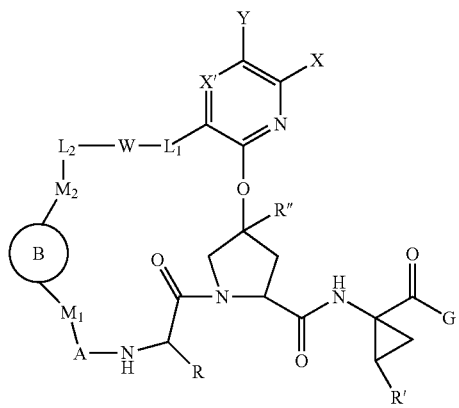

(I)

wherein

A is absent, —(C=O)—, —S(O)₂-, —C(=N—OR₁)— or —C(=N—CN)—;

Ⓑ is selected from —C₃-C₁₂ cycloalkyl, substituted —C₃-C₁₂ cycloalkyl; —C₃-C₁₂ cycloalkenyl, substituted —C₃-C₁₂ cycloalkenyl; —C₃-C₁₂ heterocycloalkyl, and substituted —C₃-C₁₂ heterocycloalkyl;

or Ⓑ is

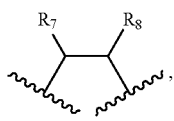

wherein $R_7$ and $R_8$ are each independently $C_1$-$C_8$ alkyl or $C_2$-$C_8$ alkenyl and are each independently optionally substituted with one or more halo;

$M_1$ and $M_2$ are each independently selected from O and $NR_1$;

each $R_1$ is independently selected at each occurrence from the group consisting of:
(i) hydrogen;
(ii) aryl; substituted aryl; heteroaryl; substituted heteroaryl;
(iii) heterocycloalkyl; substituted heterocycloalkyl; and
(iv) —C₁-C₈ alkyl, —C₂-C₈ alkenyl, or —C₂-C₈ alkynyl each containing 0, 1, 2, or 3 heteroatoms selected from O, S, or N; substituted —C₁-C₈ alkyl, substituted —C₂-C₈ alkenyl, or substituted —C₂-C₈ alkynyl each containing 0, 1, 2, or 3 heteroatoms selected from O, S or N; —C₃-C₁₂ cycloalkyl, substituted —C₃-C₁₂ cycloalkyl; —C₃-C₁₂ cycloalkenyl, or substituted —C₃-C₁₂ cycloalkenyl;

$L_1$ and $L_2$ are each independently selected from —C₁-C₈ alkylene, —C₂-C₈ alkenylene, or —C₂-C₈ alkynylene each containing 0, 1, 2, or 3 heteroatoms selected from O, S, or N; substituted —C₁-C₈ alkylene, substituted —C₂-C₈ alkenylene, or substituted —C₂-C₈ alkynylene each containing 0, 1, 2, or 3 heteroatoms selected from O, S or N; —C₃-C₁₂ cycloalkylene, or substituted —C₃-C₁₂ cycloalkylene each containing 0, 1, 2, or 3 heteroatoms selected from O, S or N; —C₃-C₁₂ cycloalkenylene, or substituted —C₃-C₁₂ cycloalkenylene each containing 0, 1, 2, or 3 heteroatoms selected from O, S or N;

W is absent, —O—, —S—, —NH—, —N(Me)-, —C(O)NH—, or —C(O)N(Me)-;

X and Y, taken together with the carbon atoms to which they are attached, form a cyclic moiety selected from aryl, substituted aryl, heteroaryl, substituted heteroaryl, heterocyclic, substituted heterocylic, carbocyclic and substituted carbocyclic;

X' is N or —C($R_2$)—, where $R_2$ is selected from the group consisting of:
(i) hydrogen, halogen, CN, CF₃, NO₂, OR₃, SR₃, —NHS(O)₂—R₃, —NH(SO₂)NR₄R₅, NR₄R₅, CO₂R₃, COR₃, CONR₄R₅, N(R₁)COR₃; aryl; substituted aryl; heteroaryl; or substituted heteroaryl;
(ii) heterocycloalkyl or substituted heterocycloalkyl; and
(iii) —C₁-C₈ alkyl, —C₂-C₈ alkenyl, or —C₂-C₈ alkynyl each containing 0, 1, 2, or 3 heteroatoms selected from O, S, or N; substituted —C₁-C₈ alkyl, substituted —C₂-C₈ alkenyl, or substituted —C₂-C₈ alkynyl each containing 0, 1, 2, or 3 heteroatoms selected from O, S or N; —C₃-C₁₂ cycloalkyl, substituted —C₃-C₁₂ cycloalkyl; —C₃-C₁₂ cycloalkenyl, or substituted —C₃-C₁₂ cycloalkenyl;

each $R_3$ is independently selected from $C_1$-$C_8$ alkyl, —C₂-C₈ alkenyl, or —C₂-C₈ alkynyl each containing 0, 1, 2, or 3 heteroatoms selected from O, S or N, substituted —C₁-C₈ alkyl, substituted —C₂-C₈ alkenyl, or substituted —C₂-C₈ alkynyl each containing 0, 1, 2, or 3 heteroatoms selected from O, S or N; and —C₃-C₁₂ cycloalkyl, substituted —C₃-C₁₂ cycloalkyl; —C₃-C₁₂ cycloalkenyl, or substituted —C₃-C₁₂ cycloalkenyl; heterocylic; substituted heterocyclic; aryl; substituted aryl; heteroaryl; or substituted heteroaryl;

each $R_4$ and $R_5$ are independently selected from H and $R_3$, or $R_4$ and $R_5$ together with the nitrogen atom to which they are attached form a heterocyclic ring;

R and R' are each independently selected from the group consisting of:
(i) —C₁-C₈ alkyl, —C₂-C₈ alkenyl, or —C₂-C₈ alkynyl each containing 0, 1, 2, or 3 heteroatoms selected from O, S, or N; substituted —C₁-C₈ alkyl, substituted —C₂-C₈ alkenyl, or substituted —C₂-C₈ alkynyl each containing 0, 1, 2, or 3 heteroatoms selected from O, S or N; —C₃-C₁₂ cycloalkyl, substituted —C₃-C₁₂ cycloalkyl; —C₄-C₁₂ alkylcycloalkyl, substituted —C₄-C₁₂ alkylcycloalkyl; —C₃-C₁₂ cycloalkenyl, substituted —C₃-C₁₂ cycloalkenyl; —C₄-C₁₂ alkylcycloalkenyl, or substituted —C₄-C₁₂ alkylcycloalkenyl;
(ii) aryl; substituted aryl; heteroaryl; substituted heteroaryl;
(iii) heterocycloalkyl or substituted heterocycloalkyl; and
(iv) hydrogen or deuterium;

G is selected from —OH, —NHS(O)₂—R₃, —NH(SO₂)NR₄R₅, and NR₄R₅; and

R" is selected from hydrogen, methyl, ethyl, and allyl.

In one embodiment, Ⓑ is selected from —C₃-C₁₂ cycloalkyl, substituted —C₃-C₁₂ cycloalkyl; —C₃-C₁₂ cycloalkenyl, substituted —C₃-C₁₂ cycloalkenyl; —C₃-C₁₂ heterocycloalkyl, and substituted —C₃-C₁₂ heterocycloalkyl.

In one embodiment of the invention, Ⓑ is selected from, but not limited to, the group of rings consisting of:

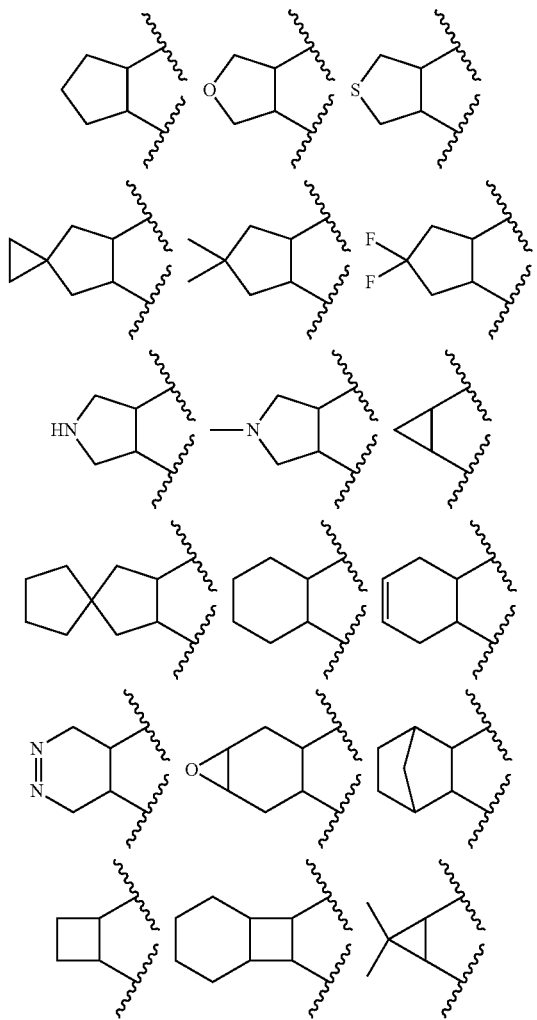

Preferably, X and Y, taken together with the carbon atoms to which they are attached, form a cyclic moiety selected from aryl, substituted aryl, heteroaryl, substituted heteroaryl, heterocyclic and substituted heterocyclic, more preferably aryl, substituted aryl, heteroaryl or substituted heteroaryl. Most preferably, X and Y, taken together with the carbon atoms to which they are attached, form a benzo or substituted benzo ring.

In another embodiment, the present invention features pharmaceutical compositions comprising a compound of the invention (e.g., Formula I), or a pharmaceutically acceptable salt, ester or prodrug thereof. In still another embodiment of the present invention there are disclosed pharmaceutical compositions comprising a therapeutically effective amount of a compound of the invention (e.g., Formula I), or a pharmaceutically acceptable salt, ester or prodrug thereof, in combination with a pharmaceutically acceptable carrier or excipient. In yet another embodiment of the invention are methods of treating a hepatitis C infection in a subject in need of such treatment with said compound of the invention (e.g., Formula I), or said pharmaceutical compositions.

Other features, objects, and advantages of the present invention are apparent in the detailed description that follows.

It should be understood, however, that the detailed description, while indicating preferred embodiments of the invention, are given by way of illustration only, not limitation. Various changes and modifications within the scope of the invention will become apparent to those skilled in the art from the detailed description.

DETAILED DESCRIPTION OF THE INVENTION

A first embodiment of the invention is a compound represented by Formula I as described above, or a pharmaceutically acceptable salt, ester or prodrug thereof, alone or in combination with a pharmaceutically acceptable carrier or excipient.

Another embodiment of the invention is a compound represented by Formula II:

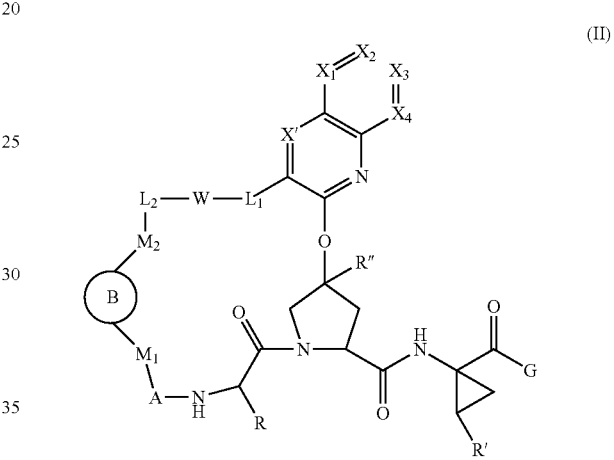

(II)

or a pharmaceutically acceptable salt, ester or prodrug thereof, alone or in combination with a pharmaceutically acceptable carrier or excipient, where $X_1$-$X_4$ are independently selected from —$CR_6$ and N, wherein each $R_6$ is independently selected from:

(i) hydrogen; halogen; —$NO_2$; —CN; or $N_3$;

(ii) -M-$R_3$, wherein M is O, S, or NH;

(iii) $NR_4R_5$;

(iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;

(v) aryl; substituted aryl; heteroaryl; or substituted heteroaryl; and (vi) heterocycloalkyl or substituted heterocycloalkyl;

A is absent, —(C═O)—, —S(O)$_2$-, —C(═N—$OR_1$)— or —C(═N—CN)—;

Ⓑ is selected from —$C_3$-$C_{12}$ cycloalkyl, substituted —$C_3$-$C_{12}$ cycloalkyl; —$C_3$-$C_{12}$ cycloalkenyl, substituted —$C_3$-$C_{12}$ cycloalkenyl; —$C_3$-$C_{12}$ heterocycloalkyl, and substituted —$C_3$-$C_{12}$ heterocycloalkyl;

or ⓑ is

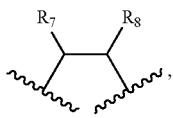

wherein $R_7$ and $R_8$ are each independently $C_1$-$C_8$ alkyl or $C_2$-$C_8$ alkenyl and are each independently optionally substituted with one or more halo;

$M_1$ and $M_2$ are each independently selected from O and $NR_1$;

each $R_1$ is independently selected at each occurrence from the group consisting of:
(i) hydrogen;
(ii) aryl; substituted aryl; heteroaryl; or substituted heteroaryl;
(iii) heterocycloalkyl or substituted heterocycloalkyl; and
(iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;

$L_1$ and $L_2$ are each independently selected from —$C_1$-$C_8$ alkylene, —$C_2$-$C_8$ alkenylene, or —$C_2$-$C_8$ alkynylene each containing 0, 1, 2, or 3 heteroatoms selected from O, S, or N; substituted —$C_1$-$C_8$ alkylene, substituted —$C_2$-$C_8$ alkenylene, or substituted —$C_2$-$C_8$ alkynylene each containing 0, 1, 2, or 3 heteroatoms selected from O, S or N; —$C_3$-$C_{12}$ cycloalkylene, or substituted —$C_3$-$C_{12}$ cycloalkylene each containing 0, 1, 2, or 3 heteroatoms selected from O, S or N; —$C_3$-$C_{12}$ cycloalkenylene or substituted —$C_3$-$C_{12}$ cycloalkenylene each containing 0, 1, 2, or 3 heteroatoms selected from O, S or N;

W is absent, —O—, —S—, —NH—, —N(Me)-, —C(O)NH—, or —C(O)N(Me)-;

X' is N or —C($R_2$)—, where $R_2$ is selected from the group consisting of:
(i) hydrogen, halogen, CN, $CF_3$, $NO_2$, $OR_3$, $SR_3$, —NHS(O)$_2$—$R_3$, —NH(SO$_2$)NR$_4$R$_5$, NR$_4$R$_5$, CO$_2$R$_3$, COR$_3$, CONR$_4$R$_5$, N(R$_1$)COR$_3$; aryl; substituted aryl; heteroaryl; or substituted heteroaryl;
(ii) heterocycloalkyl or substituted heterocycloalkyl; and
(iii) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

each $R_3$ is independently selected from $C_1$-$C_8$ alkyl, —$C_2$-$C_8$ alkenyl, or —$C_2$-$C_8$ alkynyl each containing 0, 1, 2, or 3 heteroatoms selected from O, S or N, substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_3$-$C_{12}$ cycloalkenyl, substituted —$C_3$-$C_{12}$ cycloalkenyl; heterocyclic; substituted heterocyclic; aryl; substituted aryl; heteroaryl; and substituted heteroaryl;

each $R_4$ and $R_5$ are independently selected from H and $R_3$, or $R_4$ and $R_5$ combined together with the N they are attached to form a heterocyclic ring;

R and R' are each independently selected from the group consisting of:
(i) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_4$-$C_{12}$ alkylcycloalkyl, substituted —$C_4$-$C_{12}$ alkylcycloalkyl; —$C_3$-$C_{12}$ cycloalkenyl, substituted —$C_3$-$C_{12}$ cycloalkenyl; —$C_4$-$C_{12}$ alkylcycloalkenyl, or substituted —$C_4$-$C_{12}$ alkylcycloalkenyl;
(ii) aryl; substituted aryl; heteroaryl; substituted heteroaryl;
(iii) heterocycloalkyl or substituted heterocycloalkyl; and
(iv) hydrogen; deuterium;

G is selected from —OH, —NHS(O)$_2$—$R_3$, —NH(SO$_2$)NR$_4$R$_5$, and NR$_4$R$_5$; and R" is selected from hydrogen, methyl, ethyl, and allyl.

Another embodiment of the invention is a compound represented by Formula III or IV:

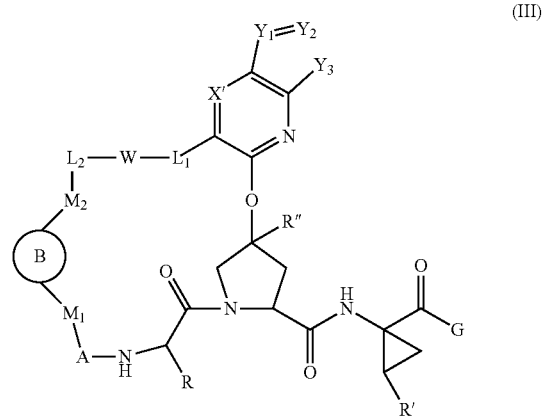

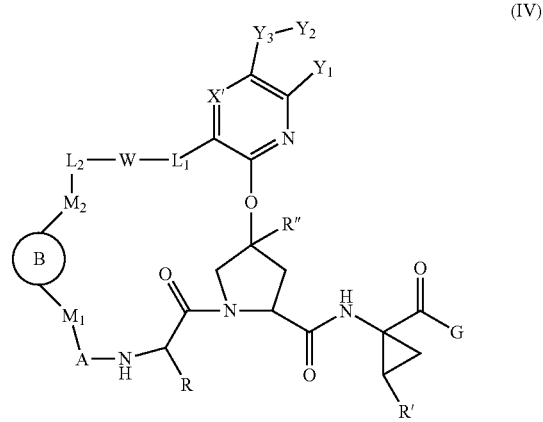

or a pharmaceutically acceptable salt, ester or prodrug thereof, alone or in combination with a pharmaceutically acceptable carrier or excipient, where each $Y_1$ and $Y_2$ are independently selected from $CR_6$ and N, and each $Y_3$ is independently selected from $NR_6$, S and O;

each $R_6$ is independently selected from:
(i) hydrogen; halogen; —$NO_2$; —CN; or $N_3$;
(ii) -M-$R_3$, wherein M is O, S, or NH;
(iii) $NR_4R_5$;
(iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;
(v) aryl; substituted aryl; heteroaryl; or substituted heteroaryl; and
(vi) heterocycloalkyl or substituted heterocycloalkyl;
A is absent, —(C=O)—, —$S(O)_2$-, —C(=N—$OR_1$)— or —C(=N—CN)—;
Ⓑ is selected from —$C_3$-$C_{12}$ cycloalkyl, substituted —$C_3$-$C_{12}$ cycloalkyl; —$C_3$-$C_{12}$ cycloalkenyl, substituted —$C_3$-$C_{12}$ cycloalkenyl; —$C_3$-$C_{12}$ heterocycloalkyl, and substituted —$C_3$-$C_{12}$ heterocycloalkyl;
or Ⓑ is

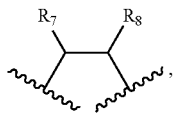

wherein $R_7$ and $R_8$ are each independently $C_1$-$C_8$ alkyl or $C_2$-$C_8$ alkenyl and are each independently optionally substituted with one or more halo;
$M_1$ and $M_2$ are each independently selected from O and $NR_1$;
each $R_1$ is independently selected at each occurrence from the group consisting of:
(i) hydrogen;
(ii) aryl; substituted aryl; heteroaryl; or substituted heteroaryl;
(iii) heterocycloalkyl or substituted heterocycloalkyl; and
(iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;
$L_1$ and $L_2$ are each independently selected from —$C_1$-$C_8$ alkylene, —$C_2$-$C_8$ alkenylene, or —$C_2$-$C_8$ alkynylene each containing 0, 1, 2, or 3 heteroatoms selected from O, S, or N; substituted —$C_1$-$C_8$ alkylene, substituted —$C_2$-$C_8$ alkenylene, or substituted —$C_2$-$C_8$ alkynylene each containing 0, 1, 2, or 3 heteroatoms selected from O, S or N; —$C_3$-$C_{12}$ cycloalkylene, or substituted —$C_3$-$C_{12}$ cycloalkylene each containing 0, 1, 2, or 3 heteroatoms selected from O, S or N; —$C_3$-$C_{12}$ cycloalkenylene, or substituted —$C_3$-$C_{12}$ cycloalkenylene each containing 0, 1, 2, or 3 heteroatoms selected from O, S or N;
W is absent, —O—, —S—, —NH—, —N(Me)-, —C(O)NH—, or —C(O)N(Me)-;
X' is N or —C($R_2$)—, where $R_2$ is selected from the group consisting of:
(i) hydrogen, halogen, CN, $CF_3$, $NO_2$, $OR_3$, $SR_3$, —$NHS(O)_2$—$R_3$, —$NH(SO_2)NR_4R_5$, $NR_4R_5$, $CO_2R_3$, $COR_3$, $CONR_4R_5$, $N(R_1)COR_3$; aryl; substituted aryl; heteroaryl; or substituted heteroaryl;

(ii) heterocycloalkyl or substituted heterocycloalkyl; and
(iii) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;
each $R_3$ is independently selected from $C_1$-$C_8$ alkyl, —$C_2$-$C_8$ alkenyl, or —$C_2$-$C_8$ alkynyl each containing 0, 1, 2, or 3 heteroatoms selected from O, S or N, substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_3$-$C_{12}$ cycloalkenyl, substituted —$C_3$-$C_{12}$ cycloalkenyl; heterocyclic; substituted heterocyclic; aryl; substituted aryl; heteroaryl; and substituted heteroaryl;
each $R_4$ and $R_5$ are independently selected from H and $R_3$, or $R_4$ and $R_5$ combined together with the N they are attached to form a heterocyclic ring;
R and R' are each independently selected from the group consisting of:
(i) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_4$-$C_{12}$ alkylcycloalkyl, substituted —$C_4$-$C_{12}$ alkylcycloalkyl; —$C_3$-$C_{12}$ cycloalkenyl, substituted —$C_3$-$C_{12}$ cycloalkenyl; —$C_4$-$C_{12}$ alkylcycloalkenyl, or substituted —$C_4$-$C_{12}$ alkylcycloalkenyl;
(ii) aryl; substituted aryl; heteroaryl; or substituted heteroaryl;
(iii) heterocycloalkyl or substituted heterocycloalkyl; and
(iv) hydrogen or deuterium;
G is selected from —OH, —$NHS(O)_2$—$R_3$, —$NH(SO_2)NR_4R_5$, and $NR_4R_5$; and
R" is selected from hydrogen, methyl, ethyl, and allyl.
Another embodiment of the invention is a compound represented by Formula V:

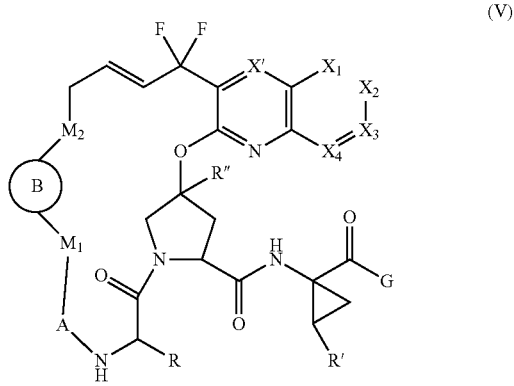

or a pharmaceutically acceptable salt, ester or prodrug thereof, alone or in combination with a pharmaceutically acceptable carrier or excipient, wherein $X_1$-$X_4$ are independently selected from —$CR_6$ and N, wherein each $R_6$ is independently selected from:
(i) hydrogen; halogen; —$NO_2$; —CN; or $N_3$;
(ii) -M-$R_3$, where M is O, S, or NH;
(iii) $NR_4R_5$;
(iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;
(v) aryl; substituted aryl; heteroaryl; or substituted heteroaryl; and
(vi) heterocycloalkyl or substituted heterocycloalkyl;
A is absent, —(C=O)—, —S(O)$_2$-, —C(=N—O$R_1$)— or —C(=N—CN)—;
Ⓑ is selected from —$C_3$-$C_{12}$ cycloalkyl, substituted —$C_3$-$C_{12}$ cycloalkyl; —$C_3$-$C_{12}$ cycloalkenyl, substituted —$C_3$-$C_{12}$ cycloalkenyl; —$C_3$-$C_{12}$ heterocycloalkyl, and substituted —$C_3$-$C_{12}$ heterocycloalkyl;
or Ⓑ is

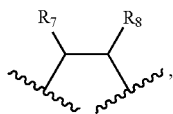

wherein $R_7$ and $R_8$ are each independently $C_1$-$C_8$ alkyl or $C_2$-$C_8$ alkenyl and are each independently optionally substituted with one or more halo;
$M_1$ and $M_2$ are each independently selected from O and $NR_1$;
each $R_1$ is independently selected at each occurrence from the group consisting of:
(i) hydrogen;
(ii) aryl; substituted aryl; heteroaryl; or substituted heteroaryl;
(iii) heterocycloalkyl or substituted heterocycloalkyl; and
(iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;
X' is N or —C($R_2$)—, where $R_2$ is selected from the group consisting of:
(i) hydrogen, halogen, CN, $CF_3$, $NO_2$, $OR_3$, $SR_3$, —NHS(O)$_2$—$R_3$, —NH(SO$_2$)$NR_4R_5$, $NR_4R_5$, $CO_2R_3$, $COR_3$, $CONR_4R_5$, $N(R_1)COR_3$; aryl; substituted aryl; heteroaryl; or substituted heteroaryl;
(ii) heterocycloalkyl or substituted heterocycloalkyl; and
(iii) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;

each $R_3$ is independently selected from $C_1$-$C_8$ alkyl, —$C_2$-$C_8$ alkenyl, or —$C_2$-$C_8$ alkynyl each containing 0, 1, 2, or 3 heteroatoms selected from O, S or N, substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_3$-$C_{12}$ cycloalkenyl, substituted —$C_3$-$C_{12}$ cycloalkenyl; heterocylic; substituted heterocyclic; aryl; substituted aryl; heteroaryl; and substituted heteroaryl;
each $R_4$ and $R_5$ are independently selected from H and $R_3$, or $R_4$ and $R_5$ combined together with the N they are attached to form a heterocyclic ring;
R and R' are each independently selected from the group consisting of:
(i) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_4$-$C_{12}$ alkylcycloalkyl, substituted —$C_4$-$C_{12}$ alkylcycloalkyl; —$C_3$-$C_{12}$ cycloalkenyl, substituted —$C_3$-$C_{12}$ cycloalkenyl; —$C_4$-$C_{12}$ alkylcycloalkenyl, or substituted —$C_4$-$C_{12}$ alkylcycloalkenyl;
(ii) aryl; substituted aryl; heteroaryl; or substituted heteroaryl;
(iii) heterocycloalkyl or substituted heterocycloalkyl; and
(iv) hydrogen; or deuterium;
G is selected from —OH, —NHS(O)$_2$—$R_3$, —NH(SO$_2$) $NR_4R_5$, and $NR_4R_5$; and
R" is selected from hydrogen, methyl, ethyl, and allyl.
Another embodiment of the invention is a compound represented by Formula VI:

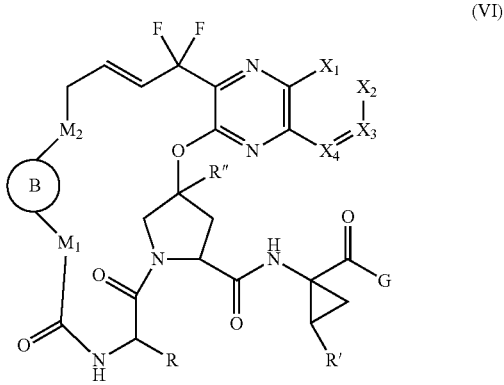

(VI)

or a pharmaceutically acceptable salt, ester or prodrug thereof, alone or in combination with a pharmaceutically acceptable carrier or excipient, wherein
$X_1$-$X_4$ are independently selected from —$CR_6$ and N, wherein each $R_6$ is independently selected from:
(i) hydrogen; halogen; —$NO_2$; —CN; or $N_3$;
(ii) -M-$R_3$, wherein M is O, S, or NH;
(iii) $NR_4R_5$;
(iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;
(v) aryl; substituted aryl; heteroaryl; or substituted heteroaryl; and
(vi) heterocycloalkyl or substituted heterocycloalkyl;
Ⓑ is selected from —$C_3$-$C_{12}$ cycloalkyl, substituted —$C_3$-$C_{12}$ cycloalkyl; —$C_3$-$C_{12}$ cycloalkenyl, substituted —$C_3$-$C_{12}$ cycloalkenyl; —$C_3$-$C_{12}$ heterocycloalkyl, and substituted —$C_3$-$C_{12}$ heterocycloalkyl;
or Ⓑ is

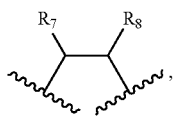

wherein $R_7$ and $R_8$ are each independently $C_1$-$C_8$ alkyl or $C_2$-$C_8$ alkenyl and are each independently optionally substituted with one or more halo;
$M_1$ and $M_2$ are each independently selected from O and $NR_1$;
each $R_1$ is independently selected at each occurrence from the group consisting of:
(i) hydrogen;
(ii) aryl; substituted aryl; heteroaryl; or substituted heteroaryl;
(iii) heterocycloalkyl or substituted heterocycloalkyl; and
(iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;
each $R_3$ is independently selected from $C_1$-$C_8$ alkyl, —$C_2$-$C_8$ alkenyl, or —$C_2$-$C_8$ alkynyl each containing 0, 1, 2, or 3 heteroatoms selected from O, S or N, substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_3$-$C_{12}$ cycloalkenyl, substituted —$C_3$-$C_{12}$ cycloalkenyl; heterocylic; substituted heterocyclic; aryl; substituted aryl; heteroaryl; and substituted heteroaryl;
each $R_4$ and $R_5$ are independently selected from H and $R_3$, or $R_4$ and $R_5$ combined together with the N they are attached to form a heterocyclic ring;
R and R' are each independently selected from the group consisting of:
(i) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_4$-$C_{12}$ alkylcycloalkyl, substituted —$C_4$-$C_{12}$ alkylcycloalkyl; —$C_3$-$C_{12}$ cycloalkenyl, substituted —$C_3$-$C_{12}$ cycloalkenyl; —$C_4$-$C_{12}$ alkylcycloalkenyl, or substituted —$C_4$-$C_{12}$ alkylcycloalkenyl;

(ii) aryl; substituted aryl; heteroaryl; or substituted heteroaryl;
(iii) heterocycloalkyl or substituted heterocycloalkyl; and
(iv) hydrogen; or deuterium;
G is selected from —OH, —NHS(O)$_2$—$R_3$, —NH(SO$_2$)NR$_4$R$_5$, and NR$_4$R$_5$; and
R" is selected from hydrogen, methyl, ethyl, and allyl.
The present invention also features compounds of Formula VII and pharmaceutically acceptable salts, esters, and prodrugs thereof:

(VII)

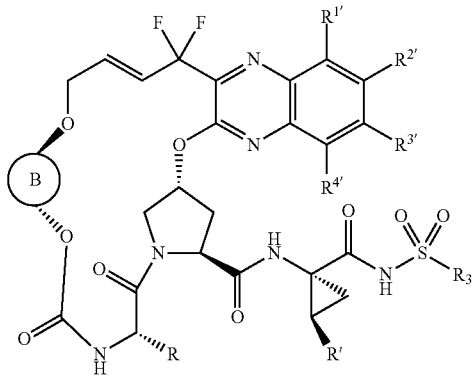

wherein $R^{1'}$, $R^{2'}$, $R^{3'}$ and $R^{4'}$ are each independently $R_6$, or $R^{1'}$ and $R^{2'}$, $R^{2'}$ and $R^{3'}$, or $R^{3'}$ and $R^{4'}$ taken together with the carbon atoms to which each is attached, form an aromatic, heteroaromatic, cyclic or heterocyclic ring;
Ⓑ is selected from —$C_3$-$C_{12}$ cycloalkyl, substituted —$C_3$-$C_{12}$ cycloalkyl; —$C_3$-$C_{12}$ cycloalkenyl, substituted —$C_3$-$C_{12}$ cycloalkenyl; —$C_3$-$C_{12}$ heterocycloalkyl, and substituted —$C_3$-$C_{12}$ heterocycloalkyl;
or Ⓑ is

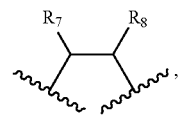

wherein $R_7$ and $R_8$ are each independently $C_1$-$C_8$ alkyl or $C_2$-$C_8$ alkenyl and are each independently optionally substituted with one or more halo;
each $R_6$ is independently selected from:
(i) hydrogen; halogen; —NO$_2$; —CN; or N$_3$;
(ii) -M-$R_3$, wherein M is O, S, or NH;
(iii) NR$_4$R$_5$;
(iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;
(v) aryl; substituted aryl; heteroaryl; or substituted heteroaryl; and
(vi) heterocycloalkyl or substituted heterocycloalkyl;
$R_3$ is independently selected from $C_1$-$C_8$ alkyl, —$C_2$-$C_8$ alkenyl, or —$C_2$-$C_8$ alkynyl each containing 0, 1, 2, or 3 heteroatoms selected from O, S or N, substituted —$C_1$-

C₈ alkyl, substituted —C₂-C₈ alkenyl, or substituted —C₂-C₈ alkynyl each containing 0, 1, 2, or 3 heteroatoms selected from O, S or N; —C₃-C₁₂ cycloalkyl, substituted —C₃-C₁₂ cycloalkyl; —C₃-C₁₂ cycloalkenyl, substituted —C₃-C₁₂ cycloalkenyl; heterocylic; substituted heterocyclic; aryl; substituted aryl; heteroaryl; and substituted heteroaryl;

each $R_4$ and $R_5$ are independently selected from H and $R_3$, or $R_4$ and $R_5$ combined together with the N they are attached to form a heterocyclic ring;

R and R' are each independently selected from the group consisting of:

(i) —C₁-C₈ alkyl, —C₂-C₈ alkenyl, or —C₂-C₈ alkynyl each containing 0, 1, 2, or 3 heteroatoms selected from O, S, or N; substituted —C₁-C₈ alkyl, substituted —C₂-C₈ alkenyl, or substituted —C₂-C₈ alkynyl each containing 0, 1, 2, or 3 heteroatoms selected from O, S or N; —C₃-C₁₂ cycloalkyl, substituted —C₃-C₁₂ cycloalkyl; —C₄-C₁₂ alkylcycloalkyl, substituted —C₄-C₁₂ alkylcycloalkyl; —C₃-C₁₂ cycloalkenyl, substituted —C₃-C₁₂ cycloalkenyl; —C₄-C₁₂ alkylcycloalkenyl, or substituted —C₄-C₁₂ alkylcycloalkenyl;

(ii) aryl; substituted aryl; heteroaryl; or substituted heteroaryl;

(iii) heterocycloalkyl or substituted heterocycloalkyl; and (iv) hydrogen; or deuterium;

R" is selected from hydrogen, methyl, ethyl, and allyl.

In certain embodiments of the compounds of Formulas I-VII, Ⓑ is selected from —C₃-C₁₂ cycloalkyl, substituted —C₃-C₁₂ cycloalkyl; —C₃-C₁₂ cycloalkenyl, substituted —C₃-C₁₂ cycloalkenyl; —C₃-C₁₂ heterocycloalkyl, and substituted —C₃-C₁₂ heterocycloalkyl;

In certain embodiments, Ⓑ in Formulas I-VII is C₃-C₁₂ carbocycle or 4- to 6-membered heterocycle and is optionally substituted with one or more substituents independently selected from halo, C₁-C₈ alkyl or C₂-C₈ alkenyl. For instance, Ⓑ can be a non-aromatic C₃-C₆ carbocycle or a non-aromatic 4- to 6-membered heterocycle and is optionally substituted with one or more substituents independently selected from halo, C₁-C₆ alkyl or C₂-C₆ alkenyl. More preferably, Ⓑ is saturated C₄-C₆ carbocycle or saturated 4- to 6-membered heterocycle and is optionally substituted with one or more substituents independently selected from halo, C₁-C₈ alkyl or C₂-C₈ alkenyl.

In certain embodiments of the compounds of Formulas I to VII, Ⓑ is selected from the group consisting of:

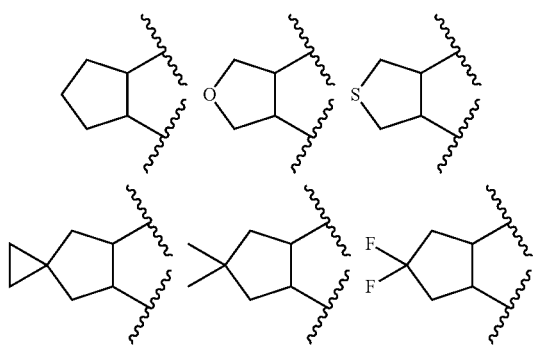

-continued

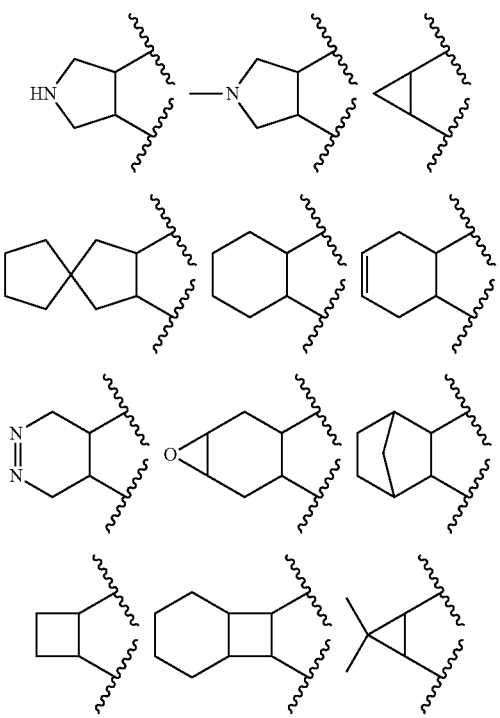

Highly preferably, Ⓑ is selected from the group below:

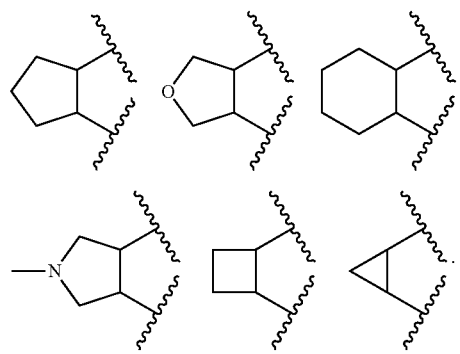

Preferably, $R^{1'}$, $R^{2'}$, $R^{3'}$ and $R^{4'}$ are hydrogen. Also preferably, $R^{1'}$ and $R^{4'}$ are hydrogen; and one of $R^{2'}$ and $R^{3'}$ is hydrogen, and the other is selected from halo, methyl optionally substituted with one or more halo, or —O-methyl optionally substituted with one or more halo. Also preferably, $R^{1'}$ and $R^{2'}$, or $R^{2'}$ and $R^{3'}$, or $R^{3'}$ and $R^{4'}$, taken together with the carbon atoms to which they are attached, form a 5- or 6-membered carbocycle or heterocycle (e.g., phenyl), and the rest of $R^{1'}$, $R^{2'}$, $R^{3'}$ and $R^{4'}$ preferably are hydrogen.

Preferably, $R_3$ is

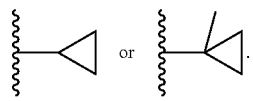

Preferably, R' is

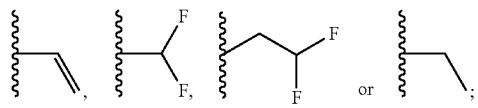

more preferably

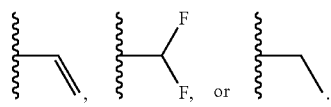

Preferably, R is

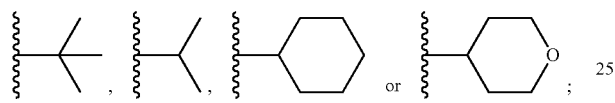

more preferably

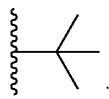

In one embodiment, the present invention features compounds of Formula VII or pharmaceutically acceptable salts thereof, wherein Ⓑ is

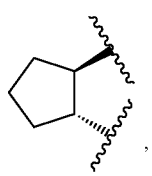

R' is vinyl

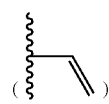

or difluoromethyl

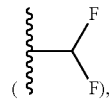

$R_3$ is

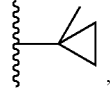

and R is

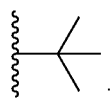

In another embodiment, the present invention features compounds of Formula VII or pharmaceutically acceptable salts thereof, wherein Ⓑ is

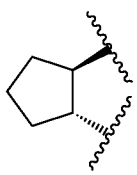

R' is vinyl

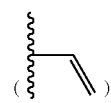

or difluoromethyl

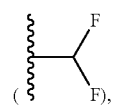

$R_3$ is

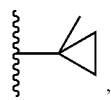

and R is

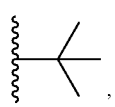

$R^{3'}$ is —O-methyl optionally substituted with one or more halo, and $R^{1'}$, $R^{2'}$, and $R^{4'}$ are hydrogen.

In yet another embodiment, the present invention features compounds of Formula VII or pharmaceutically acceptable salts thereof, wherein Ⓑ is

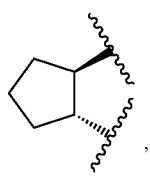

R' is vinyl

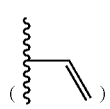

or difluoromethyl

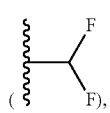

$R_3$ is

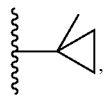

and R is

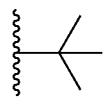

and $R^{1'}$, $R^{2'}$, $R^{3'}$ and $R^{4'}$ are hydrogen.

In another embodiment, the present invention features compounds of Formula VII or pharmaceutically acceptable salts thereof, wherein Ⓑ is

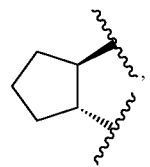

R' is vinyl

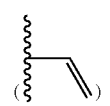

or difluoromethyl

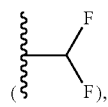

$R_3$ is

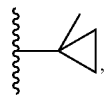

and R is

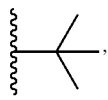

$R^{3'}$ is halo (e.g, F), and $R^{1'}$, $R^{2'}$, and $R^{4'}$ are hydrogen.

In still another embodiment, the present invention features compounds of Formula VII or pharmaceutically acceptable salts thereof, wherein Ⓑ is

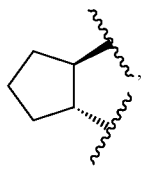

R' is vinyl

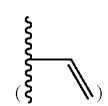

or difluoromethyl

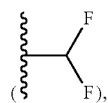

$R_3$ is

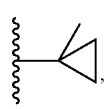

and R is

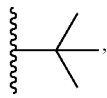

$R^{3'}$ and $R^{4'}$ taken together with carbon atoms to which they are attached form phenyl, and $R^{1'}$ and $R^{2'}$ are hydrogen.

In another aspect, the invention provides a compound of Formula VIII:

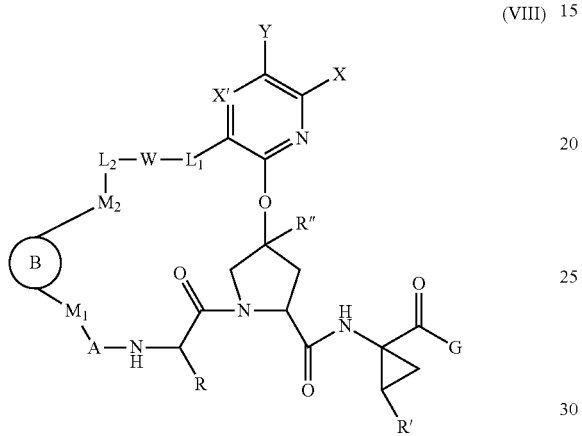

(VIII)

wherein

A is absent, or selected from —(C=O)—, —S(O)$_2$-, —C(=N—OR$_1$)— and —C(=N—CN)—;

Ⓑ is selected from —C$_3$-C$_{12}$ cycloalkyl, substituted —C$_3$-C$_{12}$ cycloalkyl; —C$_3$-C$_{12}$ cycloalkenyl, substituted —C$_3$-C$_{12}$ cycloalkenyl; —C$_3$-C$_{12}$ heterocycloalkyl, and substituted —C$_3$-C$_{12}$ heterocycloalkyl;

M$_1$ and M$_2$ are selected from O and NR$_1$; wherein R$_1$ is selected at each occurrence from the group consisting of:
(i) hydrogen;
(ii) aryl; substituted aryl; heteroaryl; substituted heteroaryl;
(iii) heterocycloalkyl or substituted heterocycloalkyl; and
(iv) —C$_1$-C$_8$ alkyl, —C$_2$-C$_8$ alkenyl, or —C$_2$-C$_8$ alkynyl each containing 0, 1, 2, or 3 heteroatoms independently selected from O, S and N; substituted —C$_1$-C$_8$ alkyl, substituted —C$_2$-C$_8$ alkenyl, or substituted —C$_2$-C$_8$ alkynyl each containing 0, 1, 2, or 3 heteroatoms selected from O, S or N; —C$_3$-C$_{12}$ cycloalkyl, or substituted —C$_3$-C$_{12}$ cycloalkyl; —C$_3$-C$_{12}$ cycloalkenyl, or substituted —C$_3$-C$_{12}$ cycloalkenyl;

L$_1$ and L$_2$ are independently selected from —C$_1$-C$_8$ alkylene, —C$_2$-C$_8$ alkenylene, or —C$_2$-C$_8$ alkynylene each containing 0, 1, 2, or 3 heteroatoms independently selected from O, S and N; substituted —C$_1$-C$_8$ alkylene, substituted —C$_2$-C$_8$ alkenylene, or substituted —C$_2$-C$_8$ alkynylene each containing 0, 1, 2, or 3 heteroatoms selected from O, S or N; —C$_3$-C$_{12}$ cycloalkylene, or substituted —C$_3$-C$_{12}$ cycloalkylene each containing 0, 1, 2, or 3 heteroatoms selected from O, S or N; —C$_3$-C$_{12}$ cycloalkenylene, or substituted —C$_3$-C$_{12}$ cycloalkenylene each containing 0, 1, 2, or 3 heteroatoms selected from O, S or N;

W is absent, or selected from —O—, —S—, —NH—, —N(Me)-, —C(O)NH—, and —C(O)N(Me)-;

X and Y, taken together with the carbon atoms to which they are attached, form a cyclic moiety selected from aryl, substituted aryl, heteroaryl, substituted heteroaryl, heterocyclic, and substituted heterocylic;

X' is selected from N and —C(R$_2$)—, where R$_2$ is selected from the group consisting of:
(i) hydrogen, halogen, CN, CF$_3$, NO$_2$, OR$_1$, SR$_1$, —NHS(O)$_2$—R$_2$, —NH(SO$_2$)NR$_3$R$_4$, NR$_3$R$_4$, CO$_2$R$_1$, COR$_1$, CONR$_1$R$_2$, N(R$_1$)COR$_2$;
(ii) aryl; substituted aryl; heteroaryl; substituted heteroaryl;
(iii) heterocycloalkyl or substituted heterocycloalkyl; and
(iv) —C$_1$-C$_8$ alkyl, —C$_2$-C$_8$ alkenyl, or —C$_2$-C$_8$ alkynyl each containing 0, 1, 2, or 3 heteroatoms independently selected from O, S and N; substituted —C$_1$-C$_8$ alkyl, substituted —C$_2$-C$_8$ alkenyl, or substituted —C$_2$-C$_8$ alkynyl each containing 0, 1, 2, or 3 heteroatoms selected from O, S or N; —C$_3$-C$_{12}$ cycloalkyl, or substituted —C$_3$-C$_{12}$ cycloalkyl; —C$_3$-C$_{12}$ cycloalkenyl, or substituted —C$_3$-C$_{12}$ cycloalkenyl;

R and R' are each independently selected from the group consisting of:
(i) —C$_1$-C$_8$ alkyl, —C$_2$-C$_8$ alkenyl, or —C$_2$-C$_8$ alkynyl each containing 0, 1, 2, or 3 heteroatoms independently selected from O, S and N; substituted —C$_1$-C$_8$ alkyl, substituted —C$_2$-C$_8$ alkenyl, or substituted —C$_2$-C$_8$ alkynyl each containing 0, 1, 2, or 3 heteroatoms selected from O, S or N; —C$_3$-C$_{12}$ cycloalkyl, or substituted —C$_3$-C$_{12}$ cycloalkyl; —C$_4$-C$_{12}$ alkylcycloalkyl, or substituted —C$_4$-C$_{12}$ alkylcycloalkyl; —C$_3$-C$_{12}$ cycloalkenyl, or substituted —C$_3$-C$_{12}$ cycloalkenyl; —C$_4$-C$_{12}$ alkylcycloalkenyl, or substituted —C$_4$-C$_{12}$ alkylcycloalkenyl;
(ii) aryl; substituted aryl; heteroaryl; substituted heteroaryl;
(iii) heterocycloalkyl or substituted heterocycloalkyl; and
(iv) hydrogen; deuterium;

G is selected from —OH, —NHS(O)$_2$—R$_3$, —NH(SO$_2$)NR$_4$R$_5$, and NR$_4$R$_5$;

R$_3$ is selected from:
(i) aryl; substituted aryl; heteroaryl; substituted heteroaryl
(ii) heterocycloalkyl; substituted heterocycloalkyl; and
(iii) —C$_1$-C$_8$ alkyl, —C$_2$-C$_8$ alkenyl, or —C$_2$-C$_8$ alkynyl each containing 0, 1, 2, or 3 heteroatoms selected from O, S or N, substituted —C$_1$-C$_8$ alkyl, substituted —C$_2$-C$_8$ alkenyl, or substituted —C$_2$-C$_8$ alkynyl each containing 0, 1, 2, or 3 heteroatoms selected from O, S or N; —C$_3$-C$_{12}$ cycloalkyl, or substituted —C$_3$-C$_{12}$ cycloalkyl; —C$_3$-C$_{12}$ cycloalkenyl, or substituted —C$_3$-C$_{12}$ cycloalkenyl; heterocylic; substituted heterocyclic;

R$_4$ and R$_5$ are independently selected from:
(i) hydrogen;
(ii) aryl; substituted aryl; heteroaryl; substituted heteroaryl;
(iii) heterocycloalkyl or substituted heterocycloalkyl;
(iv) —C$_1$-C$_8$ alkyl, —C$_2$-C$_8$ alkenyl, or —C$_2$-C$_8$ alkynyl each containing 0, 1, 2, or 3 heteroatoms independently selected from O, S and N; substituted —C$_1$-C$_8$ alkyl, substituted —C$_2$-C$_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl; heterocyclic, or substitututed heterocyclic;

and

R" is selected from hydrogen, methyl, ethyl and allyl.

Representative compounds of the invention include, but are not limited to, the following compounds (example 1 to example 256 in Table 1) according to Formula VIII wherein R, -$L_2$-W-$L_1$-,

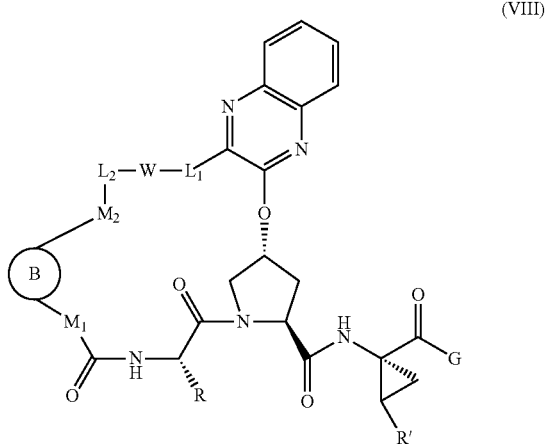

(VIII)

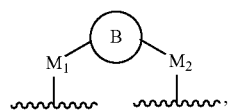

R' and G are delineated for each example in Table 1.

TABLE 1

| Example # | R | —$L_2$—W—$L_1$— | $M_1$-B-$M_2$ | R' | G |
|---|---|---|---|---|---|
| 1. | tBu | CH2CH=CHCF2- | cyclopentane-1,2-diyl diether | allyl | NHSO2-cyclopropyl |
| 2. | tBu | CH2CH=CHCF2- | cyclopentane-1,2-diyl diether | CHF2 | NHSO2-cyclopropyl |
| 3. | tBu | CH2CH=CHCF2- | cyclopentane-1,2-diyl diether | CH2CHF2 | NHSO2-cyclopropyl |
| 4. | tBu | CH2CH=CHCF2- | cyclopentane-1,2-diyl diether | ethyl | NHSO2-cyclopropyl |
| 5. | tBu | CH2CH=CHCF2- | cyclopentane-1,2-diyl diether | allyl | NHSO2-C(CH3)-cyclopropyl |
| 6. | tBu | CH2CH=CHCF2- | cyclopentane-1,2-diyl diether | CHF2 | NHSO2-C(CH3)-cyclopropyl |

TABLE 1-continued
| Example # | R | —L₂—W—L₁— | 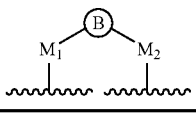 | R' | G |
|---|---|---|---|---|---|
| 7. |  | 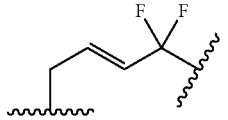 | 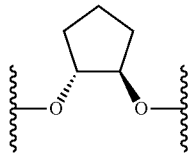 | 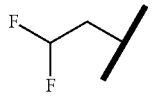 | 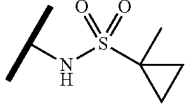 |
| 8. |  | 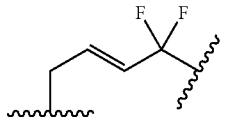 | 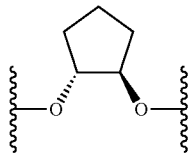 |  | 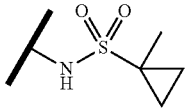 |
| 9. |  | 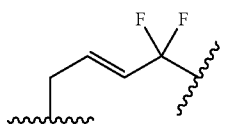 | 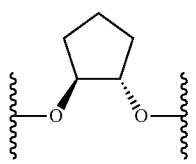 | 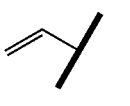 | 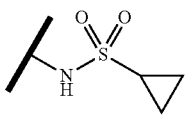 |
| 10. |  | 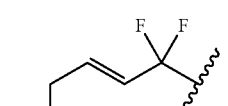 | 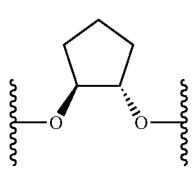 | 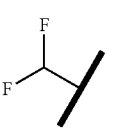 | 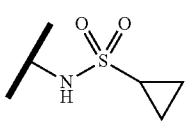 |
| 11. |  | 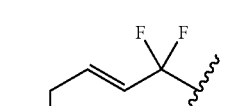 | 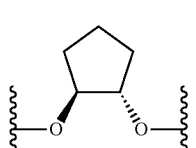 | 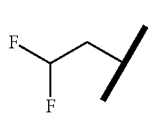 | 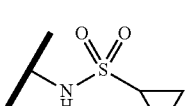 |
| 12. |  | 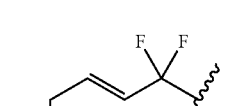 | 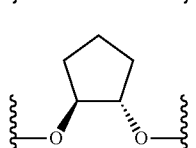 |  | 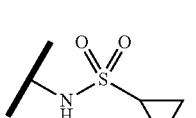 |
| 13. |  | 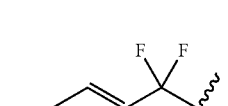 | 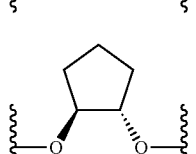 | 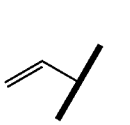 | 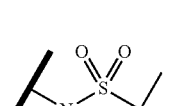 |
| 14. |  | 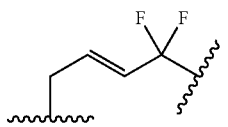 | 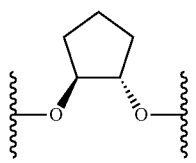 | 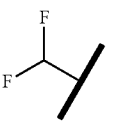 | 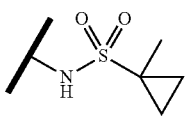 |
| 15. |  | 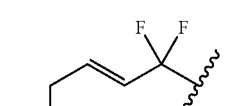 | 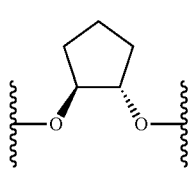 | 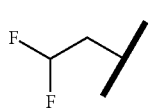 | 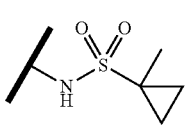 |

US 9,220,748 B2
TABLE 1-continued
| Example # | R | —L₂—W—L₁— | ⟨M₁—B—M₂⟩ | R' | G |
|---|---|---|---|---|---|
| 16. | 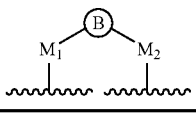 |  | 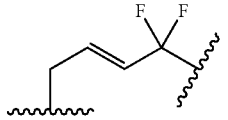 | 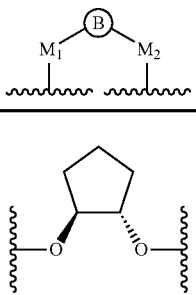 |  |
| 17. | 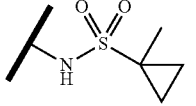 |  | 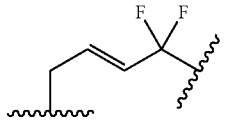 | 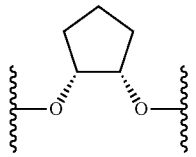 |  |
| 18. | 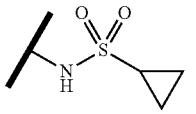 |  | 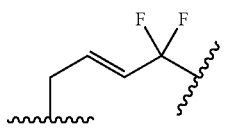 | 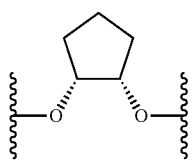 | 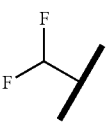 |
| 19. | 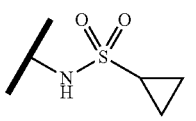 |  | 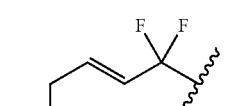 | 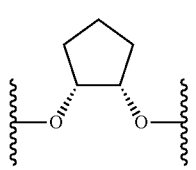 | 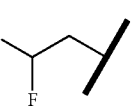 |
| 20. | 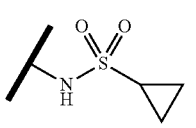 |  | 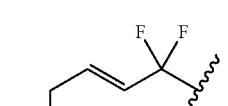 | 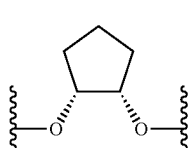 |  |
| 21. | 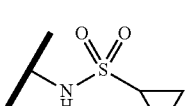 |  | 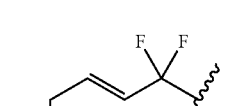 | 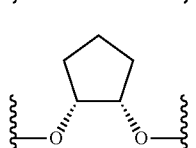 |  |
| 22. | 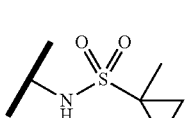 |  | 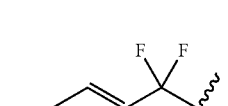 | 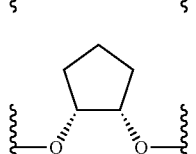 | 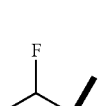 |
| 23. | 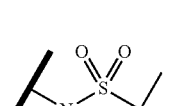 |  | 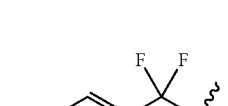 | 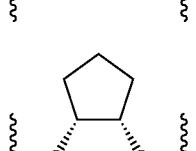 | 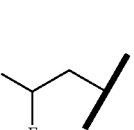 |
| 24. | 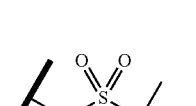 |  | 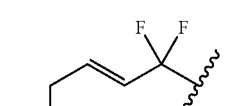 | 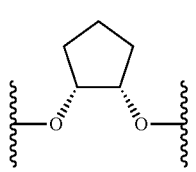 | 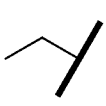 |

TABLE 1-continued
| Example # | R | —L₂—W—L₁— | M₁–B–M₂ | R' | G |
|---|---|---|---|---|---|
| 25. | 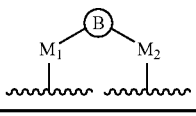 |  | 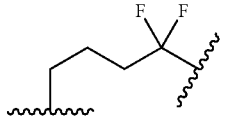 | 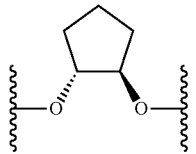 | 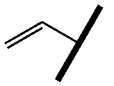 |
| 26. | 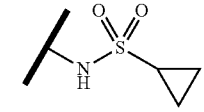 |  | 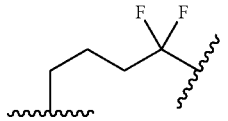 | 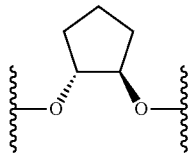 | 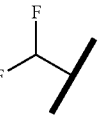 |
| 27. | 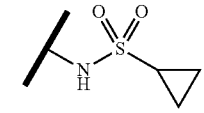 |  | 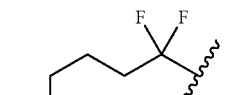 | 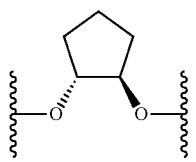 | 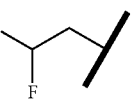 |
| 28. | 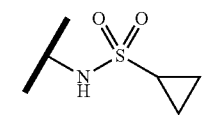 |  | 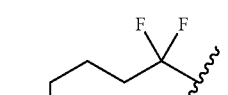 | 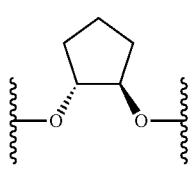 |  |
| 29. | 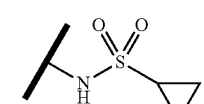 |  | 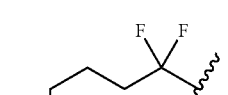 | 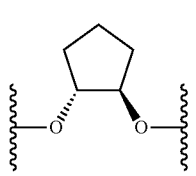 | 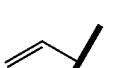 |
| 30. | 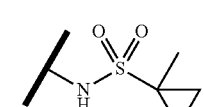 |  | 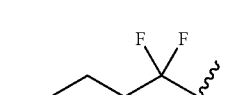 | 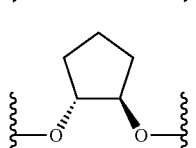 | 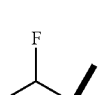 |
| 31. | 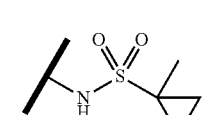 |  | 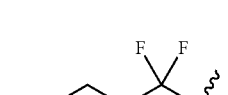 | 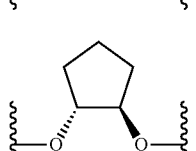 | 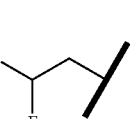 |
| 32. | 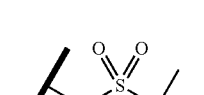 |  | 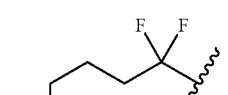 | 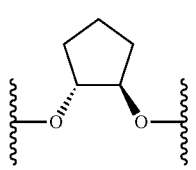 |  |
| 33. | 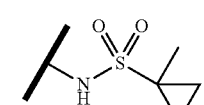 |  | 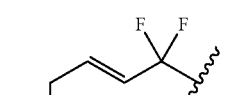 | 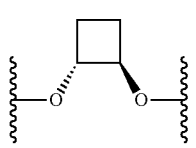 | 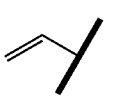 |

TABLE 1-continued

TABLE 1-continued
| Example # | R | —L₂—W—L₁— | 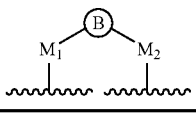 | R' | G |
|---|---|---|---|---|---|
| 44. |  | 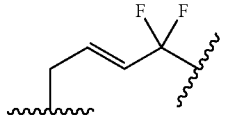 | 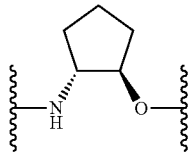 |  | 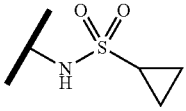 |
| 45. |  | 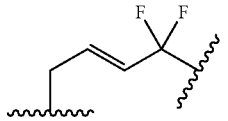 | 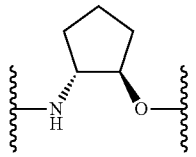 |  | 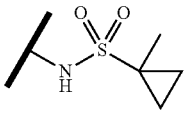 |
| 46. |  | 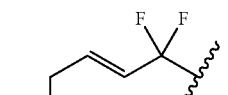 | 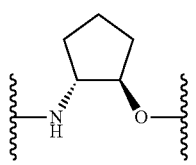 | 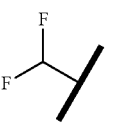 | 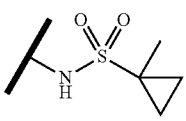 |
| 47. |  | 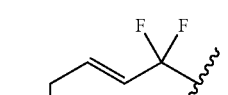 | 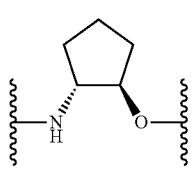 | 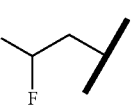 | 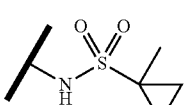 |
| 48. |  | 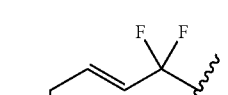 | 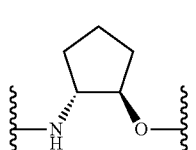 |  | 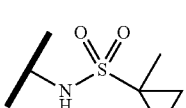 |
| 49. |  | 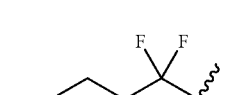 | 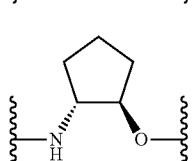 |  | 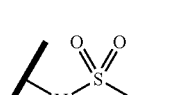 |
| 50. |  | 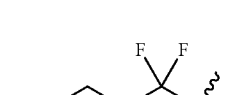 | 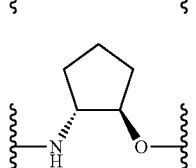 | 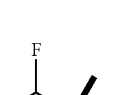 | 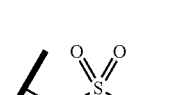 |
| 51. |  |  | 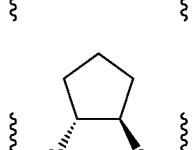 | 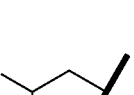 | 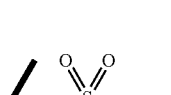 |
| 52. |  | 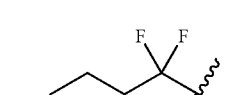 | 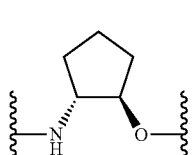 | 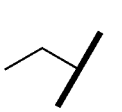 | 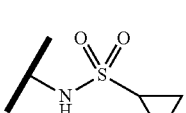 |

TABLE 1-continued
| Example # | R | —L₂—W—L₁— | 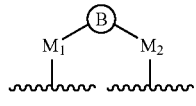 | R' | G |
|---|---|---|---|---|---|
| 53. |  | 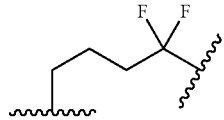 | 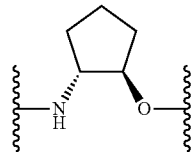 |  | 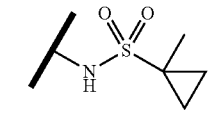 |
| 54. |  | 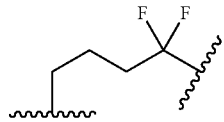 | 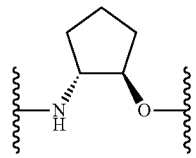 | 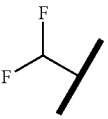 | 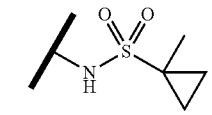 |
| 55. |  | 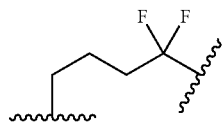 | 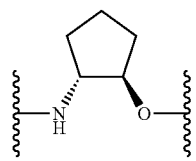 | 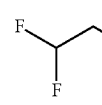 | 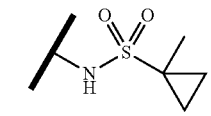 |
| 56. |  | 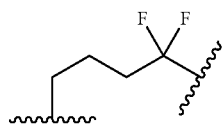 | 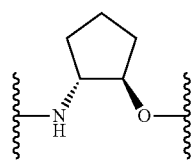 |  | 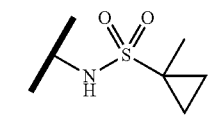 |
| 57. |  | 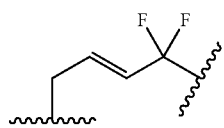 | 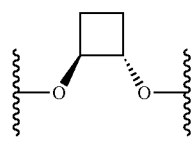 |  | 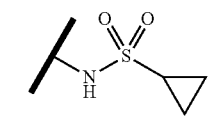 |
| 58. |  | 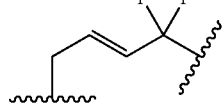 | 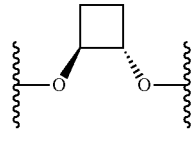 | 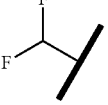 | 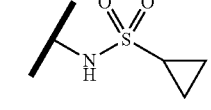 |
| 59. |  | 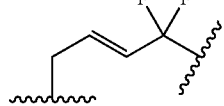 | 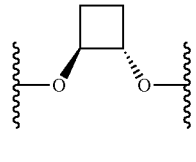 | 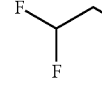 | 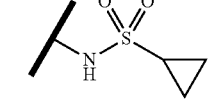 |
| 60. |  | 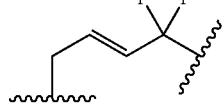 | 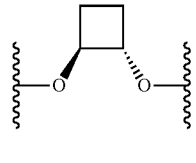 |  | 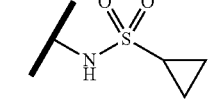 |
| 61. |  | 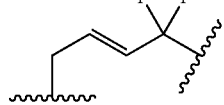 | 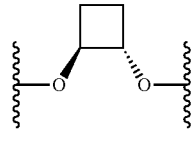 |  | 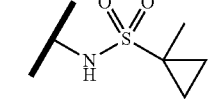 |

TABLE 1-continued
| Example # | R | —L₂—W—L₁— | 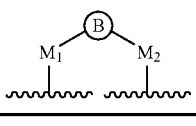 | R' | G |
|---|---|---|---|---|---|
| 62. |  | 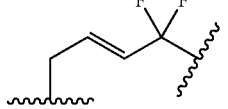 | 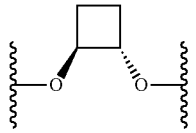 |  | 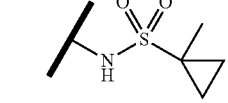 |
| 63. |  | 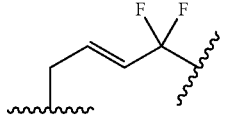 | 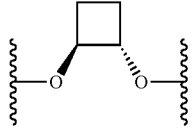 |  | 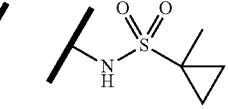 |
| 64. |  | 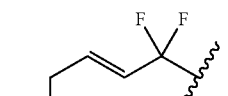 | 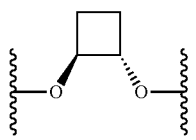 |  | 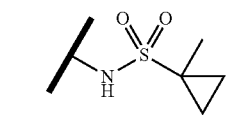 |
| 65. |  | 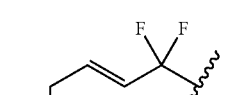 | 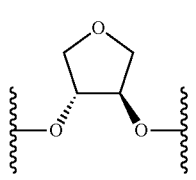 |  | 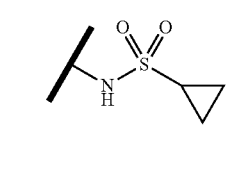 |
| 66. |  | 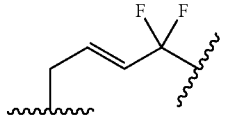 | 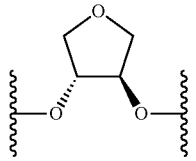 |  | 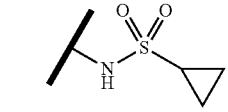 |
| 67. |  | 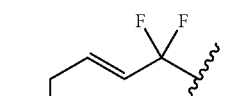 | 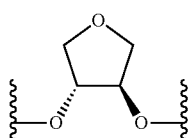 |  | 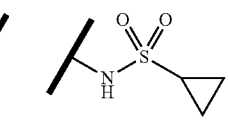 |
| 68. |  | 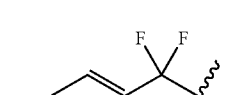 | 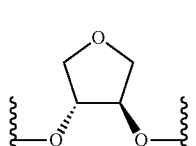 |  | 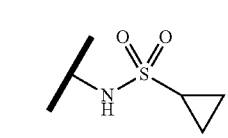 |
| 69. |  | 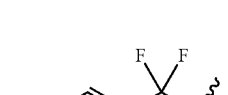 | 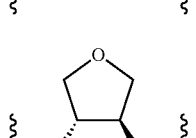 |  | 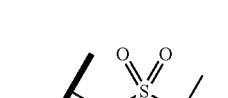 |
| 70. |  | 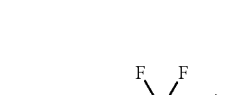 | 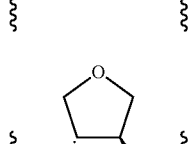 |  |  |

TABLE 1-continued
| Example # | R | —L₂—W—L₁— | 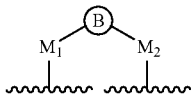 | R' | G |
|---|---|---|---|---|---|
| 71. |  | 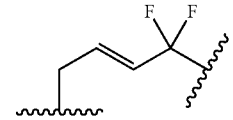 | 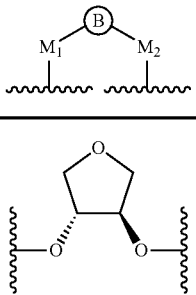 | 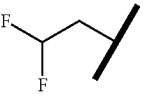 | 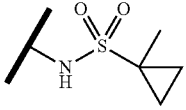 |
| 72. |  | 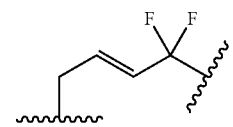 | 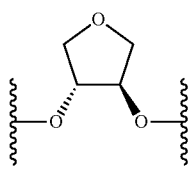 |  | 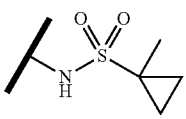 |
| 73. |  | 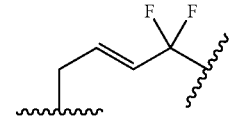 | 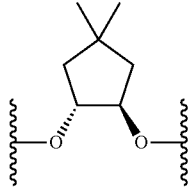 |  | 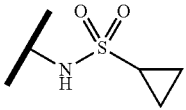 |
| 74. |  | 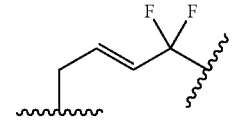 | 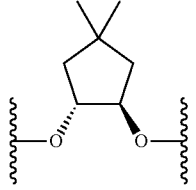 |  | 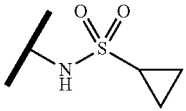 |
| 75. |  | 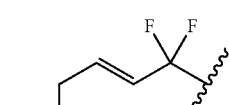 | 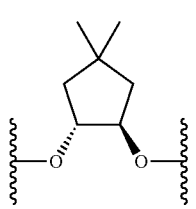 | 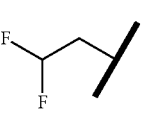 | 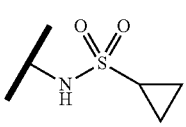 |
| 76. |  | 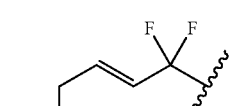 | 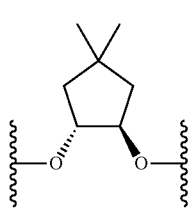 |  | 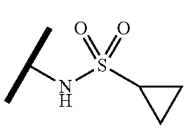 |
| 77. |  | 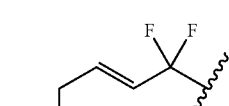 | 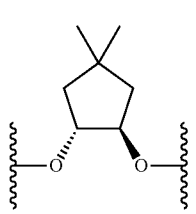 |  | 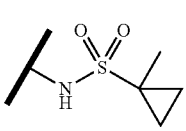 |

TABLE 1-continued
| Example # | R | —L₂—W—L₁— | M₁ (B) M₂ | R' | G |
|---|---|---|---|---|---|
| 78. | 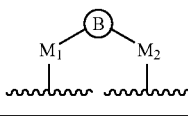 |  | 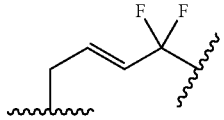 | 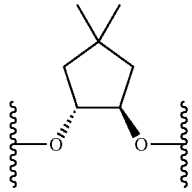 | 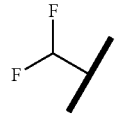 |
| 79. | 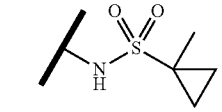 |  | 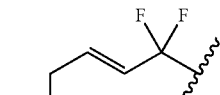 | 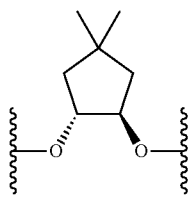 | 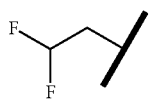 |
| 80. | 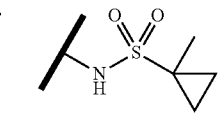 |  | 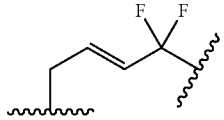 | 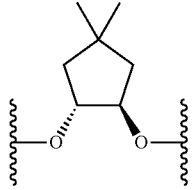 |  |
| 81. | 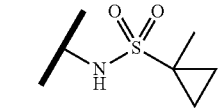 |  | 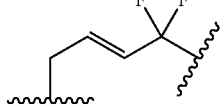 | 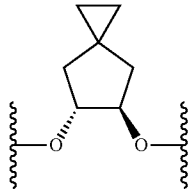 |  |
| 82. | 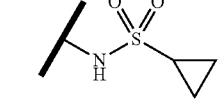 |  | 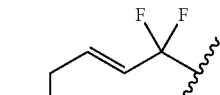 | 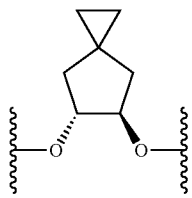 | 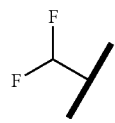 |
| 83. | 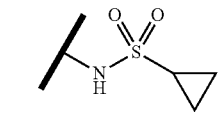 |  | 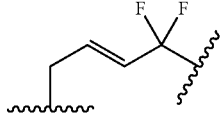 | 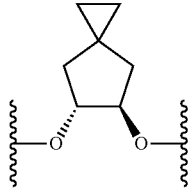 | 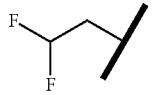 |
| 84. | 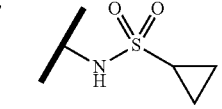 |  | 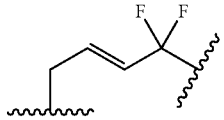 | 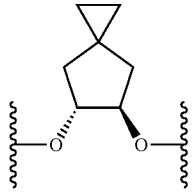 |  |

US 9,220,748 B2
TABLE 1-continued
| Example # | R | —L₂—W—L₁— | 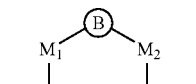 | R' | G |
|---|---|---|---|---|---|
| 85. |  | 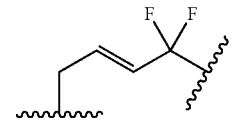 | 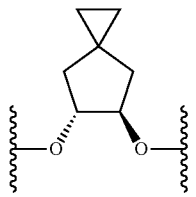 | 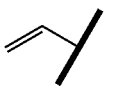 | 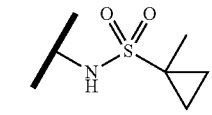 |
| 86. |  | 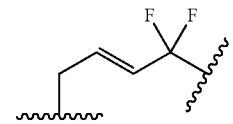 | 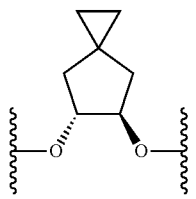 | 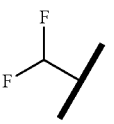 | 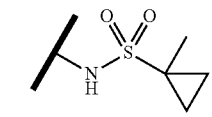 |
| 87. |  | 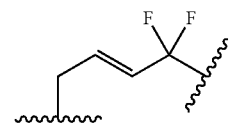 | 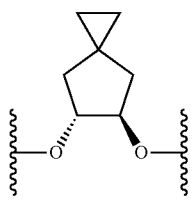 | 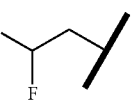 | 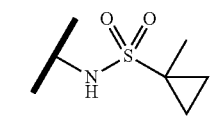 |
| 88. |  | 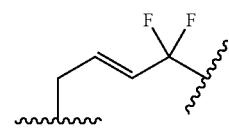 | 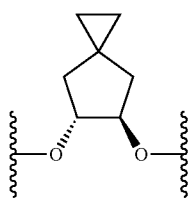 |  | 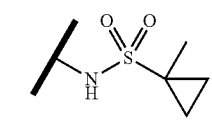 |
| 89. |  | 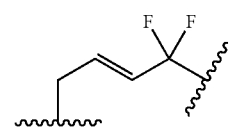 | 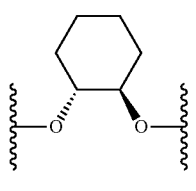 | 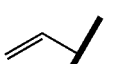 | 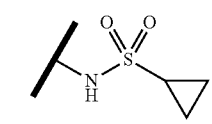 |
| 90. |  | 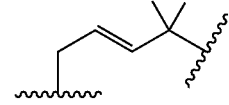 | 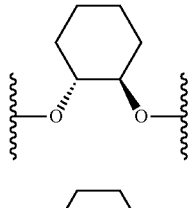 | 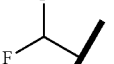 | 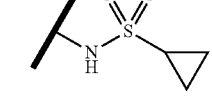 |
| 91. |  | 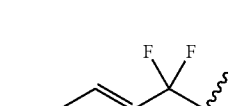 | 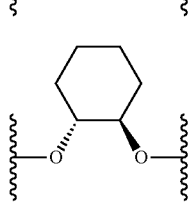 |  | 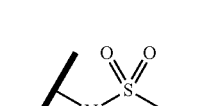 |
| 92. |  | 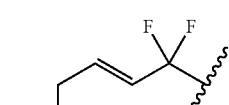 | 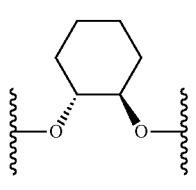 |  | 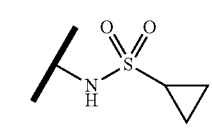 |

TABLE 1-continued
| Example # | R | —L₂—W—L₁— | 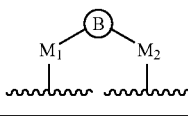 | R' | G |
|---|---|---|---|---|---|
| 93. |  | 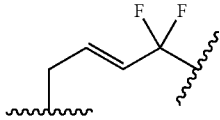 |  | 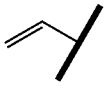 | 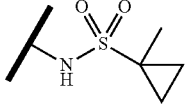 |
| 94. |  | 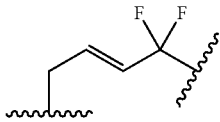 |  | 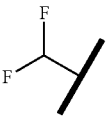 | 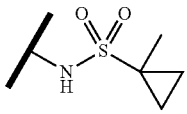 |
| 95. |  | 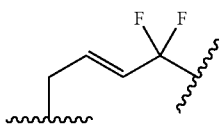 | 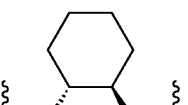 | 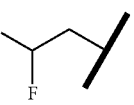 | 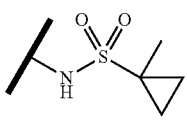 |
| 96. |  | 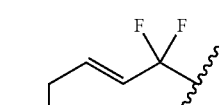 | 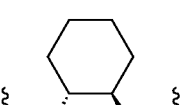 |  | 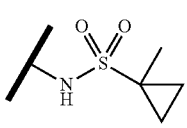 |
| 97. |  | 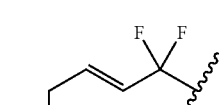 | 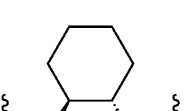 |  | 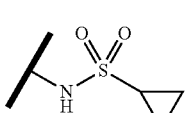 |
| 98. |  | 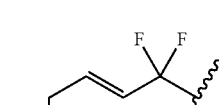 | 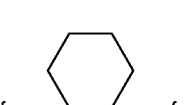 | 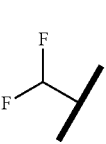 | 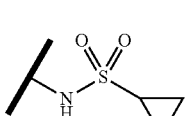 |
| 99. |  | 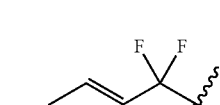 | 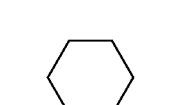 | 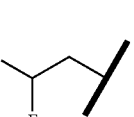 | 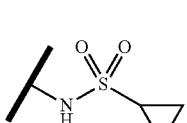 |
| 100. |  | 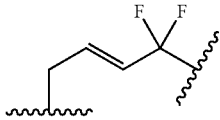 |  |  | 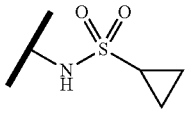 |

TABLE 1-continued
| Example # | R | —L₂—W—L₁— | 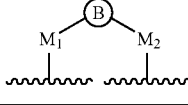 | R' | G |
|---|---|---|---|---|---|
| 101. | | | | | |
| 102. | | | | | |
| 103. | | | | | |
| 104. | | | | | |
| 105. | | | | | |
| 106. | | | | | |
| 107. | | | | | |
| 108. | | | | | |

TABLE 1-continued
| Example # | R | —L₂—W—L₁— | M₁ B M₂ | R' | G |
|---|---|---|---|---|---|
| 109. |  | 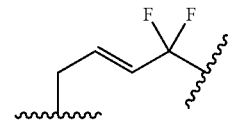 | 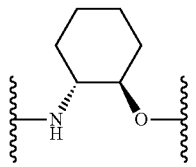 |  | 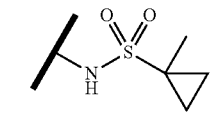 |
| 110. |  | 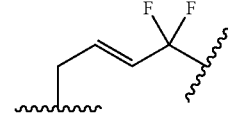 | 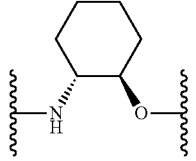 | 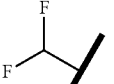 | 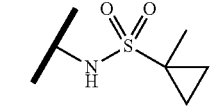 |
| 111. |  | 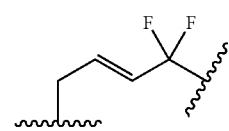 | 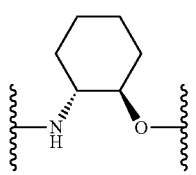 | 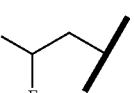 | 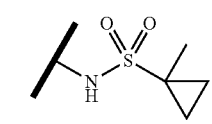 |
| 112. |  | 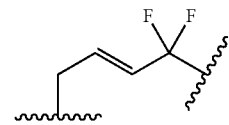 | 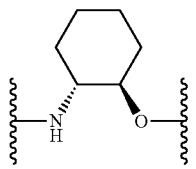 |  | 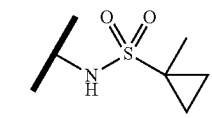 |
| 113. |  | 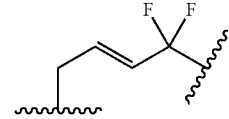 | 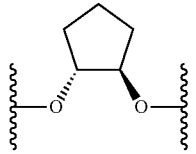 |  | 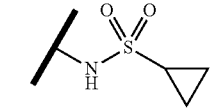 |
| 114. | 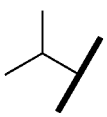 | 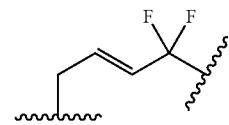 | 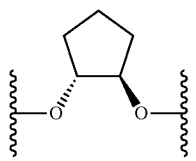 | 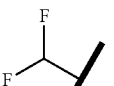 | 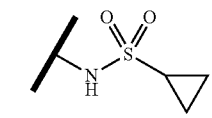 |
| 115. |  | 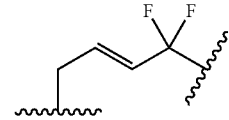 | 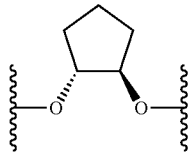 | 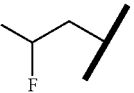 | 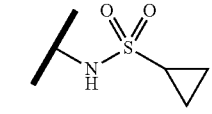 |
| 116. |  | 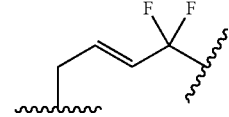 | 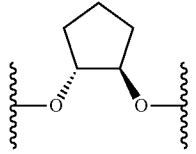 |  | 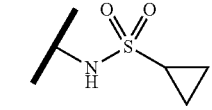 |
| 117. | 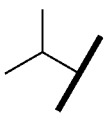 | 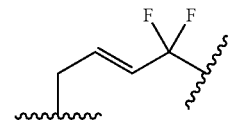 | 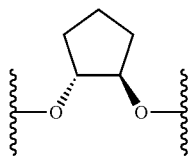 |  | 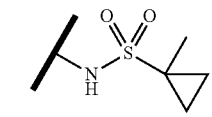 |

US 9,220,748 B2
TABLE 1-continued
| Example # | R | —L₂—W—L₁— | ![B with M₁ M₂] | R' | G |
|---|---|---|---|---|---|
| 118. | 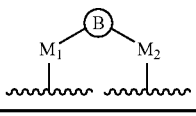 |  | 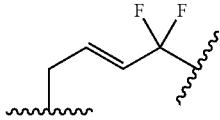 | 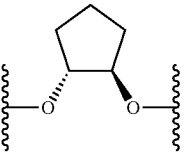 | 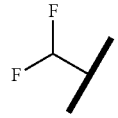 |
| 119. | 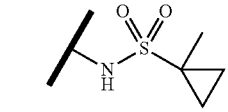 |  | 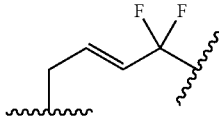 | 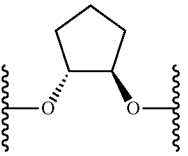 | 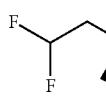 |
| 120. | 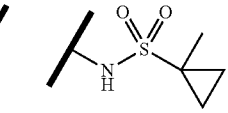 | 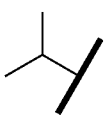 | 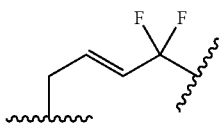 | 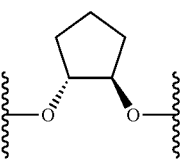 | 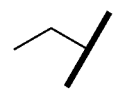 |
| 121. | 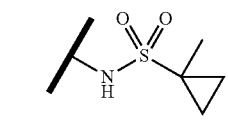 |  | 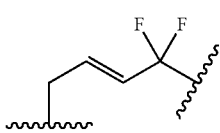 | 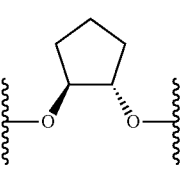 | 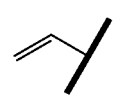 |
| 122. | 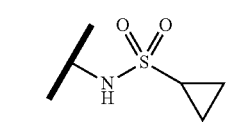 |  | 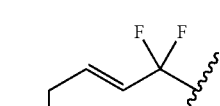 | 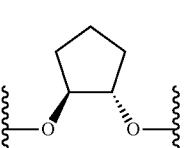 | 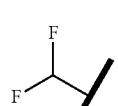 |
| 123. | 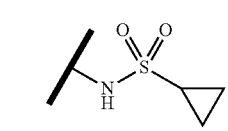 | 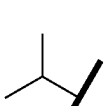 | 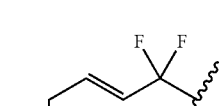 | 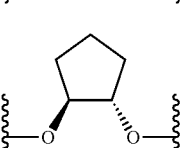 | 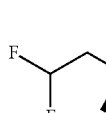 |
| 124. | 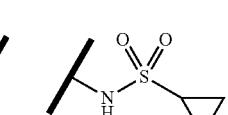 | 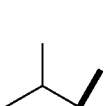 | 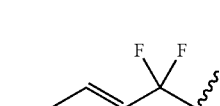 | 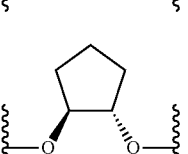 | 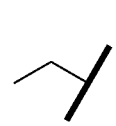 |
| 125 | 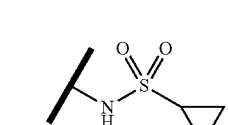 |  | 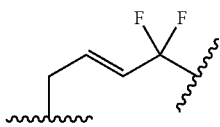 | 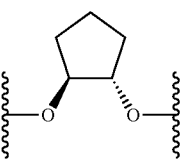 | 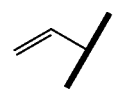 |
| 126. | 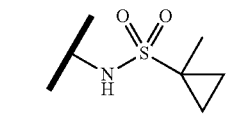 | 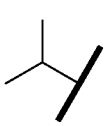 | 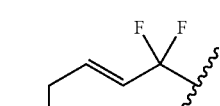 | 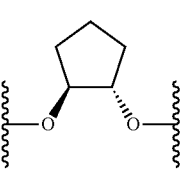 | 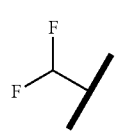 |

US 9,220,748 B2
53 54
TABLE 1-continued
| Example # | R | —L₂—W—L₁— | | R' | G |
|---|---|---|---|---|---|
| 127. | 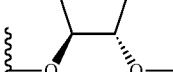 |  | 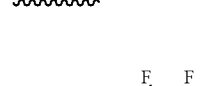 | 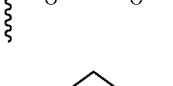 | 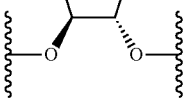 |
| 128. |  | 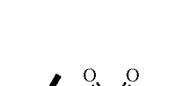 |  | 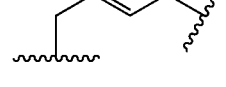 | 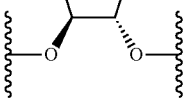 |
| 129. |  |  | 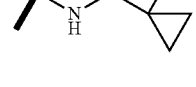 |  | 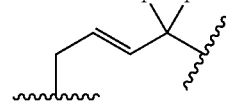 |
| 130. | 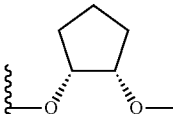 | 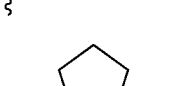 |  | 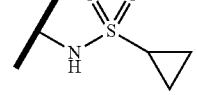 |  |
| 131. | 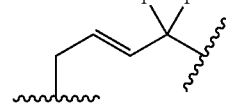 | 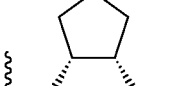 | 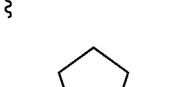 | 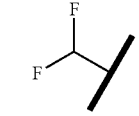 | 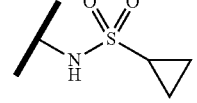 |
| 132. |  | 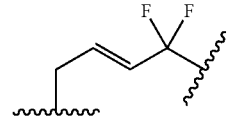 | 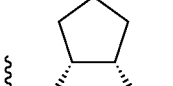 | 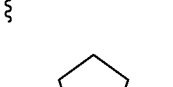 | 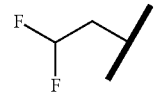 |
| 133. | 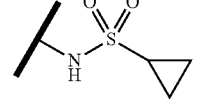 |  | 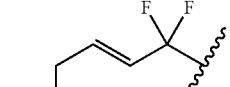 |  | 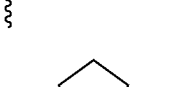 |
| 134. |  | 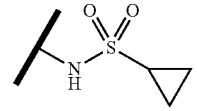 |  | 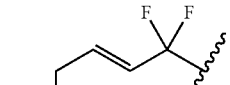 |  |
| 135. |  | 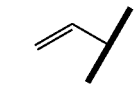 | 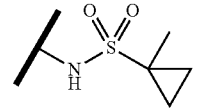 |  | 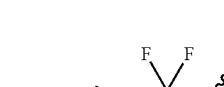 |

TABLE 1-continued
| Example # | R | —L₂—W—L₁— | M₁—B—M₂ | R' | G |
|---|---|---|---|---|---|
| 136. | 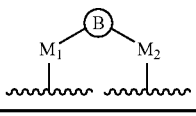 |  | 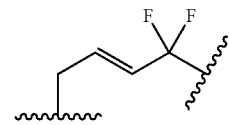 | 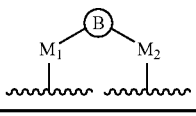 |  |
| 137. | 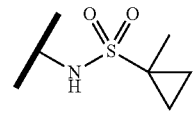 |  | 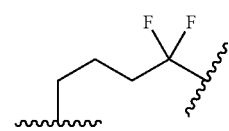 |  |  |
| 138. | 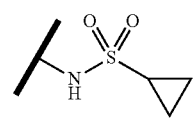 | 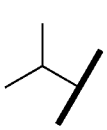 | 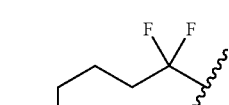 | 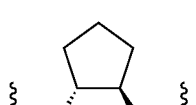 | 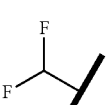 |
| 139. | 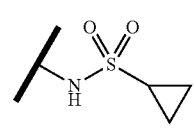 | 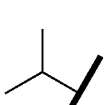 | 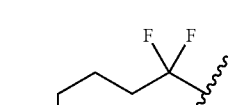 | 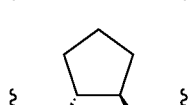 | 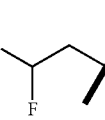 |
| 140. | 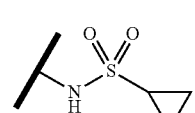 | 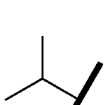 | 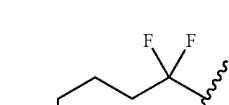 | 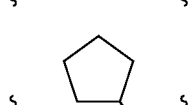 |  |
| 141. | 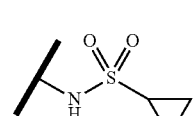 | 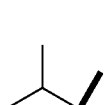 | 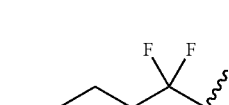 | 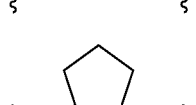 | 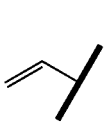 |
| 142. | 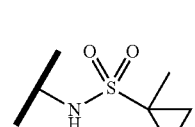 | 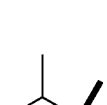 | 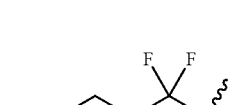 |  |  |
| 143. | 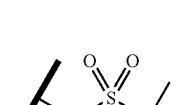 |  | 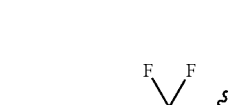 | 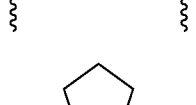 | 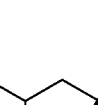 |
| 144. | 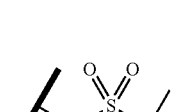 |  | 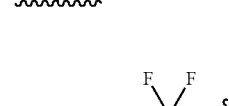 | 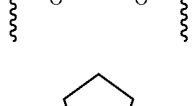 | 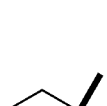 |

TABLE 1-continued
| Example # | R | —L₂—W—L₁— | 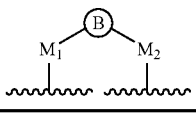 | R' | G |
|---|---|---|---|---|---|
| 145. | | | | | |
| 146. | | | | | |
| 147. | | | | | |
| 148. | | | | | |
| 149. | | | | | |
| 150. | | | | | |
| 151. | | | | | |
| 152. | | | | | |
| 153. | | | | | |
| 154. | | | | | |

US 9,220,748 B2
TABLE 1-continued
| Example # | R | —L₂—W—L₁— | 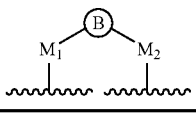 | R' | G |
|---|---|---|---|---|---|
| 155. |  | 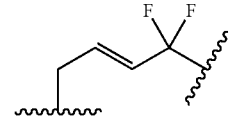 | 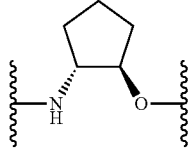 | 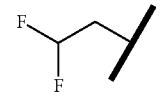 | 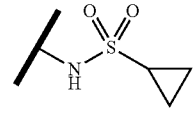 |
| 156. |  | 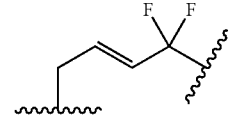 | 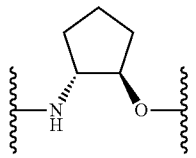 |  | 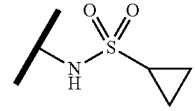 |
| 157. | 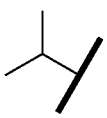 | 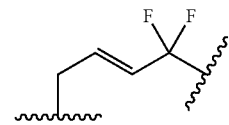 | 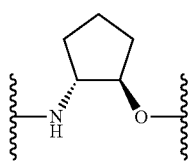 |  | 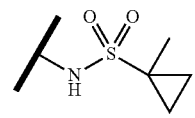 |
| 158. |  | 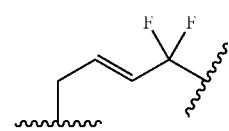 | 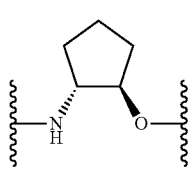 | 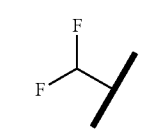 | 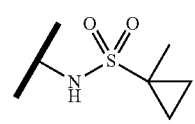 |
| 159. | 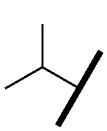 | 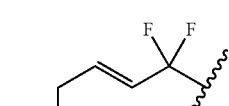 | 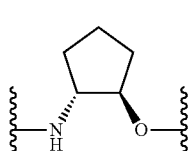 | 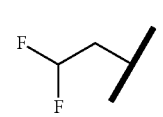 | 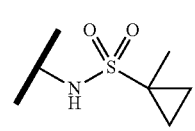 |
| 160. | 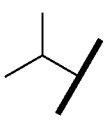 | 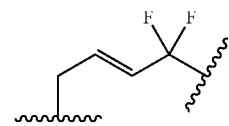 | 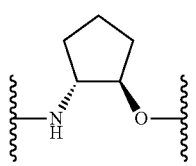 |  | 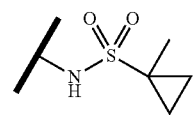 |
| 161. | 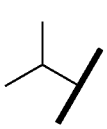 | 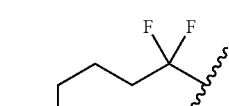 | 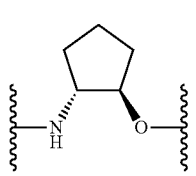 |  | 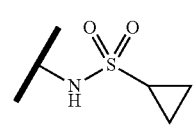 |
| 162. | 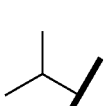 | 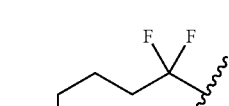 | 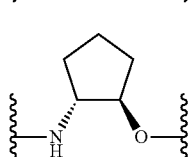 | 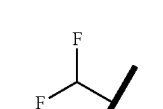 | 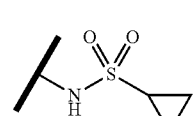 |
| 163. | 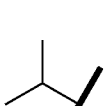 | 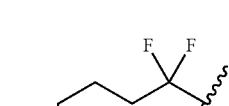 | 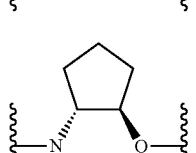 | 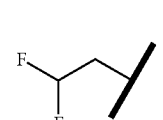 | 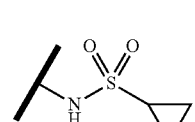 |

TABLE 1-continued
| Example # | R | —L₂—W—L₁— | 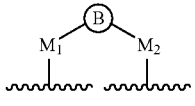 | R' | G |
|---|---|---|---|---|---|
| 164. | | | | | |
| 165. | | | | | |
| 166. | | | | | |
| 167. | | | | | |
| 168. | | | | | |
| 169. | | | | | |
| 170. | | | | | |
| 171. | | | | | |
| 172. | | | | | |

US 9,220,748 B2
TABLE 1-continued
| Example # | R | —L$_2$—W—L$_1$— | M$_1$—B—M$_2$ | R' | G |
|---|---|---|---|---|---|
| 173. | 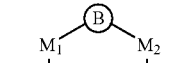 | 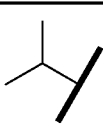 | 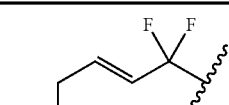 | 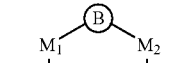 |  |
| 174. | 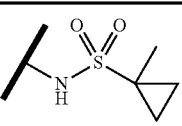 | 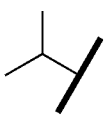 | 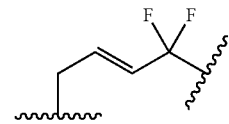 | 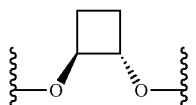 | 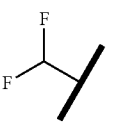 |
| 175. | 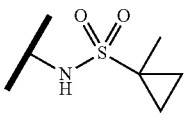 |  | 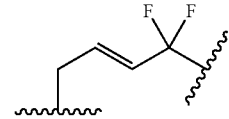 | 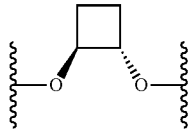 | 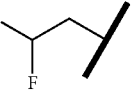 |
| 176. | 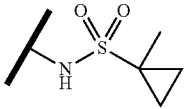 |  | 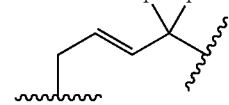 | 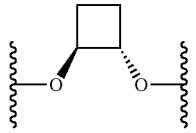 |  |
| 177. | 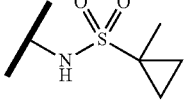 | 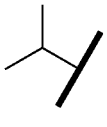 | 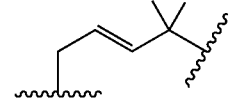 | 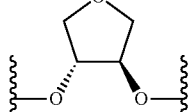 |  |
| 178. | 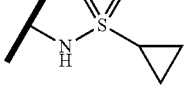 | 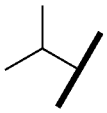 | 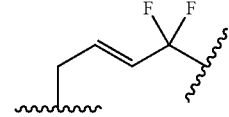 |  | 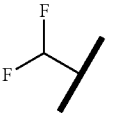 |
| 179. | 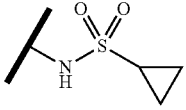 | 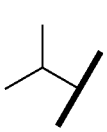 | 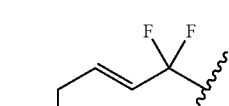 | 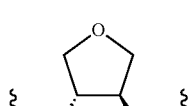 | 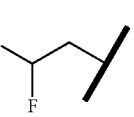 |
| 180. | 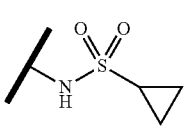 | 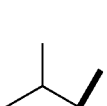 | 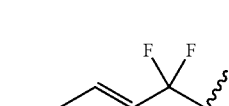 | 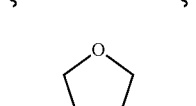 |  |
| 181. | 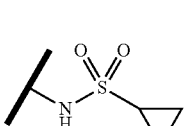 |  |  | 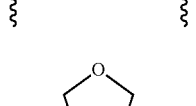 |  |

US 9,220,748 B2

TABLE 1-continued

| Example # | R | —L₂—W—L₁— | ![B with M₁ and M₂] | R' | G |
|---|---|---|---|---|---|
| 182. | | | | | |
| 183. | | | | | |
| 184. | | | | | |
| 185. | | | | | |
| 186. | | | | | |
| 187. | | | | | |
| 188. | | | | | |
| 189. | | | | | |

TABLE 1-continued
| Example # | R | —L₂—W—L₁— | ⌇⌇⌇M₁—B—M₂⌇⌇⌇ | R' | G |
|---|---|---|---|---|---|
| 190. | 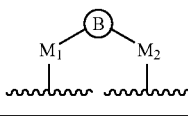 |  | 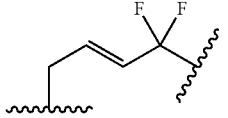 | 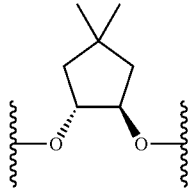 | 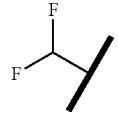 |
| 191. | 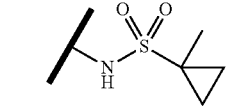 |  | 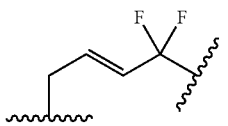 | 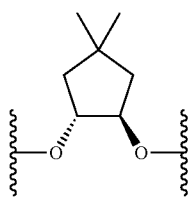 | 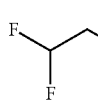 |
| 192. | 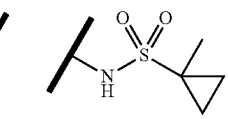 |  | 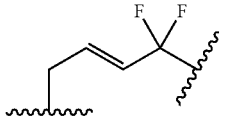 | 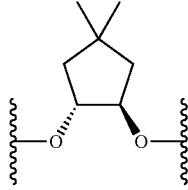 |  |
| 193. | 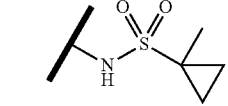 |  | 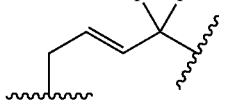 | 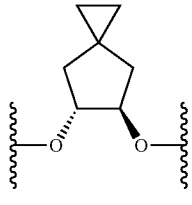 | 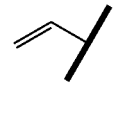 |
| 194. | 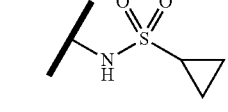 |  | 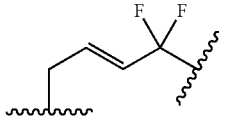 | 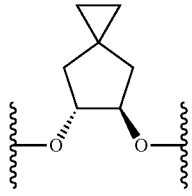 | 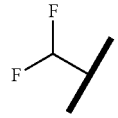 |
| 195. | 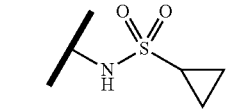 |  | 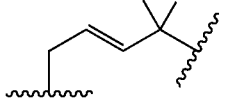 | 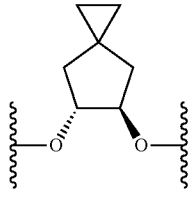 | 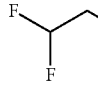 |
| 196. | 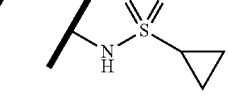 | 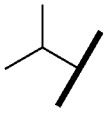 | 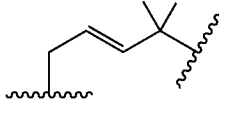 | 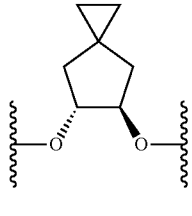 |  |

TABLE 1-continued
| Example # | R | —L₂—W—L₁— |  | R' | G |
|---|---|---|---|---|---|
| 197. | 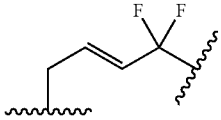 | 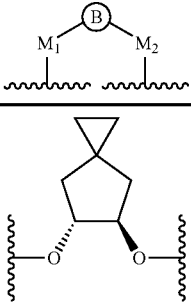 | 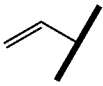 | 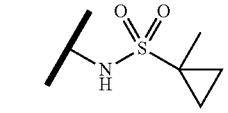 |  |
| 198. | 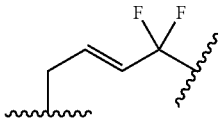 | 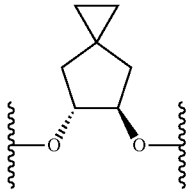 | 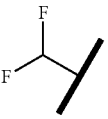 | 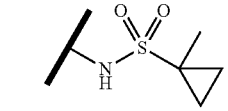 |  |
| 199. | 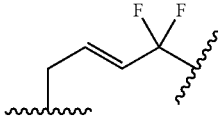 | 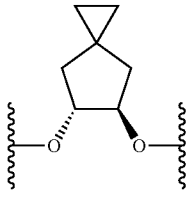 | 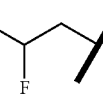 | 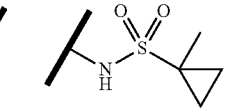 |  |
| 200. | 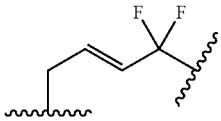 | 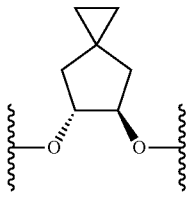 |  | 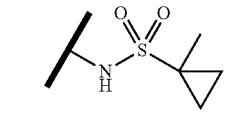 |  |
| 201. | 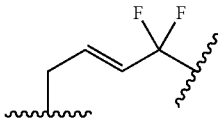 | 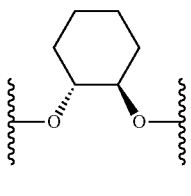 |  | 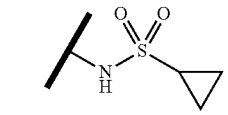 |  |
| 202. | 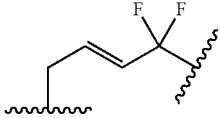 | 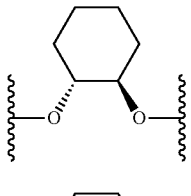 | 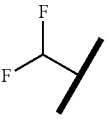 | 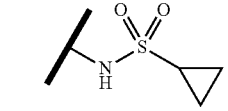 |  |
| 203. | 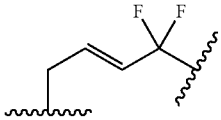 | 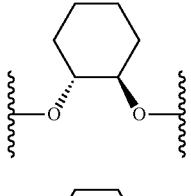 | 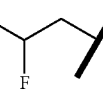 | 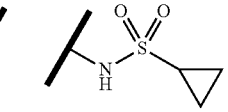 |  |
| 204. | 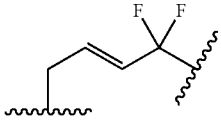 | 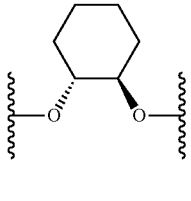 |  | 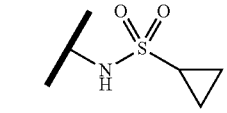 | |

TABLE 1-continued
| Example # | R | —L₂—W—L₁— | M₁ ⌢B⌢ M₂ | R' | G |
|---|---|---|---|---|---|
| 205. | 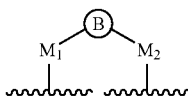 | 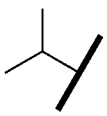 | 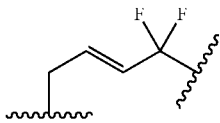 | 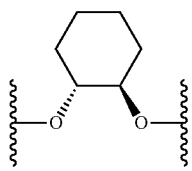 |  |
| 206. | 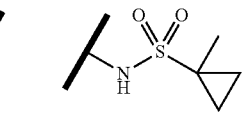 |  | 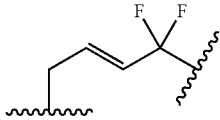 | 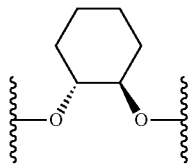 | 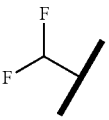 |
| 207. | 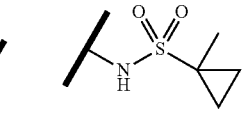 |  | 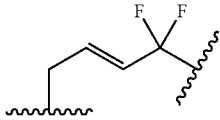 | 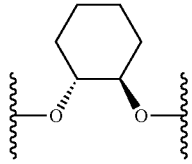 | 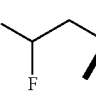 |
| 208. | 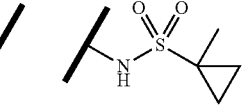 |  | 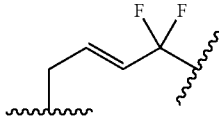 | 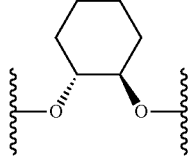 |  |
| 209. | 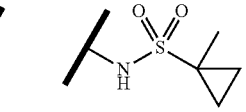 |  | 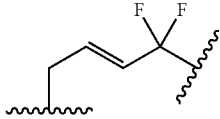 | 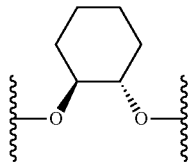 |  |
| 210. | 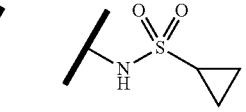 |  | 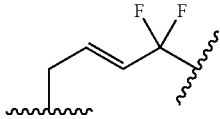 | 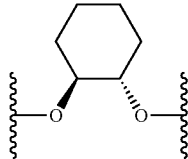 | 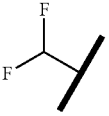 |
| 211. | 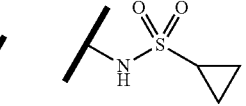 |  | 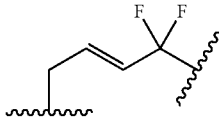 | 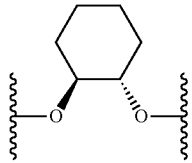 | 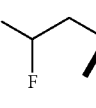 |
| 212. | 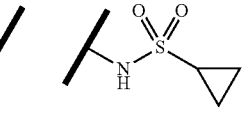 |  | 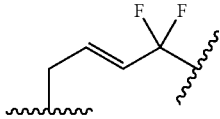 | 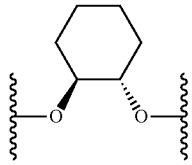 |  |

US 9,220,748 B2

TABLE 1-continued

| Example # | R | —L₂—W—L₁— | M₁ —B— M₂ | R' | G |
|---|---|---|---|---|---|
| 213. | | | | | |
| 214. | | | | | |
| 215. | | | | | |
| 216. | | | | | |
| 217. | | | | | |
| 218. | | | | | |
| 219. | | | | | |
| 220. | | | | | |

TABLE 1-continued
| Example # | R | —L₂—W—L₁— | 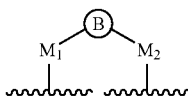 | R' | G |
|---|---|---|---|---|---|
| 221. |  | 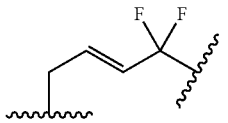 | 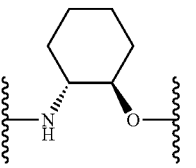 |  | 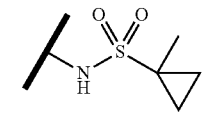 |
| 222. |  | 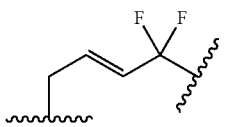 | 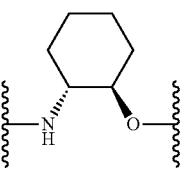 | 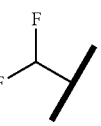 | 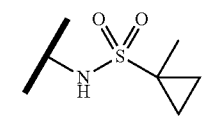 |
| 223. |  | 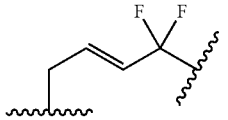 | 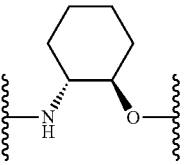 | 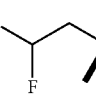 | 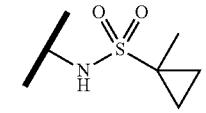 |
| 224. |  | 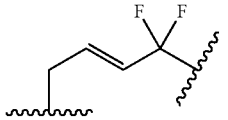 | 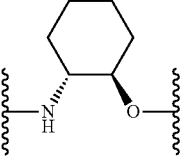 |  | 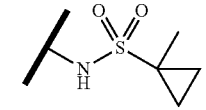 |
| 225. |  | 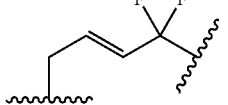 | 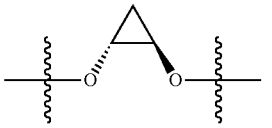 |  | 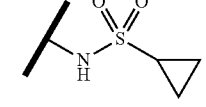 |
| 226. |  | 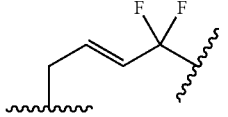 | 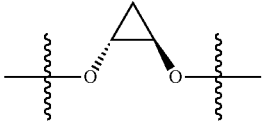 | 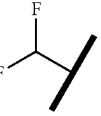 | 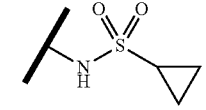 |
| 227. |  | 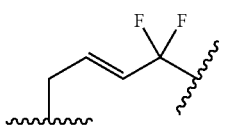 | 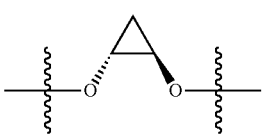 | 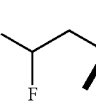 | 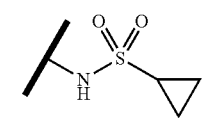 |
| 228. |  | 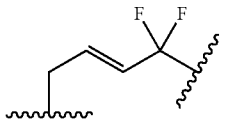 | 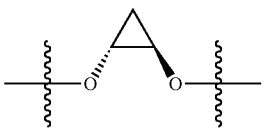 |  | 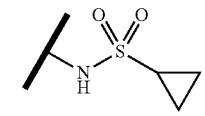 |
| 229. |  | 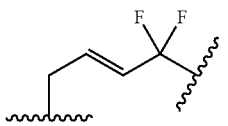 | 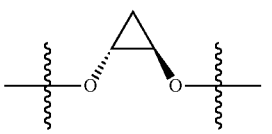 |  | 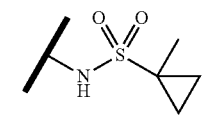 |

TABLE 1-continued
| Example # | R | —L₂—W—L₁— | $\overset{\overset{\displaystyle B}{\frown}}{M_1 \qquad M_2}$ | R' | G |
|---|---|---|---|---|---|
| 230. | 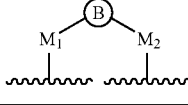 |  | 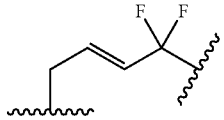 | 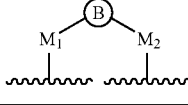 | 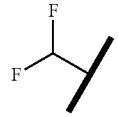 |
| 231. | 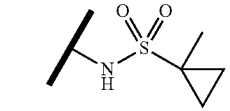 |  | 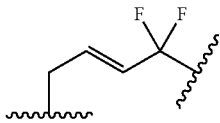 | 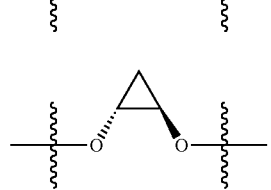 | 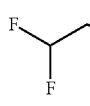 |
| 232. | 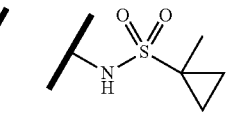 |  | 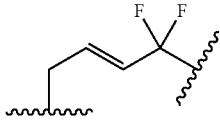 | 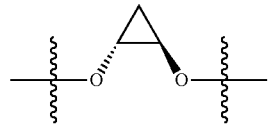 | 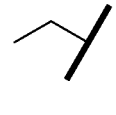 |
| 233. | 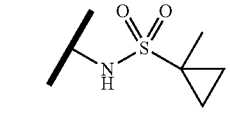 |  | 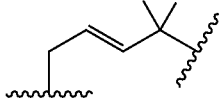 | 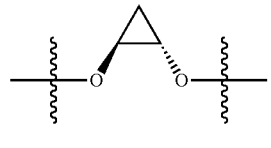 |  |
| 234. | 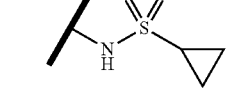 |  | 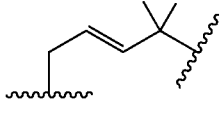 | 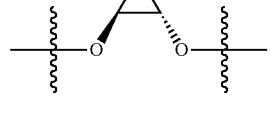 | 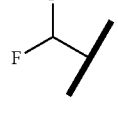 |
| 235. | 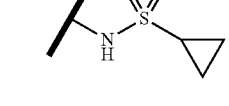 |  | 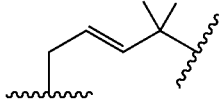 | 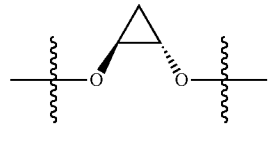 | 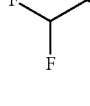 |
| 236. | 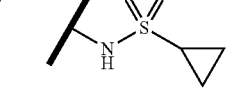 |  | 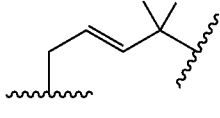 | 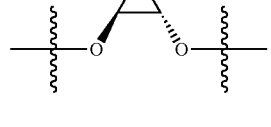 |  |
| 237. | 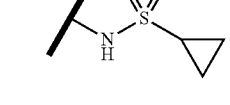 |  | 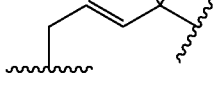 | 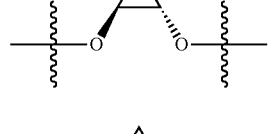 |  |
| 238. | 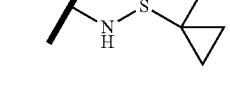 |  | 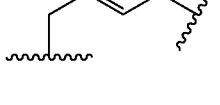 | 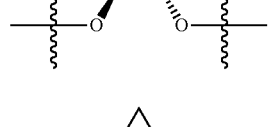 | 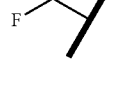 |
| 239. | 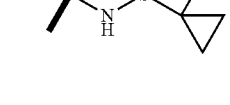 |  | 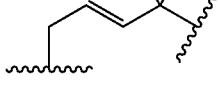 | 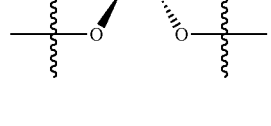 | 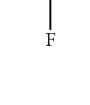 |

TABLE 1-continued

| Example # | R | —L₂—W—L₁— | M₁ B M₂ | R' | G |
|---|---|---|---|---|---|
| 240. | | | | | |
| 241. | | | | | |
| 242. | | | | | |
| 243. | | | | | |
| 244. | | | | | |
| 245. | | | | | |
| 246. | | | | | |
| 247. | | | | | |
| 248. | | | | | |

TABLE 1-continued
| Example # | R | —L₂—W—L₁— | 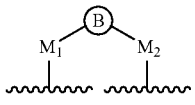 | R' | G |
|---|---|---|---|---|---|
| 249. | | | | | |
| 250. | | | | | |
| 251. | | | | | |
| 252. | | | | | |
| 253. | | | | | |
| 254. | | | | | |
| 255. | | | | | |
| 256. | | | | | |

Representative compounds of the invention also include, but are not limited to, the following compounds (example 257 to example 264 in Table 2) according to Formula IX wherein R, -L$_2$-W-L$_1$-,
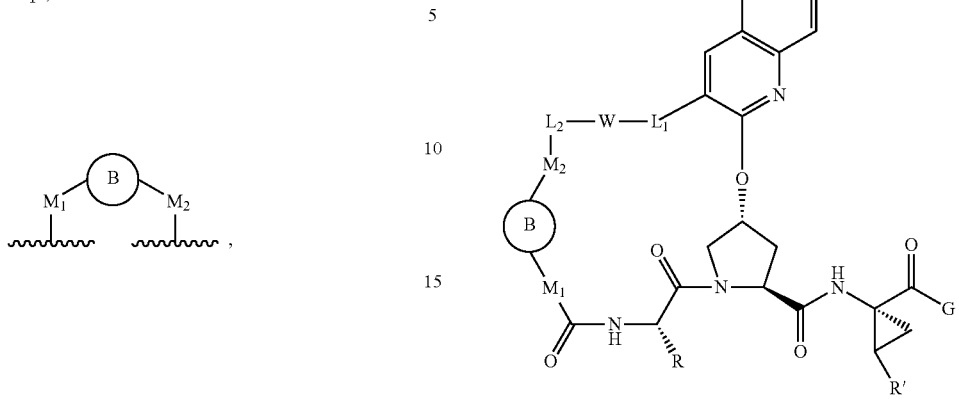
R' and G are delineated for each example in Table 2.
TABLE 2
| Example # | R | —L$_2$—W—L$_1$— | M$_1$—B—M$_2$ | R' | G |
|---|---|---|---|---|---|
| 257. | | | | | |
| 258. | | | | | |
| 259. | | | | | |
| 260. | | | | | |
| 261. | | | | | |

TABLE 2-continued
| Example # | R | —L₂—W—L₁— | M₁ ⌒B⌒ M₂ | R' | G |
|---|---|---|---|---|---|
| 262. | | | | | |
| 263. | | | | | |
| 264. | | | | | |
Representative compounds of the invention also include, but are not limited to, the following compounds (example 265 to example 272 in Table 3) according to Formula X wherein R, -L₂-W-L₁-,
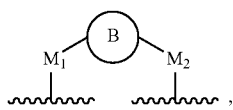,
R' and G are delineated for each example in Table 3.
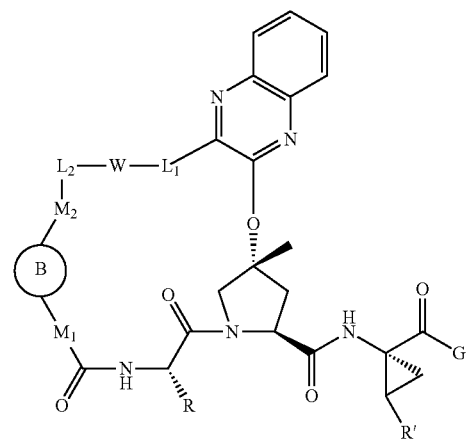
(X)
TABLE 3
| Example # | R | —L₂—W—L₁— | M₁ ⌒B⌒ M₂ | R' | G |
|---|---|---|---|---|---|
| 265. | | | | | |

TABLE 3-continued

| Example # | R | —L₂—W—L₁— | M₁ ⌢B⌢ M₂ | R' | G |
|---|---|---|---|---|---|
| 266. | | | | | |
| 267. | | | | | |
| 268. | | | | | |
| 269. | | | | | |
| 270. | | | | | |
| 271. | | | | | |
| 272. | | | | | |

In addition, representative compounds of the invention also include, but are not limited to, the following compounds (example 273 to example 299 in Table 4) according to Formula XI, wherein R,

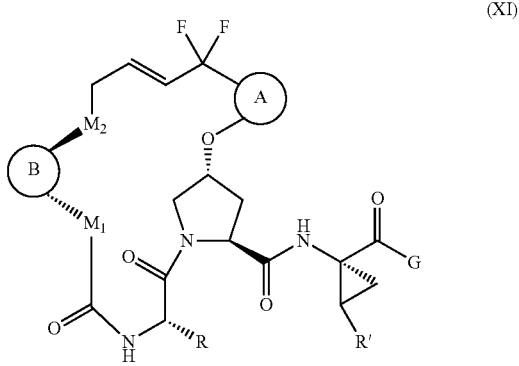

(XI)

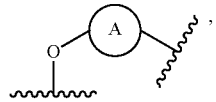

R' and G are delineated for each example in Table 4.

TABLE 4

| Example # | R | B(M₁)(M₂) | O-A | R' | G |
|---|---|---|---|---|---|
| 273. | t-Bu-CH₂ | (1R,2S)-cyclopentane-1,2-diyl bis-O | 3-oxy-6-OCF₃-quinoxalin-2-yl | CHF₂-CH₂ | N(H)SO₂-(1-methylcyclopropyl) |
| 274. | t-Bu-CH₂ | (1R,2S)-cyclopentane-1,2-diyl bis-O | 3-oxy-6-OCF₃-quinoxalin-2-yl | CH₂=CH- | N(H)SO₂-(1-methylcyclopropyl) |
| 275. | t-Bu-CH₂ | (1R,2S)-cyclopentane-1,2-diyl bis-O | 2-oxy-6-OCF₃-quinoxalin-3-yl | CHF₂-CH₂ | N(H)SO₂-(1-methylcyclopropyl) |
| 276. | t-Bu-CH₂ | (1R,2S)-cyclopentane-1,2-diyl bis-O | 2-oxy-6-OCF₃-quinoxalin-3-yl | CH₂=CH- | N(H)SO₂-(1-methylcyclopropyl) |
| 277. | t-Bu-CH₂ | (1R,2S)-cyclopentane-1,2-diyl bis-O | 3-oxy-6-OMe-quinoxalin-2-yl | Et | N(H)SO₂-cyclopropyl |

TABLE 4-continued

| Example # | R | B, M₁, M₂ | A | R' | G |
|---|---|---|---|---|---|
| 278. | t-Bu | (1S,2S)-cyclopentane-1,2-diyl-O,O | 3-quinoxalinyl-6-OMe-O | allyl | NHS(O)₂-cyclopropyl |
| 279. | t-Bu | (1S,2S)-cyclopentane-1,2-diyl-O,O | 3-quinoxalinyl-6-OMe-O | CHF₂CH₂- | NHS(O)₂-cyclopropyl |
| 280. | t-Bu | (1S,2S)-cyclopentane-1,2-diyl-O,O | 3-quinoxalinyl-6-OMe-O | ethyl | NHS(O)₂-C(Me)(cyclopropyl) |
| 281. | t-Bu | (1S,2S)-cyclopentane-1,2-diyl-O,O | 3-quinoxalinyl-6-OMe-O | allyl | NHS(O)₂-C(Me)(cyclopropyl) |
| 282. | t-Bu | (1S,2S)-cyclopentane-1,2-diyl-O,O | 3-quinoxalinyl-6-OMe-O | CHF₂CH₂- | NHS(O)₂-C(Me)(cyclopropyl) |
| 283. | t-Bu | (1S,2S)-cyclopentane-1,2-diyl-O,O | 3-quinoxalinyl-6-CF₃-O | CHF₂CH₂- | NHS(O)₂-cyclopropyl |
| 284. | t-Bu | (1S,2S)-cyclopentane-1,2-diyl-O,O | 3-quinoxalinyl-6-CF₃-O | allyl | NHS(O)₂-C(Me)(cyclopropyl) |
| 285. | t-Bu | (1S,2S)-cyclopentane-1,2-diyl-O,O | 3-quinoxalinyl-6-CF₃-O | CHF₂CH₂- | NHS(O)₂-cyclopropyl |

TABLE 4-continued
| Example # | R | B M₁ M₂ | O A | R' | G |
|---|---|---|---|---|---|
| 286. | 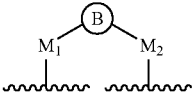 | 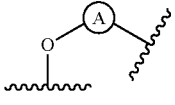 |  | 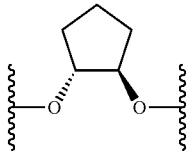 | 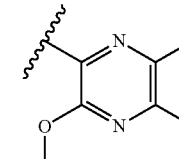 |
| 287. |  | 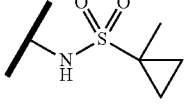 |  | 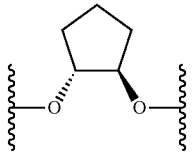 | 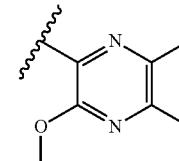 |
| 288. |  | 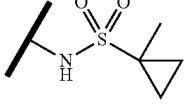 |  | 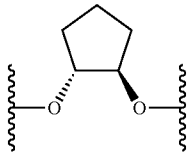 | 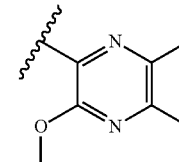 |
| 289. | 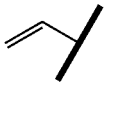 | 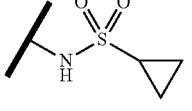 |  | 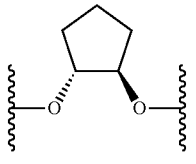 | 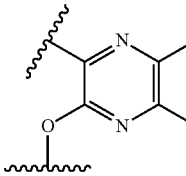 |
| 290. | 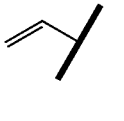 | 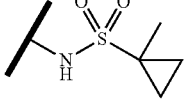 |  | 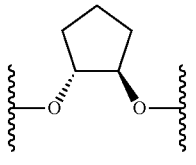 | 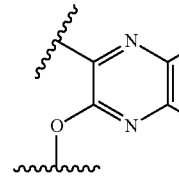 |
| 291. | 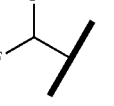 | 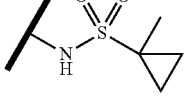 |  | 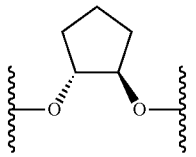 | 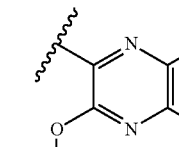 |
| 292. |  | 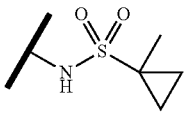 |  | 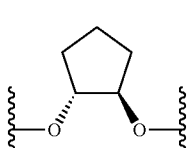 | 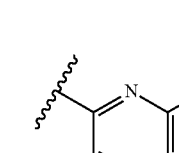 |

TABLE 4-continued

The present invention also features pharmaceutical compositions comprising a compound of the invention, or a pharmaceutically acceptable salt, ester or prodrug thereof. In one embodiment, the present invention features pharmaceutical compositions comprising a therapeutically effective amount of a compound of the invention, or a pharmaceutically acceptable salt, ester or prodrug thereof, in combination with a pharmaceutically acceptable carrier or excipient. In another embodiment, the invention features methods of treating a hepatitis C infection in a subject in need of such treatment with said pharmaceutical composition.

In addition, the present invention features methods of using compounds of the present invention or pharmaceutically acceptable salts thereof to treat HCV infection. The methods comprise administering to an HCV patient in need thereof an effective amount of a compound of the invention or a pharmaceutically acceptable salt thereof.

Preferably, the compound is a compound having Formula VII as described above.

It was unexpectedly discovered that the compounds of the invention can significantly inhibit or suppress certain HCV genotype 1 and 3 variants (e.g., genotype 1a R155K, D168E or D168V variants, genotype 1b R155K or D168V variants, or genotype 3a S138T, A166T or Q168R variants). Clinical trials and replicon cell assays have identified HCV variants that are resistant to many known protease inhibitors. For instance, the R155K variants have been shown to confer low-level resistance to telaprevir and boceprevir and confer high-level resistance to BILN 2061 and danoprevir (ITMN-191). See Bartels et al., THE JOURNAL OF INFECTIOUS DISEASES 198:800-807 (2008). See also Lu et al., ANTIMICROBIAL AGENTS AND CHEMOTHERAPY, 48:2260-2266 (2004); and Zhou et al., THE JOURNAL OF BIOLOGICAL CHEMISTRY, 282:22619-22628 (2007). Viral load rebound, which often indicates treatment failure, has been observed in patients receiving treatment with danoprevir after the R155K variants emerge. See www.natap.org/2010/AASLD/AASLD_84.htm (61th Annual Meeting of the American Association for the Study of Liver Diseases, Boston, Mass., Oct. 30-Nov. 3, 2010). Likewise, viral load rebound has been reported in patients receiving treatment with vaniprevir (MK-7009). R155K or D168V variants have been detected in these patients, suggesting resistance or reduced susceptibility of these variants to vaniprevir. See www.natap.org/2009/EASL/EASL_27.htm (EASL 44th Annual Meeting, April 2009, Copenhagen, Denmark). Moreover, HCV variants harboring R155K have been detected as the predominant quasispecies in some treatment-naïve patients. See Salloum et al., ANTIVIRAL RESEARCH 87:272-275 (2010). Accordingly, with significantly improved inhibitory activities against wild-type as well as variants, the compounds of the present invention enable an effective and broad-spectrum treatment for HCV infections.

In one aspect, the present invention features methods of treating HCV variants. The methods comprise administering to patients infected with or harboring such variants an effective amount of a compound of the invention or a pharmaceutically acceptable salt thereof. These patients can be treatment-naïve patients or treatment-experienced patients. In one embodiment, the patient receiving treatment according to this aspect of the invention harbors a variant selected from genotype 1a R155K, D168E or D168V variants, genotype 1b R155K or D168V variants, or genotype 3a A166T or Q168R variants. In another embodiment, the patient harbors an HCV variant selected from genotype 1 R155K or D168V variants or genotype 3 Q168R variants. For example, the patient can harbor a variant selected from genotype 1a R155K or D168V variants, genotype 1b R155K or D168V variants, or genotype 3s Q168R variants. In yet another embodiment, the patient harbors a variant selected from genotype 1 R155K or D168V variants, e.g., genotype 1a R155K or D168V variants or genotype 1b R155K or D168V variants. In one example, the patient harbors a genotype 1 R155K variant (e.g., a genotype 1a or 1b R155K variant). In another example, the patient harbors a genotype 1 D168V variant (e.g., a genotype 1a or 1b D168V variant).

The patients treated according to this aspect of the invention may have previously received but failed a treatment regimen containing another HCV protease inhibitor. The other HCV protease inhibitor(s) used in the prior treatment can be selected from, for example and without limitation, telaprevir, boceprevir, danoprevir, vaniprevir, narlaprevir, TMC-435 (Tibotec), BILN 2061 (Boehringer Ingelheim), BI-201335 (Boehringer Ingelheim), BMS-650032 (BMS), or a combination thereof.

Preferably, the compound employed in this aspect of the invention is a compound having Formula VII as described above or a pharmaceutically acceptable salt thereof. More preferably, the compound employed in this aspect of the invention is selected from compounds of Examples 1, 2, 4, 5, 6, 8, 34, 36, 40, 65, 89, 90, 273, 274, 275, 276, 277, 278, 279, 280, 281, 282, 283, 284, 285, 286, 287, 288, 289, 290, 291, 292, 293, 294, 295, 296, or 297, or pharmaceutically acceptable salts thereof. Highly preferably, the compound employed in this aspect of the invention is selected from compounds of Examples 5, 6, 275, 276, 287, 288, 289, 294, 296 or 297, or pharmaceutically acceptable salts thereof.

In another aspect, the present invention features methods of treating HCV patients who have previously received a treatment regimen containing another HCV protease inhibitor. The methods comprise administering to said patients an effective amount of a compound of the invention or a pharmaceutically acceptable salt thereof. Without limiting the present invention to any particular theory, these treatment-experienced patients may harbor resistant variants or be prone to HCV mutations and, as a result, be less responsive to other protease inhibitors (e.g., telaprevir, boceprevir, danoprevir, vaniprevir, narlaprevir, TMC-435 (Tibotec), BILN 2061 (Boehringer Ingelheim), BI-201335 (Boehringer Ingelheim), BMS-650032 (BMS), or a combination thereof). Preferably, the compound employed in this aspect of the invention is a compound having Formula VII as described above or a pharmaceutically acceptable salt thereof. More preferably, the compound employed in this aspect of the invention is selected from compounds of Examples 1, 2, 4, 5, 6, 8, 34, 36, 40, 65, 89, 90, 273, 274, 275, 276, 277, 278, 279, 280, 281, 282, 283, 284, 285, 286, 287, 288, 289, 290, 291, 292, 293, 294, 295, 296, 297, 298 or 299, or pharmaceutically acceptable salts thereof. Highly preferably, the compound employed in this aspect of the invention can be selected from compounds of Examples 5, 6, 275, 276, 287, 288, 289, 294, 296 or 297, or pharmaceutically acceptable salts thereof.

Moreover, the present invention features methods of treating HCV patients infected with genotype 3 HCV viruses. These methods are based on the unexpected finding that the compounds of the invention are effective in inhibiting HCV genotype 3 viruses including certain variants (e.g., A166T, Q168R or S138T variants). These methods comprise administering to said patients an effective amount of a compound of the invention or a pharmaceutically acceptable salt thereof. Preferably, the compound employed in this aspect of the invention is a compound having Formula VII as described above or a pharmaceutically acceptable salt thereof. More preferably, the compound employed in this aspect of the invention is selected from compounds of Examples 1, 2, 4, 5, 6, 8, 34, 36, 40, 65, 89, 90, 273, 274, 275, 276, 277, 278, 279, 280, 281, 282, 283, 284, 285, 286, 287, 288, 289, 290, 291, 292, 293, 294, 295, 296, 297, 298 or 299, or pharmaceutically acceptable salts thereof. Highly preferably, the compound employed in this aspect of the invention can be selected from compounds of Examples 5, 6, 275, 276, 287, 288, 289, 294, 296 or 297, or pharmaceutically acceptable salts thereof.

The present invention also features the use of a compound of the invention, or a pharmaceutically acceptable salt thereof, for the manufacture of a medication for the treatment of HCV variants. For instance, the patients being treated may be infected with or harbor a variant selected from genotype 1a R155K, D168E or D168V variants, genotype 1b R155K or D168V variants, or genotype 3a A166T or Q168R variants. In addition, the present invention features the use of a compound of the invention, or a pharmaceutically acceptable salt thereof, for the manufacture of a medication for the treatment of treatment-experienced HCV patients who have previously received but failed a treatment containing another HCV protease inhibitor (e.g., telaprevir, boceprevir, danoprevir, vaniprevir, narlaprevir, TMC-435 (Tibotec), BILN 2061 (Boehringer Ingelheim), BI-201335 (Boehringer Ingelheim), BMS-650032 (BMS), or a combination thereof). Furthermore, the present invention contemplates the use of a compound of the invention, or a pharmaceutically acceptable salt thereof, for the manufacture of a medication for the treatment of HCV patients infected with genotype 3 HCV (including genotype 3 variants, such as genotype 3s A166T, Q168R or S138T variants).

In the methods described herein, a compound of the present invention or a pharmaceutically acceptable salt thereof can be administered alone, or in combination with one or more other anti-HCV agents, such as HCV polymerase inhibitors, HCV protease inhibitors, HCV NS5A inhibitors, CD81 inhibitors, cyclophilin inhibitors, internal ribosome entry site (IRES) inhibitors or any combinations thereof. Interferon, ribavirin or both can also be included in the treatment. For example, the methods described herein can further comprise administering to the patient peginterferon-alpha and ribavirin. Different agents can be administered simultaneously or sequentially. The dosing frequency of each agent in a treatment regimen can be the same or different. For instance, a compound of the invention can be dosed once daily and ribavirin can be dosed twice daily.

Compounds of the present invention can be administered as the sole active pharmaceutical agent, or used in combination with one or more agents to treat or prevent hepatitis C infections or the symptoms associated with HCV infection. Other agents to be administered in combination with a compound or combination of compounds of the invention include therapies for disease caused by HCV infection that suppresses HCV viral replication by direct or indirect mechanisms. These include agents such as host immune modulators (for example, interferon-alpha, pegylated interferon-alpha, interferon-beta, interferon-gamma, CpG oligonucleotides and the like), cyclophilins (e.g., Debio 025), or antiviral compounds that inhibit host cellular functions such as inosine monophosphate dehydrogenase (for example, ribavirin and the like). Also included are cytokines that modulate immune function. Also included are vaccines comprising HCV antigens or antigen adjuvant combinations directed against HCV. Also included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like. Other agents to be administered in combination with a compound of the present invention include any agent or combination of agents that inhibit the replication of HCV by targeting proteins of the viral genome involved in the viral replication. These agents include but are not limited to other inhibitors of HCV RNA dependent RNA polymerase such as, for example, nucleoside type polymerase inhibitors described in WO0190121(A2), or U.S. Pat. No. 6,348,587B1 or WO0160315 or WO0132153 or non-nucleoside inhibitors such as, for example, benzimidazole polymerase inhibitors described in EP 1162196A1 or WO0204425 or inhibitors of HCV protease such as, for example, peptidomimetic type inhibitors such as BILN2061 and the like or inhibitors of HCV helicase.

Other agents to be administered in combination with a compound of the present invention include any agent or combination of agents that inhibit the replication of other viruses for co-infected individuals. These agents include but are not limited to therapies for disease caused by hepatitis B (HBV) infection or therapies for disease caused by human immunodeficiency virus (HIV) infection.

Accordingly, one aspect of the invention is directed to a method for treating or preventing an infection caused by an RNA-containing virus comprising co-administering to a patient in need of such treatment one or more agents selected from the group consisting of a host immune modulator and a second antiviral agent, or a combination thereof, with a therapeutically effective amount of a compound or combination of compounds of the invention, or a pharmaceutically acceptable salt, stereoisomer, tautomer, prodrug, salt of a prodrug, or combination thereof. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

A further aspect of the invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the invention, or a pharmaceutically acceptable salt, stereoisomer, tautomer, prodrug, salt of a prodrug, or combination thereof. Yet another aspect of the invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the invention, or a pharmaceutically acceptable salt, stereoisomer, tautomer, prodrug, salt of a prodrug, or combination thereof. An agent that treats patients for disease caused by hepatitis B (HBV) infection may be for example, but not limited thereto, L-deoxythymidine, adefovir, lamivudine or tenofovir, or any combination thereof. Example of the RNA-containing virus includes, but not limited to, hepatitis C virus (HCV).

Another aspect of the invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the invention, or a pharmaceutically acceptable salt, stereoisomer, tautomer, prodrug, salt of a prodrug, or combination thereof. An example of the RNA-containing virus includes, but not limited to, hepatitis C virus (HCV). In addition, the present invention provides the use of a compound or a combination of compounds of the invention, or a therapeutically acceptable salt form, stereoisomer, or tautomer, prodrug, salt of a prodrug, or combination thereof, and one or more agents selected from the group consisting of a host immune modulator and a second antiviral agent, or a combination thereof, to prepare a medicament for the treatment of an infection caused by an RNA-containing virus in a patient, particularly hepatitis C virus. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

When used in the above or other treatments, combination of compound or compounds of the invention, together with one or more agents as defined herein above, can be employed in pure form or, where such forms exist, in pharmaceutically acceptable salt form, prodrug, salt of a prodrug, or combination thereof. Alternatively, such combination of therapeutic agents can be administered as a pharmaceutical composition containing a therapeutically effective amount of the compound or combination of compounds of interest, or their pharmaceutically acceptable salt form, prodrugs, or salts of the prodrug, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, further aspect of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt, stereoisomer, or tautomer, prodrug, salt of a prodrug, or combination thereof, one or more agents as defined hereinabove, and a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including but not limited to, agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other anti-HCV agents include those agents that are effective for diminishing or preventing the progression of hepatitis C related symptoms or disease. Such agents include but are not limited to immunomodulatory agents, inhibitors of HCV NS3 protease, other inhibitors of HCV polymerase, inhibitors of another target in the HCV life cycle and other anti-HCV agents, including but not limited to, ribavirin, amantadine, levovirin and viramidine.

Immunomodulatory agents include those agents (compounds or biologicals) that are effective to enhance or potentiate the immune system response in a mammal. Immunomodulatory agents include, but are not limited to, inosine monophosphate dehydrogenase inhibitors such as VX-497 (merimepodib, Vertex Pharmaceuticals), class I interferons, class II interferons, consensus interferons, asialo-interferons pegylated interferons and conjugated interferons, including but not limited to, interferons conjugated with other proteins including but not limited to, human albumin. Class I interferons are a group of interferons that all bind to receptor type I, including both naturally and synthetically produced class I interferons, while class II interferons all bind to receptor type II. Examples of class I interferons include, but are not limited to, [alpha]-, [beta]-, [delta]-, [omega]-, and [tau]-interferons, while examples of class II interferons include, but are not limited to, [gamma]-interferons.

Inhibitors of HCV NS3 protease include agents (compounds or biologicals) that are effective to inhibit the function of HCV NS3 protease in a mammal Inhibitors of HCV NS3 protease include, but are not limited to, those compounds described in WO 99/07733, WO 99/07734, WO 00/09558, WO 00/09543, WO 00/59929, WO 03/064416, WO 03/064455, WO 03/064456, WO 2004/030670, WO 2004/037855, WO 2004/039833, WO 2004/101602, WO 2004/101605, WO 2004/103996, WO 2005/028501, WO 2005/070955, WO 2006/000085, WO 2006/007700 and WO 2006/007708 (all by Boehringer Ingelheim), WO 02/060926, WO 03/053349, WO03/099274, WO 03/099316, WO 2004/032827, WO 2004/043339, WO 2004/094452, WO 2005/046712, WO 2005/051410, WO 2005/054430 (all by BMS), WO 2004/072243, WO 2004/093798, WO 2004/113365, WO 2005/010029 (all by Enanta), WO 2005/037214 (Intermune) and WO 2005/051980 (Schering), and the candidates identified as VX-950, ITMN-191 and SCH 503034.

Inhibitors of HCV polymerase include agents (compounds or biologicals) that are effective to inhibit the function of an HCV polymerase. Such inhibitors include, but are not limited to, non-nucleoside and nucleoside inhibitors of HCV NS5B polymerase. Examples of inhibitors of HCV polymerase include but are not limited to those compounds described in: WO 02/04425, WO 03/007945, WO 03/010140, WO 03/010141, WO 2004/064925, WO 2004/065367, WO 2005/080388 and WO 2006/007693 (all by Boehringer Ingelheim), WO 2005/049622 (Japan Tobacco), WO 2005/014543 (Japan Tobacco), WO 2005/012288 (Genelabs), WO 2004/087714 (IRBM), WO 03/101993 (Neogenesis), WO 03/026587 (BMS), WO 03/000254 (Japan Tobacco), and WO 01/47883 (Japan Tobacco), and the clinical candidates XTL-2125, HCV 796, R-1626 and NM 283.

Inhibitors of another target in the HCV life cycle include agents (compounds or biologicals) that are effective to inhibit the formation and/or replication of HCV other than by inhibiting the function of the HCV NS3 protease. Such agents may interfere with either host or HCV viral mechanisms necessary for the formation and/or replication of HCV. Inhibitors of another target in the HCV life cycle include, but are not limited to, entry inhibitors, agents that inhibit a target selected from a helicase, a NS2/3 protease and an internal ribosome entry site (IRES) and agents that interfere with the function of other viral targets including but not limited to, an NS5A protein and an NS4B protein.

It can occur that a patient may be co-infected with hepatitis C virus and one or more other viruses, including but not limited to, human immunodeficiency virus (HIV), hepatitis A virus (HAV) and hepatitis B virus (HBV). Thus also contemplated is combination therapy to treat such co-infections by co-administering a compound according to the present invention with at least one of an HIV inhibitor, an HAV inhibitor and an HBV inhibitor.

According to yet another embodiment, the pharmaceutical compositions of the present invention may further comprise inhibitor(s) of other targets in the HCV life cycle, including, but not limited to, helicase, polymerase, metalloprotease, and internal ribosome entry site (IRES).

According to another embodiment, the pharmaceutical compositions of the present invention may further comprise another anti-viral, anti-bacterial, anti-fungal or anti-cancer agent, or an immune modulator, or another therapeutic agent.

According to still another embodiment, the present invention includes methods of treating viral infection such as, but not limited to, hepatitis C infections in a subject in need of such treatment by administering to said subject an effective amount of a compound of the present invention or a pharmaceutically acceptable salt, ester, or prodrug thereof.

According to a further embodiment, the present invention includes methods of treating hepatitis C infections in a subject in need of such treatment by administering to said subject an anti-HCV virally effective amount or an inhibitory amount of a pharmaceutical composition of the present invention.

An additional embodiment of the present invention includes methods of treating biological samples by contacting the biological samples with the compounds of the present invention.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "viral infection" refers to the introduction of a virus into cells or tissues, e.g., hepatitis C virus (HCV). In general, the introduction of a virus is also associated with replication. Viral infection may be determined by measuring virus antibody titer in samples of a biological fluid, such as blood, using, e.g., enzyme immunoassay. Other suitable diagnostic methods include molecular based techniques, such as RT-PCR, direct hybrid capture assay, nucleic acid sequence based amplification, and the like. A virus may infect an organ, e.g., liver, and cause disease, e.g., hepatitis, cirrhosis, chronic liver disease and hepatocellular carcinoma.

The term "anti-cancer agent" refers to a compound or drug capable of preventing or inhibiting the advancement of cancer. Examples of such agents include cis-platin, actinomycin D, doxorubicin, vincristine, vinblastine, etoposide, amsacrine, mitoxantrone, tenipaside, taxol, colchicine, cyclosporin A, phenothiazines or thioxantheres.

The term "anti-fungal agent" shall used to describe a compound which may be used to treat a fungus infection other than 3-AP, 3-AMP or prodrugs of 3-AP and 3-AMP according to the present invention. Anti-fungal agents according to the present invention include, for example, terbinafine, fluconazole, itraconazole, posaconazole, clotrimazole, griseofulvin, nystatin, tolnaftate, caspofungin, amphotericin B, liposomal amphotericin B, and amphotericin B lipid complex.

The term "antibacterial agent" refers to both naturally occurring antibiotics produced by microorganisms to suppress the growth of other microorganisms, and agents synthesized or modified in the laboratory which have either bactericidal or bacteriostatic activity, e.g., β-lactam antibacterial agents, glycopeptides, macrolides, quinolones, tetracyclines, and aminoglycosides. In general, if an antibacterial agent is bacteriostatic, it means that the agent essentially stops bacterial cell growth (but does not kill the bacteria); if the agent is bacteriocidal, it means that the agent kills the bacterial cells (and may stop growth before killing the bacteria).

The term "immune modulator" refers to any substance meant to alter the working of the humoral or cellular immune system of a subject. Such immune modulators include inhibitors of mast cell-mediated inflammation, interferons, interleukins, prostaglandins, steroids, cortico-steroids, colony-stimulating factors, chemotactic factors, etc.

The term "$C_1$-$C_6$ alkyl," or "$C_1$-$C_8$ alkyl," as used herein, refer to saturated, straight- or branched-chain hydrocarbon radicals containing between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "$C_2$-$C_6$ alkenyl," or "$C_2$-$C_8$ alkenyl," as used herein, denote a monovalent group derived from a hydrocarbon moiety by the removal of a single hydrogen atom wherein the hydrocarbon moiety has at least one carbon-carbon double bond and contains from two to six, or two to eight carbon atoms, respectively. Alkenyl groups include, but are not limited to, for example, ethenyl, propenyl, butenyl, 1-methyl-2-buten-1-yl, heptenyl, octenyl and the like.

The term "$C_2$-$C_6$ alkynyl," or "$C_2$-$C_8$ alkynyl," as used herein, denote a monovalent group derived from a hydrocarbon moiety by the removal of a single hydrogen atom wherein the hydrocarbon moiety has at least one carbon-carbon triple bond and contains from two to six, or two to eight carbon atoms, respectively. Representative alkynyl groups include, but are not limited to, for example, ethynyl, 1-propynyl, 1-butynyl, heptynyl, octynyl and the like.

The term "carbocycle" refers to a saturated (e.g., "cycloalkyl"), partially saturated (e.g., "cycloalkenyl" or "cycloalkynyl") or completely unsaturated (e.g., "aryl") ring system containing zero heteroatom ring atom. "Ring atoms" or "ring members" are the atoms bound together to form the ring or rings. Where a carbocycle group is a divalent moiety linking two other elements in a depicted chemical structure (such as Z in Formula $I_A$), the carbocycle group can be attached to the two other elements through any two substitutable ring atoms. A $C_4$-$C_6$ carbocycle has 4-6 ring atoms.

The term "$C_3$-$C_8$-cycloalkyl", or "$C_3$-$C_{12}$-cycloalkyl," as used herein, denotes a monovalent group derived from a monocyclic or polycyclic saturated carbocyclic ring compound by the removal of a single hydrogen atom where the saturated carbocyclic ring compound has from 3 to 8, or from 3 to 12, ring atoms, respectively. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl.

The term "$C_3$-$C_8$-cycloalkenyl", or "$C_3$-$C_{12}$-cycloalkenyl" as used herein, denote a monovalent group derived from a monocyclic or polycyclic carbocyclic ring compound having at least one carbon-carbon double bond by the removal of a single hydrogen atom where the carbocyclic ring compound has from 3 to 8, or from 3 to 12, ring atoms, respectively. Examples of $C_3$-$C_8$-cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "arylalkyl," as used herein, refers to a $C_1$-$C_3$ alkyl or $C_1$-$C_6$ alkyl residue attached to an aryl ring. Examples include, but are not limited to, benzyl, phenethyl and the like.

The term "heteroaryl," as used herein, refers to a mono-, bi-, or tri-cyclic aromatic radical or ring having from five to ten ring atoms of which at least one ring atom is selected from S, O and N; wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroarylalkyl," as used herein, refers to a $C_1$-$C_3$ alkyl or $C_1$-$C_6$ alkyl residue residue attached to a heteroaryl ring. Examples include, but are not limited to, pyridinylmethyl, pyrimidinylethyl and the like.

The term "substituted" as used herein, refers to independent replacement of one, two, or three or more of the hydrogen atoms thereon with substituents including, but not limited to, —F, —Cl, —Br, —I, —OH, protected hydroxy, —$NO_2$, —CN, —$NH_2$, $N_3$, protected amino, alkoxy, thioalkoxy, oxo, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH—$C_1$-$C_{12}$-alkyl, —$SO_2$NH—$C_2$-$C_{12}$-alkenyl, —$SO_2$NH—$C_2$-$C_{12}$-alkynyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, methylthiomethyl, or -L'—R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —$NO_2$, —CN, or —$NH_2$.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

The term "heterocycloalkyl" and "heterocyclic" can be used interchangeably and refer to a non-aromatic 3-, 4-, 5-, 6- or 7-membered ring or a bi- or tri-cyclic group fused system, where: (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (v) any of the above rings may be fused to a benzene ring, and (vi) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted to give substituted heterocyclic.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, hetoerarylalkylene and heterocycloalkylene groups are to be included in the above definitions, and are applicable to provide the formulas herein with proper valency.

The term "hydroxy activating group", as used herein, refers to a labile chemical moiety which is known in the art to activate a hydroxy group so that it will depart during synthetic procedures such as in a substitution or elimination reactions. Examples of hydroxy activating group include, but not limited to, mesylate, tosylate, triflate, p-nitrobenzoate, phosphonate and the like.

The term "activated hydroxy", as used herein, refers to a hydroxy group activated with a hydroxy activating group, as defined above, including mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups.

The terms "halo" and "halogen," as used herein, refer to an atom selected from fluorine, chlorine, bromine and iodine.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient. As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G., S. M. Wuts, *Protective Groups in Organic Synthesis,* 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$). Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis*, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed). "Design and Application of Prodrugs, *Textbook of Drug Design and Development*, Chapter 5, 113-191 (1991); Bundgaard, et al., *Journal of Drug Deliver Reviews*, 8:1-38 (1992); Bundgaard, J. of *Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a subject such as a human or lower mammal by administering to the subject an anti-hepatitis C virally effective amount or an inhibitory amount of a compound of the present invention, in such amounts and for such time as is necessary to achieve the desired result. An additional method of the present invention is the treatment of biological samples with an inhibitory amount of a compound of composition of the present invention in such amounts and for such time as is necessary to achieve the desired result.

The term "anti-hepatitis C virally effective amount" of a compound of the invention, as used herein, mean a sufficient amount of the compound so as to decrease the viral load in a biological sample or in a subject (e.g., resulting in at least 10%, preferably at least 50%, more preferably at least 80%, and most preferably at least 90% or 95%, reduction in viral load). As well understood in the medical arts, an anti-hepatitis C virally effective amount of a compound of this invention will be at a reasonable benefit/risk ratio applicable to any medical treatment.

The term "inhibitory amount" of a compound of the present invention means a sufficient amount to decrease the hepatitis C viral load in a biological sample or a subject (e.g., resulting in at least 10%, preferably at least 50%, more preferably at least 80%, and most preferably at least 90% or 95%, reduction in viral load). It is understood that when said inhibitory amount of a compound of the present invention is administered to a subject it will be at a reasonable benefit/risk ratio applicable to any medical treatment as determined by a physician. The term "biological sample(s)," as used herein, means a substance of biological origin intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof; or stem cells. Thus, another embodiment of the present invention is a method of treating a biological sample by contacting said biological sample with an inhibitory amount of a compound or pharmaceutical composition of the present invention.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:

ACN for acetonitrile;
BME for 2-mercaptoethanol;
BOP for benzotriazol-1-yloxy-tris(dimethylamino)phosphonium hexafluorophosphate;
CDI for carbonyldiimidazole;
COD for cyclooctadiene;
DAST for diethylaminosulfur trifluoride;
DABCYL for 6-(N-4'-carboxy-4-(dimethylamino)azobenzene)-aminohexyl-1-O-(2-cyanoethyl)-(N,N-diisopropyl)-phosphoramidite;
DBU for 1,8-Diazabicycloundec-7-ene;
DCC for N,N'-dicyclohexylcarbodiimide;
DCM for dichloromethane;
DIAD for diisopropyl azodicarboxylate;
DIBAL-H for diisobutylaluminum hydride;
DIPEA for diisopropyl ethylamine;
DMAP for N,N-dimethylaminopyridine;
DME for ethylene glycol dimethyl ether;
DMEM for Dulbecco's Modified Eagles Media;
DMF for N,N-dimethyl formamide;
DMSO for dimethylsulfoxide;
DSC for N,N'-disuccinimidyl carbonate;
DUPHOS for

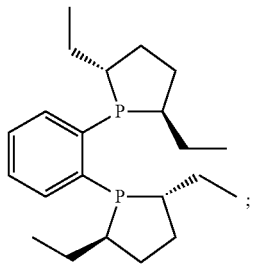

EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc for ethyl acetate;
EtOH for ethyl alcohol;
HATU for O(7-Azabenzotriazole-1-yl)-N,N,N',N'-tetramethyluronium hexafluorophosphate;
HCl for hydrochloric acid;
Hoveyda's Cat. for Dichloro(o-isopropoxyphenylmethylene) (tricyclohexylphosphine)ruthenium(II);
In for indium;
KHMDS is potassium bis(trimethylsilyl)amide;
Ms for mesyl;
NMM for N-4-methylmorpholine;
NMO for N-4-methylmorpholine-N-Oxide;
PyBrOP for Bromo-tri-pyrrolidino-phosphonium hexafluorophosphate;
Ph for phenyl;
RCM for ring-closing metathesis;
RT for reverse transcription;
RT-PCR for reverse transcription-polymerase chain reaction;
TBME for tert-butyl methyl ether;
TEA for triethyl amine;
TFA for trifluoroacetic acid;
THF for tetrahydrofuran;
TLC for thin layer chromatography;
TPAP tetrapropylammonium perruthenate;
TPP or $PPh_3$ for triphenylphosphine;
tBOC or Boc for tert-butyloxy carbonyl;
Xantphos for 4,5-Bis-diphenylphosphanyl-9,9-dimethyl-9H-xanthene; and
Zhan 1 B for

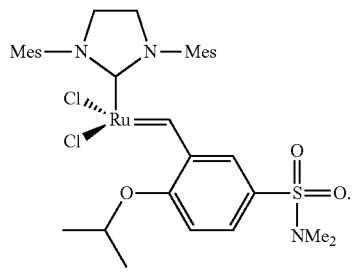

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

The preparation of quinoxalinyl macrocyclic compounds is exemplified in Scheme 1. The Boc group of quinoxaline derivative 1-1 (see Scheme 2 for preparation) was deprotected under acidic condition at room temperature (the acid can be selected from, but not limited to, HCl in dioxane or HCl in ethyl acetate or TFA. For further details on deprotection of Boc group see: T. W. Greene, *Protective Groups in Organic Synthesis*, Fourth Edition, John Wiley and Sons, 2006) to give the amine 1-2, which is coupled with acid 1-3 employing peptide coupling reagent (the coupling reagent can be selected from, but not limited to, HATU/DIPEA, DCC/DMAP, for further details on peptide coupling reagents see: Christian A. G. N. Montalbetti et al., *Tetrahedron* 2005, 61, 10827) to afford the diene 1-4. Ring-closing metathesis of diene 1-4 with a ruthenium-based catalyst gives the desired macrocyclic alkene 1-5 (for further details on ring-closing metathesis see recent reviews: Grubbs et al., *Acc. Chem. Res.*, 1995, 28, 446; Shrock et al., *Tetrahedron* 1999, 55, 8141; Furstner, A. *Angew. Chem. Int. Ed.* 2000, 39, 3012; Trnka et al., *Acc. Chem. Res.* 2001, 34, 18, and Hoveyda et al., *Chem. Eur. J.* 2001, 7, 945).

Scheme 1

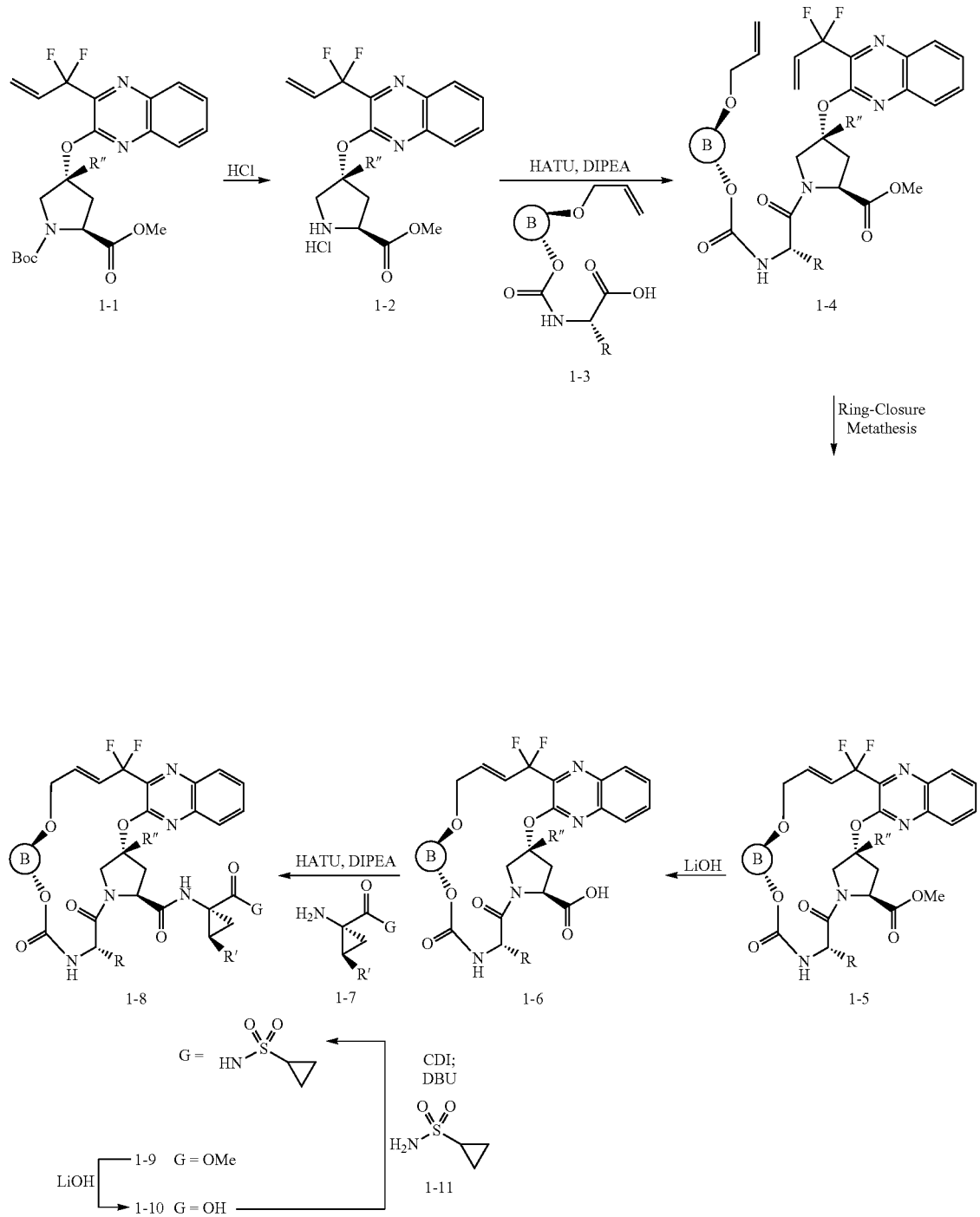

Wherein R', R, G and Ⓑ are previously defined as in Formula I.

The hydrolysis of the macrocyclic ester 1-5 to the corresponding acid 1-6 could be effected with inorganic base, such as, but not limited to LiOH, NaOH, KOH. The resulted acid 1-6 is coupled with amine 1-7 employing amide coupling reagent (the coupling reagent can be selected from, but not limited to, HATU, DCC and HOBT in the presence of organic base such as, but not limited to, DIEPA, TEA, DMAP; for further details on amide formation see recent review: Christian A. G. N. Montalbetti et al., *Tetrahedron* 2005, 61, 10827) to afford amide 1-8 or 1-9. Alternatively, amide 1-8 can be prepared from the acid 1-10, which is synthesized from the hydrolysis of the ester 1-8. The acid 1-9 was activated with CDI and followed by coupling with sulfonamide 1-11 in presence of organic base such as, but not limited to DBU to provide the title compound 1-8.

Scheme 2
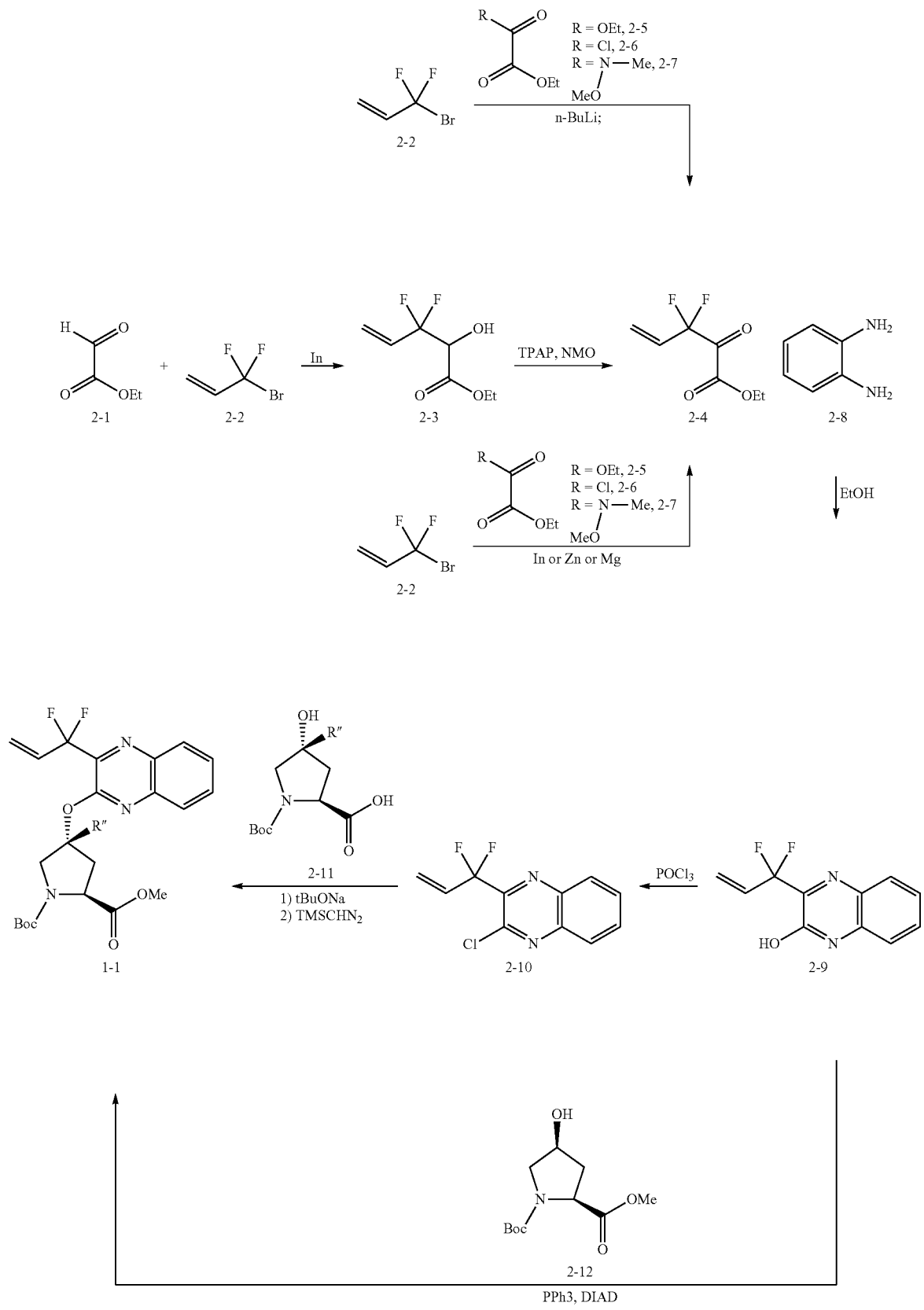

The synthesis of quinoxaline derivative 1-1 is exemplified in Scheme 2. The bromide 2-2 was coupled with aldehyde 2-1 employing metal such as, but not limited to In, Zn, Mg or Cr to afford the hydroxyl ester 2-3, which was further oxidized to give the ketone ester 2-4 with oxidation reagent such a, but not limited to TPAP/NMO. Alternatively, the synthesis of ketone ester 2-4 could be effected through lithium halogen exchange of bromide 2-2 followed by coupling with ester 2-5 (this procedure could also be applied to acid chloride 2-6 or the Weinreb amide 2-7) to afford the ketone ester 2-4. Yet another alternative procedure is that the bromide 2-2 was treated with metal such as, but not limited to In, Zn or Mg and then reacted with acid chloride 2-6 or ester 2-5 or Weinreb amide 2-7 to give the ketone ester 2-4. The ketone ester 2-4 was condensed with diamine 2-8 to afford the quinoxaline 2-9. The hydroxyl quinoxaline 2-9 was converted into chloroquinoxaline 3-3 utilizing chlorination reagent such as but not limited to, $POCl_3$, which was coupled with commercially available N-Boc-trans-4-hydroxy-L-proline 2-11 and followed by esterification to give the quinoxaline derivative 1-1. Alternatively, compound 1-1 could be synthesized from the Mitsunobu reaction of commercially available alcohol 2-12 with quinoxaline 2-9. For further details on the Mitsunobu reaction, see O. Mitsunobu, Synthesis 1981, 1-28; D. L. Hughes, Org. React. 1983, 29, 1; D. L. Hughes, Organic Preparations and Procedures Int. 1996, 28, 127; and J. A. Dodge, S. A. Jones, Recent Res. Dev. Org. Chem. 1997, 1, 273; K. C. Kumara Swamy et. al., Chem. Rev. 2009, 109, 2551.

Scheme 3

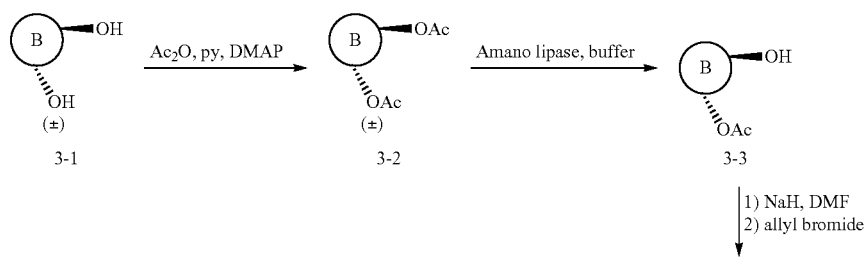

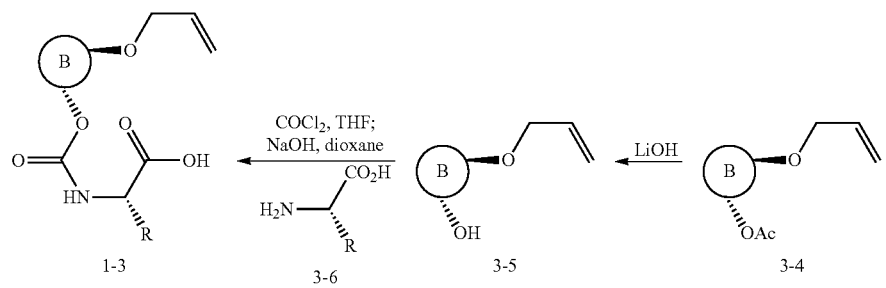

wherein Ⓑ is previously defined as in Formula I.

The synthesis of acid 1-3 commenced with acylation of the racemic diol 3-1 to afford the diacetate 3-2 (for hydroxyl acylation see: T. W. Greene, Protective Groups in Organic Synthesis, Fourth Edition, John Wiley and Sons, 2006). The kinetic resolution of the diacetate 3-2 was achieved by partial deacetylation with enzyme such as, but not limited to, Amano lipase to give the mono acetate 3-3 (M. P. Schneider et al., J. Chem. Soc., Chem. Commun., 1991, 49; for further information on kinetic resolution see: H. Pellissier, Tetrahedron, 2008, 64, 1563). Allylation of monoacetate compound 3-3 affords allyl ether 3-4, which was hydrolyzed with inorganic base such as, but not limited to, LiOH, NaOH to afford the alcohol 3-5. Upon the chloroformation by treating alcohol 3-5 with $COCl_2$, followed by coupling with amino acid 3-6 to provide the acid 1-3. Moreover, the allyl ether 3-5 could also be obtained when optical pure diol 3-1 was deprotonated with NaH followed by coupling with allyl bromide.

Scheme 4

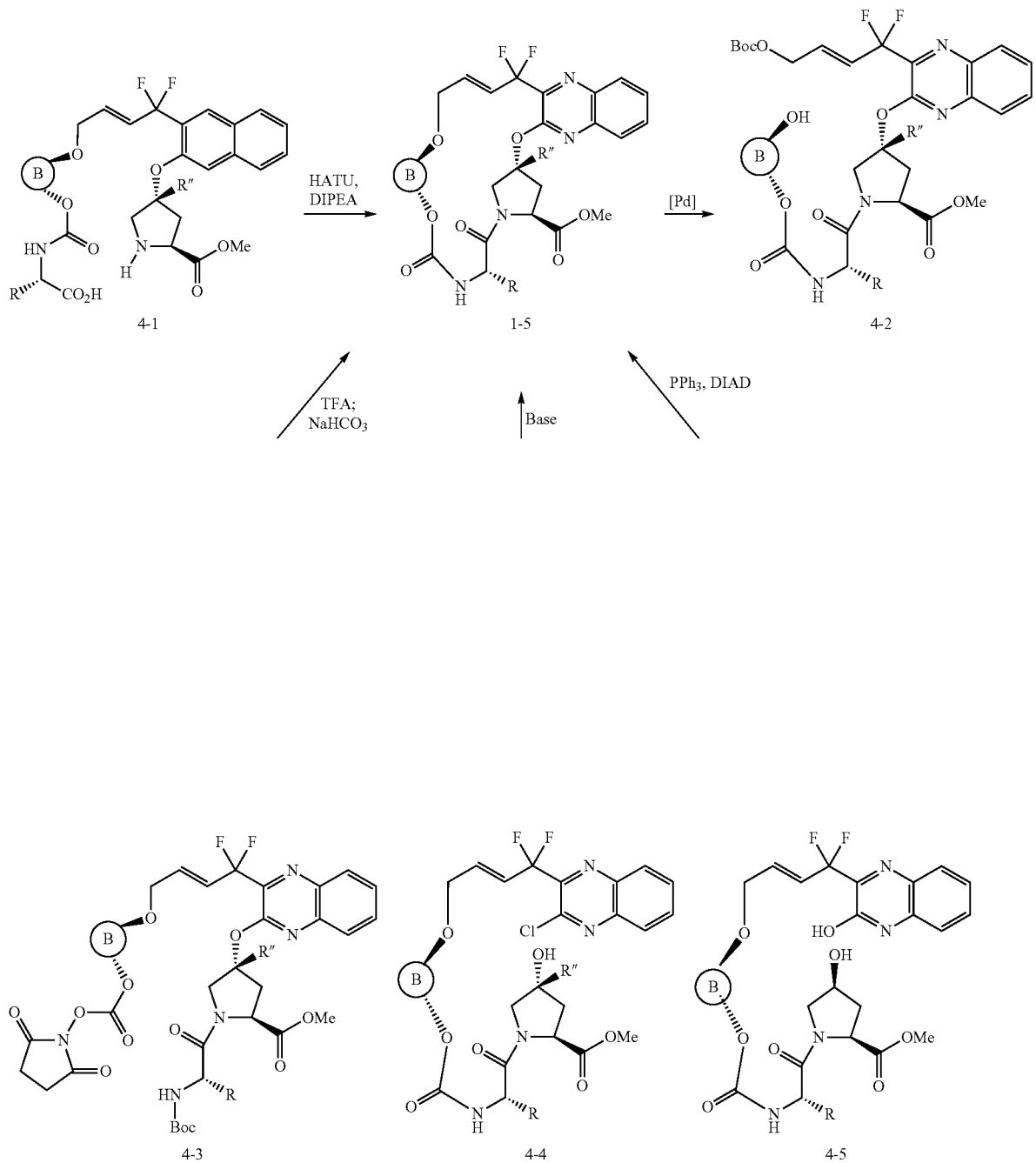

herein R' and Ⓑ are previously defined as in Formula I.

The alternative routes for synthesis of macrocyclic ester 1-5 have been exemplified in Scheme 4. There are many other synthetic routes to this intermediate 1-5, some precursors are shown in Scheme 4. For example, the macrocyclic ester 1-5 could be obtained via the amide bond formation in acid 4-1 (for further details on amide bond formation see recent review: Christian A. G. N. Montalbetti et al., *Tetrahedron* 2005, 61, 10827); Pd catalyzed intramolecular allylation in allylic Boc derivative 4-2 (Guoqiang Wang et al., *Org. Lett.*, 2004, 6, 4455); the deprotection of Boc group (for carbamate deprotection see: T. W. Greene, *Protective Groups in Organic Synthesis*, Fourth Edition, John Wiley and Sons, 2006) followed by carbamate formation in succinimidyl carbonate 4-3 (J. V. Eycken, *J. Org. Chem.*, 2007, 72, 5514); base catalyzed ether formation in alcohol 4-4 and Mitsunobu type ether formation in hydroxyl quinoxaline 4-5 (for further details on the Mitsunobu reaction, see O. Mitsunobu, *Synthesis* 1981, 1-28; D. L. Hughes, *Org. React.* 1983, 29, 1; D. L. Hughes, *Organic Preparations and Procedures Int.* 1996, 28, 127; and J. A. Dodge, S. A. Jones, *Recent Res. Dev. Org. Chem.* 1997, 1, 273; K. C. Kumara Swamy et. al., *Chem. Rev.* 2009, 109, 2551).

Scheme 5

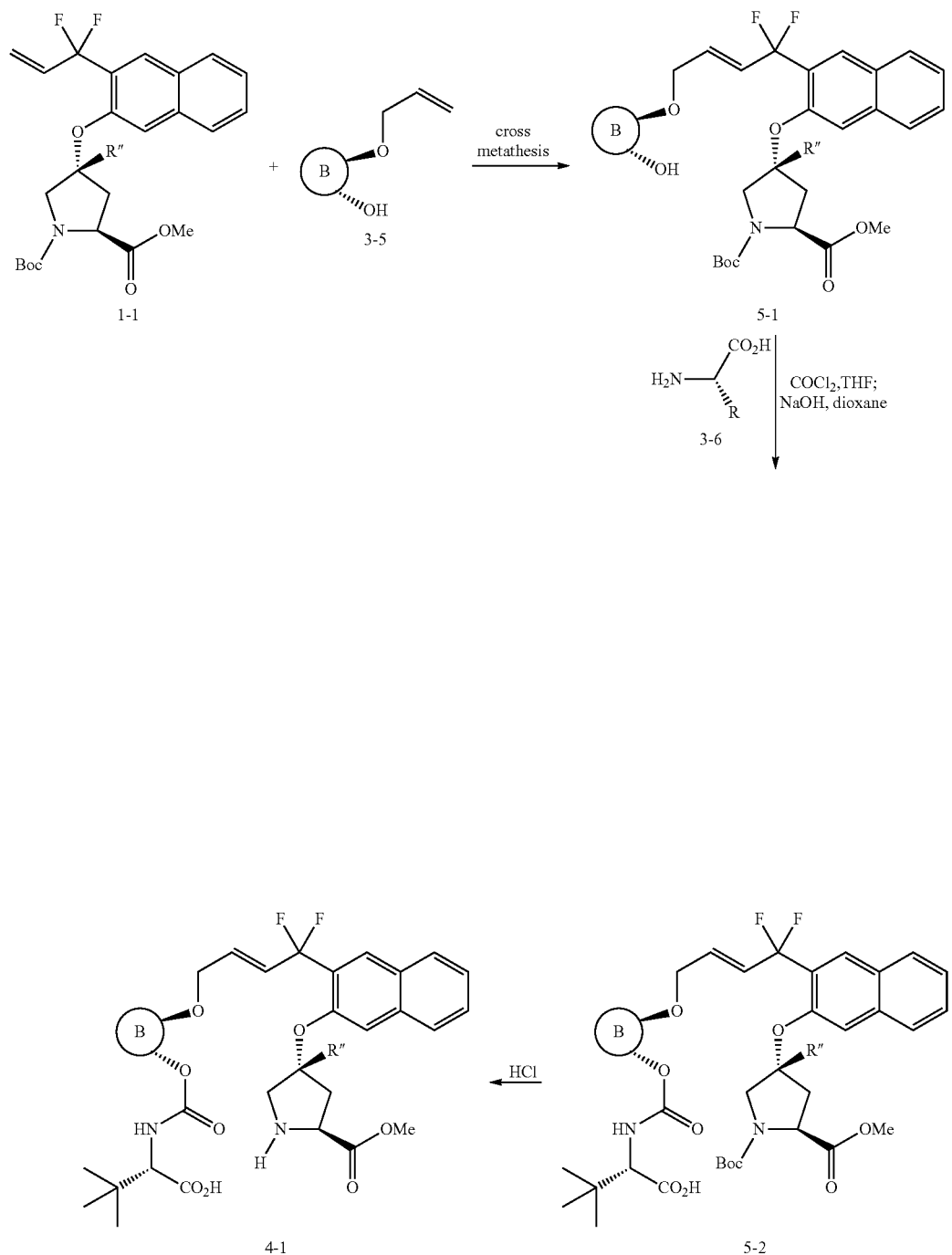

wherein Ⓑ is previously defined as in Formula I.

The synthesis of acid 4-1 has been exemplified in Scheme 5. The cross-metathesis of quinoxaline derivative 1-1 and allyl ether 3-5 leads to the alcohol 5-1 (for further details on cross metathesis see: Grubbs et al. *J. Am. Chem. Soc.* 2003, 125, 11360; R. Raju et al. *Org. Lett.* 2006, 8, 2139; Y. Schrodi et al. *Aldrichimica Acta* 2007, 40, 45). This alcohol 5-1 was treated with phosgene (or some other reagent such as, but not limited to triphosgene, diphosgene, carbonyldiimidazole) followed by coupling with amino acid 3-6 in the present of base such as, but not limited to LiOH or NaOH. The deprotection of Boc group in acid 5-2 (for carbamate deprotection see: T. W. Greene, *Protective Groups in Organic Synthesis*, Fourth Edition, John Wiley and Sons, 2006) affords the acid 4-1.

Scheme 6

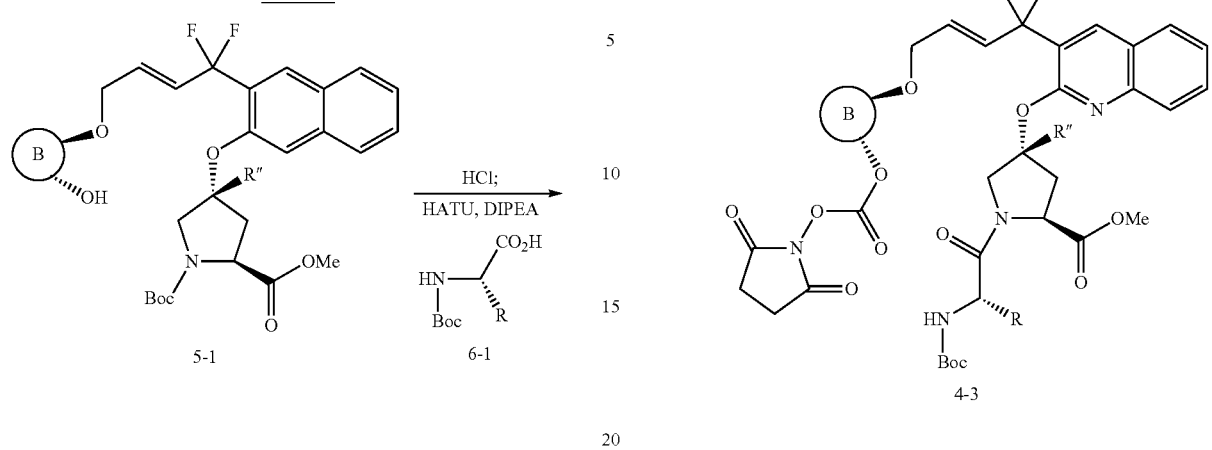

wherein R, R" and Ⓑ are previously defined as in Formula I.

The synthesis of quinoxalinyl derivative 4-3 has been exemplified in Scheme 6. The deprotection of Boc group (T. W. Greene, *Protective Groups in Organic Synthesis*, Fourth Edition, John Wiley and Sons, 2006) in ester 5-1 provides the corresponding amine, which is coupled with amino acid 6-1 utilizing peptide coupling reagent such as, but not limited to HATU, or DCC or BOP (for further details on peptide coupling see: Christian A. G. N. Montalbetti et al., *Tetrahedron* 2005, 61, 10827) to afford the alcohol 6-2. The activation of hydroxyl group in alcohol 6-2 is achieved when treated with DSC/TEA to afford the succinimidyl carbonate 4-3 (for application of DSC in carbamate formation see: J. V. Eycken, *J. Org. Chem.*, 2007, 72, 5514).

Scheme 7

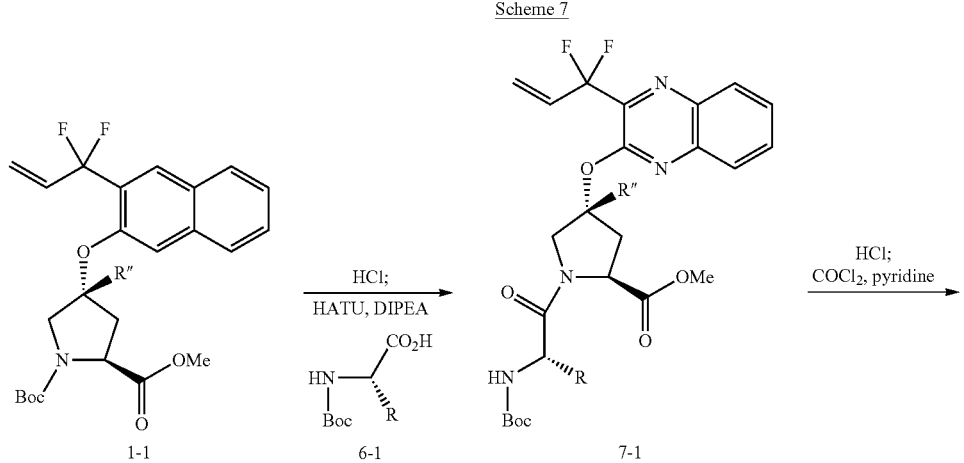

-continued

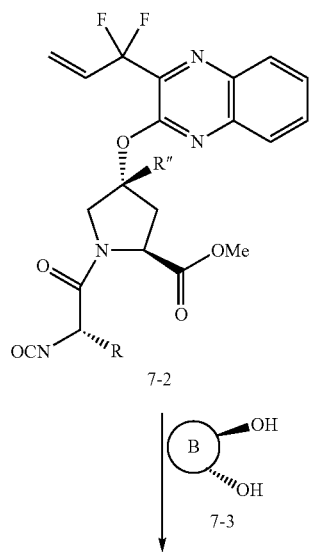
7-2

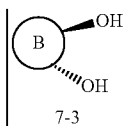
7-3

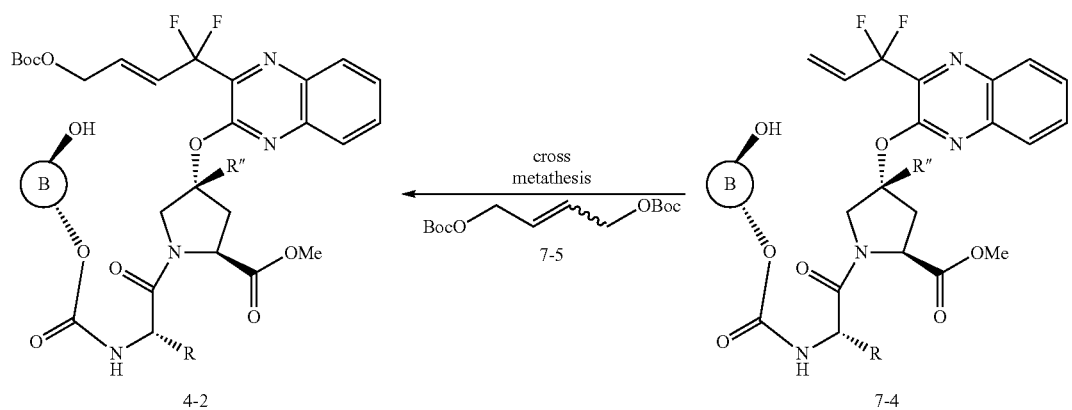

wherein R, R" and (B) are previously defined as in Formula I.

The synthesis of quinoxalinyl derivative 4-2 has been exemplified in Scheme 7. The deprotection of Boc group (T. W. Greene, *Protective Groups in Organic Synthesis*, Fourth Edition, John Wiley and Sons, 2006) of ester compound 1-1 provides the corresponding acid, which is coupled with amino acid 6-1 utilizing peptide coupling reagent such as, but not limited to HATU, or DCC or BOP (for further details on peptide coupling see: Christian A. G. N. Montalbetti et al., *Tetrahedron* 2005, 61, 10827) to afford the alcohol 7-1. The Boc group in compound 7-1 was removed under acidic condition and the resulted amine was treated with phosgene or other reagent such as, but not limited to triphosgene or diphosgene or carbonyldiimidazole in the presence of base such as, but not limited to pyridine or DMAP to afford the isocyanate 7-2. This isocyanate 7-2 was coupled with diol 7-3 in the presence of organic base such as, but not limited to DBU to provide the mono alcohol 7-4. Cross metathesis of alkene 7-4 and protected diol 7-5 in the presence of catalyst provides the alcohol 4-2 (for further details on cross metathesis see: Grubbs et al. *J. Am. Chem. Soc.* 2003, 125, 11360; R. Raju et al. *Org. Lett.* 2006, 8, 2139; Y. Schrodi et al. *Aldrichimica Acta* 2007, 40, 45).

Scheme 8

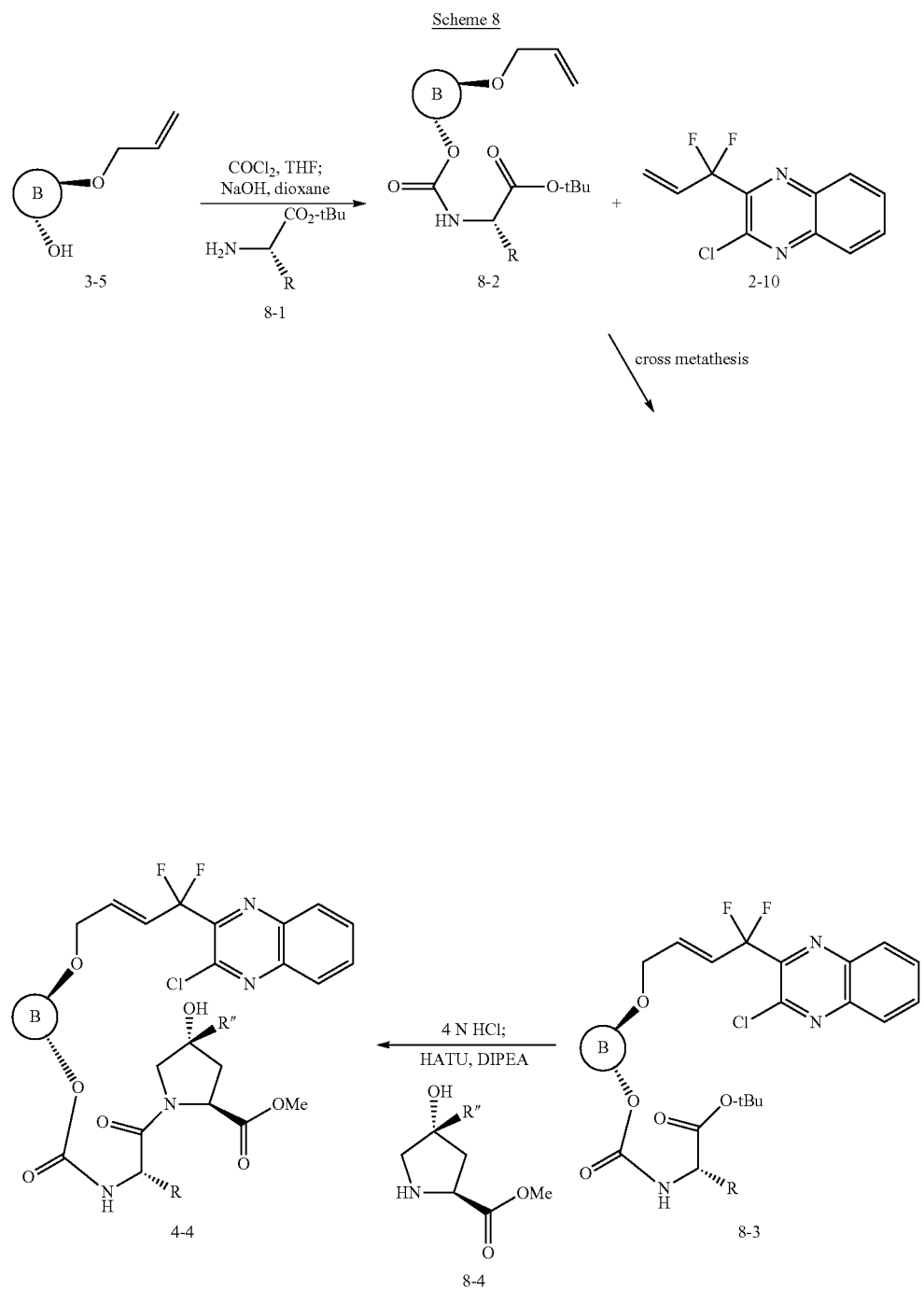

wherein R, R" and Ⓑ are previously defined as in Formula I.

The synthesis of quinoxalinyl derivative 4-4 has been exemplified in Scheme 8. The alcohol 3-5 is treated with phosgene or other reagent such as, but not limited to triphosgene or diphosgene or carbonyldiimidazole and then coupled with amine 8-1 in the presence of base such as, but not limited to NaOH to afford the alkene 8-2, which will undergo cross metathesis with quinoxalinyl derivative 2-10 to provide the t-butyl ester 8-3 (for further details on cross metathesis see: Grubbs et al. *J. Am. Chem. Soc.* 2003, 125, 11360; R. Raju et al. *Org. Lett.* 2006, 8, 2139; Y. Schrodi et al. *Aldrichimica Acta* 2007, 40, 45). The t-butyl group in compound 8-3 was deprotected under acidic condition (the acid is selected from, but not limited to HCl or TFA) and this is followed by coupling with amine 8-4 utilizing peptide coupling reagents (for further details on peptide coupling see: Christian A. G. N. Montalbetti et al., *Tetrahedron* 2005, 61, 10827) to afford the quinoxalinyl compound 4-4.

Scheme 9

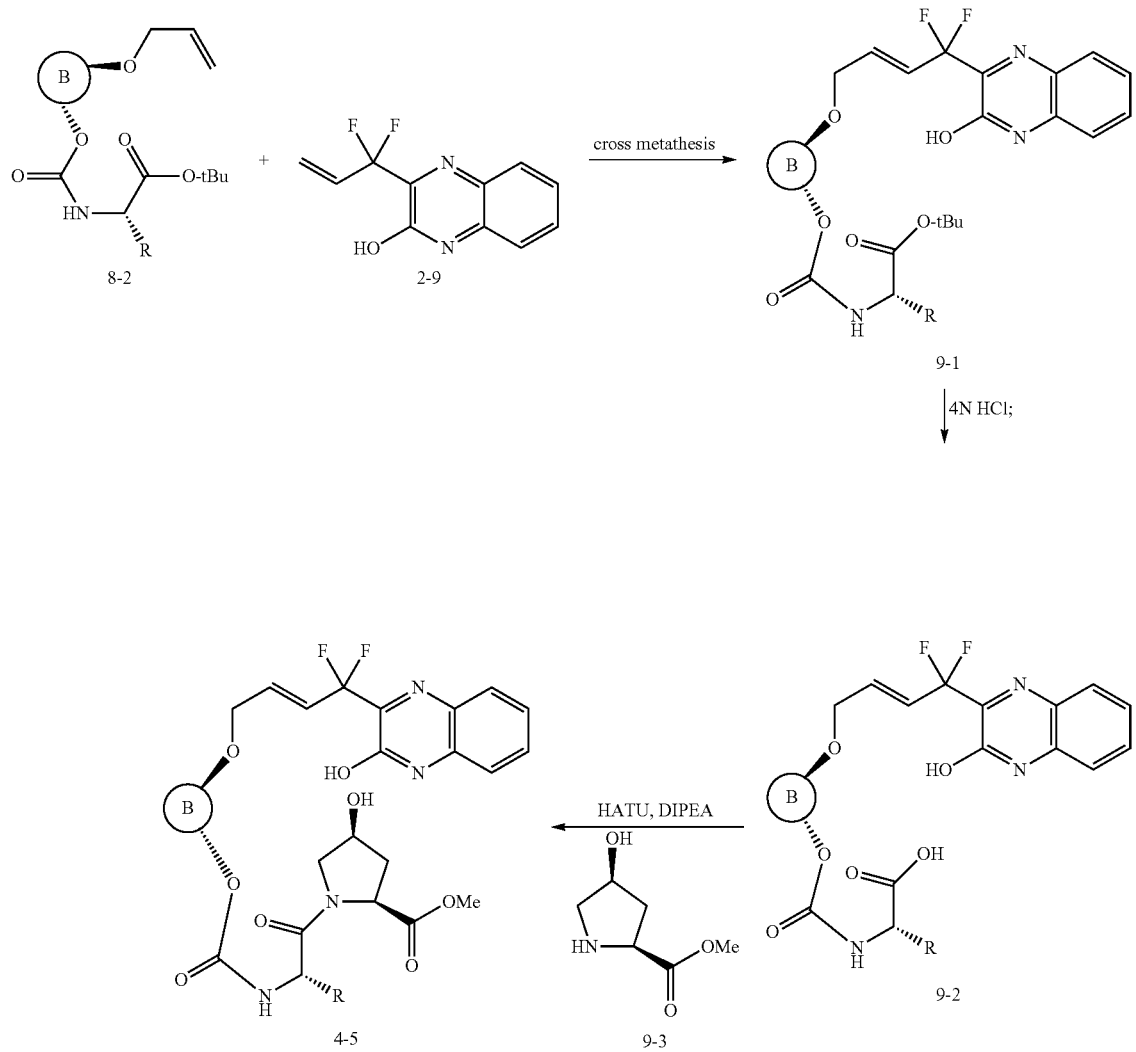

wherein R and Ⓑ is previously defined as in Formula I.

The synthesis of quinoxalinyl derivative 4-5 has been exemplified in Scheme 9. Analogous to the synthesis of intermediate 8-3, the cross metathesis of t-butyl ester 8-2 and quinoxalinyl derivative 2-9 provides the t-butyl ester 9-1. The removal of t-butyl group in 9-1 could be achieved under acidic condition (HCl) to afford the acid 9-2, which undergoes coupling with amine 9-3 employing peptide coupling reagent such as, but not limited to HATU/DIPEA to provide the intermediate 4-5.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of Formula VIII, wherein

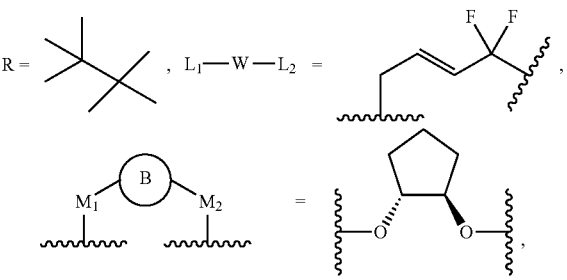

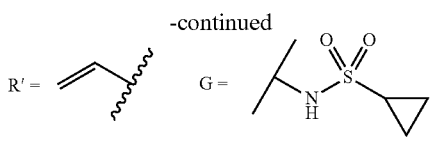

Step 1a

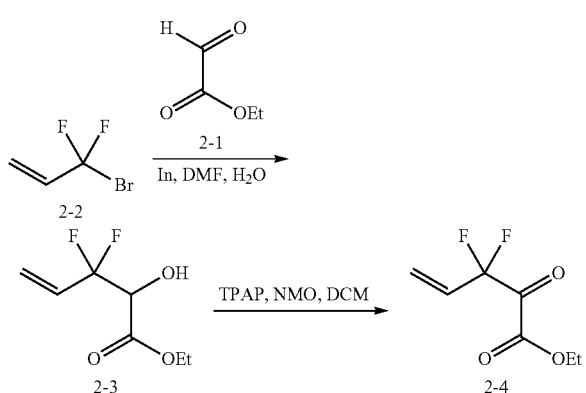

To the solution of 3-bromo-3,3-difluoroprop-1-ene 2-2 (5.61 g, 35.74 mmol) and ethyl glyoxalate 2-1 (6.52 ml, 42.9 mmol, 50% in toluene) in DMF (80 ml) and water (20 ml) was added Indium powder. The resulted mixture was stirred vigorously for 6 h, and then diluted with TBME, the mixture was filtered and washed with water, brine, dried and concentrated in vacuo to afford the crude product 2-3 (6.21 g). This material was used directly to next step without further purification.

To the crude ethyl 3,3-difluoro-2-hydroxypent-4-enoate 2-3 (4.9 g, 27.20 mmol) in DCM (150 ml) was added TPAP (240 mg, 0.68 mmol) and NMO (11.03 g, 81.61 mmol). The suspension was stirred at rt for 5 h, and then diluted with DCM, washed with water, brine, dried and concentrated in vacuo to afford the crude ketone ester 2-4. This material was used directly to next step without further purification.

Step 1b

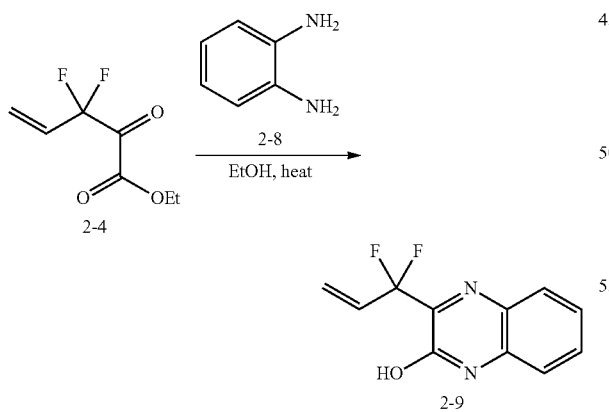

To the solution of crude ethyl 3,3-difluoro-2-oxopent-4-enoate 2-4 (prepared from 35.74 mmol of 3-bromo-3,3-difluoroprop-1-ene) in EtOH (200 ml) was added o-benzene-1,2-diamine 2-8 (4.64 g, 42.89 mmol). The resulted mixture was heated to reflux for 14 h and then cool down to rt, the solid was collected by filtration and washed with cold EtOH to give quinoxaline 2-9 (2.81 g) after drying. The filtrate was concentrated in vacuo and the residue was purified by flash chromatography on CombiFlash with Hexane to 30% acetone in hexane to afford another portion of quinoxaline 2-9 (0.43 g). MS (ESI): m/z=223.09 [M+H].

Step 1c

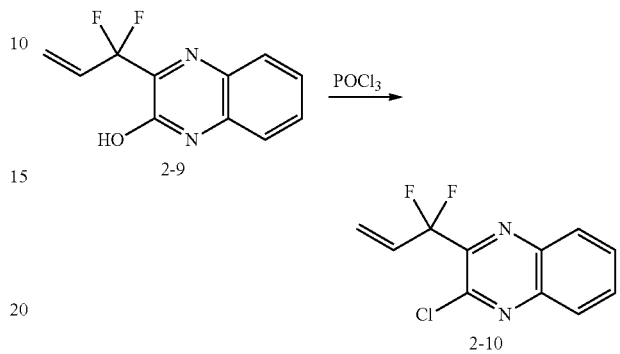

To 3-(1,1-difluoroallyl)quinoxalin-2-ol 2-9 (2.31 g, 10.40 mmol) was added $POCl_3$ (10.8 ml) and DMF (1.1 ml), the resulted mixture was heated to 65° C. for 2 h. The mixture was diluted with ethyl acetate and then slowly poured into ice. After partition the organic layer was washed with water, $NaHCO_3$ solution and brine to give the desired product 2-10 (2.45 g). This material was used directly to next step without further purification. MS (ESI): m/z=241.01 [M+H].

Step 1d

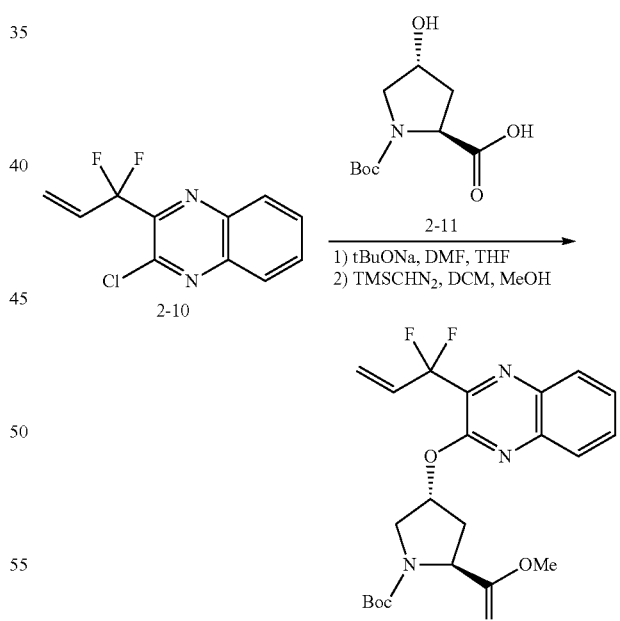

To a solution of N-Boc-trans-4-hydroxy-L-proline 2-11 (2.404 g, 10.396 mmol) in DMF (14 ml) and THF (60 ml) at 0° C. was added t-BuONa (3.0 g, 31.189 mmol) portionwise. The reaction mixture was allowed to warm up to rt. After stirring for 1 h, the mixture was cooled down to 0° C. and 2-chloro-3-(1,1-difluoroallyl)quinoxaline 2-10 (2.45 g, ~10.396 mmol) was added and warmed up to rt. After stirring for 4 h, the reaction mixture was quenched with 1 N HCl at 0° C. The aqueous layer was extracted with EtOAc (3×), and the organic layer was combined, washed with water, brine, dried and concentrated in vacuo. To the residue in DCM (50 ml) and MeOH (10 ml) was added TMSCHN$_2$ (10.4 ml, 20.792 mmol, 2.0 M in Hexane). The solution was stirred at rt for 30 min then concentrated in vacuo. The residue was purified by flash chromatography on CombiFlash with Hexane to 30% ethyl acetate in hexane to afford desired product 1-1 (3.84 g, 82%). MS (ESI): m/z=450.24 [M+H].

Step 1e

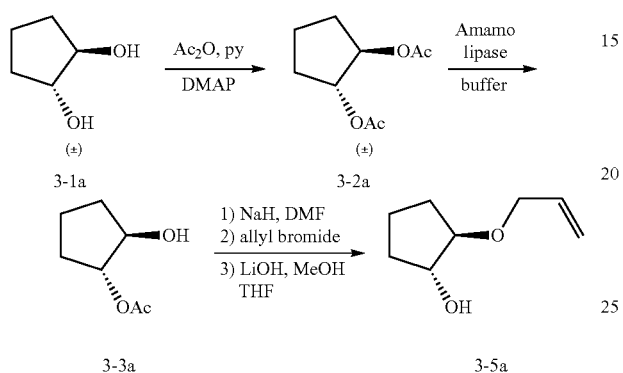

To a solution of (±)-cyclopentane-1,2-diol 3-1a (10.02 g, 97.159 mmol) in DCM (20 ml) and pyridine (150 ml) was added acetic anhydride (36.7 ml, 388.63 mmol) and DMAP (593 mg) portionwise. The resulted solution was stirred for 21 h, and solvent was removed in vacuo. The residue was dissolved in EtOAc, and the resulted solution was washed with 1N HCl, water, NaHCO$_3$, water and brine. The organic layer was dried and concentrated in vacuo. The residue was purified by flash chromatography on CombiFlash with Hexane to 15% acetone in hexane to afford the diacetate 3-2a (17.1 g, 94%).

To the suspension of (±)-cyclopentane-1,2-diyl diacetate 3-2a (17.0 g, 91.3 mmol) in buffer (pH=7, 140 ml) was added Amano Lipase PS (from Burkholderia cepacia, Aldrich, 1.81 g). The resulted mixture was vigorously stirred and 1 N NaOH (65 ml) was added via an addition funnel over 18 h to keep the pH at 7. The mixture was diluted with EtOAc and water, filtered and the aqueous layer was extracted with EtOAc. The organic layer was combined, washed with water, brine, dried (Na$_2$SO$_4$) and concentrated in vacuo. The residue was purified by flash chromatography on CombiFlash with Hexane to 35% acetone in hexane to afford desired product 3-3a (4.6 g, 35%).

To a solution of (1R,2R)-2-hydroxycyclopentyl acetate 3-3a (3.42 g, 23.715 mmol) in DMF (80 ml) at 0° C. was added NaH (1.04 g, 26.087 mmol, 60% dispersion in mineral oil). Te resulted mixture was warmed up to rt and stirred for 30 min, and it was cooled down to 0° C. and allyl bromide (2.2 ml, 26.087 mmol) was added. The mixture was stirred at rt for 1.5 h and quenched with NH$_4$Cl solution at 0° C. The mixture was extracted with EtOAc (3×), and the organic layer was combined, washed with water, brine, dried (Na$_2$SO$_4$) and concentrated in vacuo. To the residue in MeOH (47 ml) and THF (94 ml) was added 1 N LiOH solution (47.4 ml, 47.43 mmol). The mixture was stirred for 30 min and the mixture was extracted with EtOAc (3×), and the organic layer was combined, washed with water, brine, dried (Na$_2$SO$_4$) and concentrated in vacuo. The residue was purified by flash chromatography on CombiFlash with Hexane to 25% acetone in hexane to afford alcohol 3-5a (1.36 g, 40%, 95.8% ee by HPLC).

Step 1f

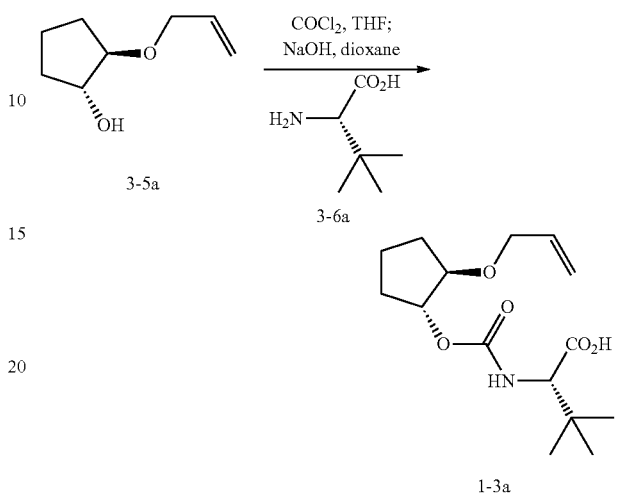

To a solution of (1R,2R)-2-(allyloxy)cyclopentanol 3-5a (2.20 g, 15.50 mmol) in THF (150 ml) was added phosgene solution (16.3 ml, 30.9 mmol, 20% in toluene). The resulted solution was stirred for 14 h, and concentrated in vacuo. To the residue in dioxane (50 ml) was added L-tert-leucine 3-6a (2.237 g, 17.05 mmol) in dioxane (100 ml) and 1 N NaOH (18.6 ml, 18.6 mmol). The mixture was stirred for 5 h, and acidified with 1N HCl. The mixture was extracted with EtOAc (3×), and the organic layer was combined, washed with water, brine, dried and concentrated in vacuo to afford the acid 1-3a (4.32 g). This material was used directly to next step without further purification.

Step 1g

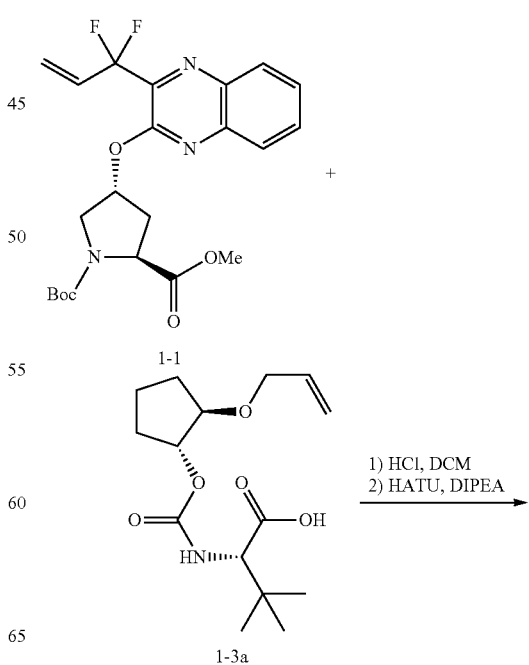

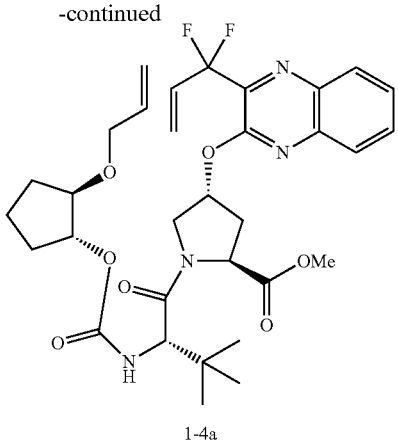

1-4a

To a solution of quinoxaline derivative 1-1 (3.02 g, 6.719 mmol) in DCM (20 ml) was added 4 N HCl (20 ml, in dioxane). The resulted solution was stirred for 2 h and solvent was removed in vacuo. To the residue in DMF (67 ml) was added acid 1-3a (1.849 g, 8.063 mmol), HATU (3.321 g, 8.735 mmol) and DIPEA (2.33 ml, 13.438 mmol). The mixture was stirred for 3 h and concentrated in vacuo. The residue was dissolved in EtOAc and washed with 1 N HCl (2×), water, brine, dried (Na$_2$SO$_4$) and concentrated in vacuo. The residue was purified by flash chromatography on CombiFlash with Hexane to 35% EtOAc in hexane to afford diene 1-4a (2.48 g, 59%). MS-ESI m/z 631.43 (M+H)$^+$.

Step 1h

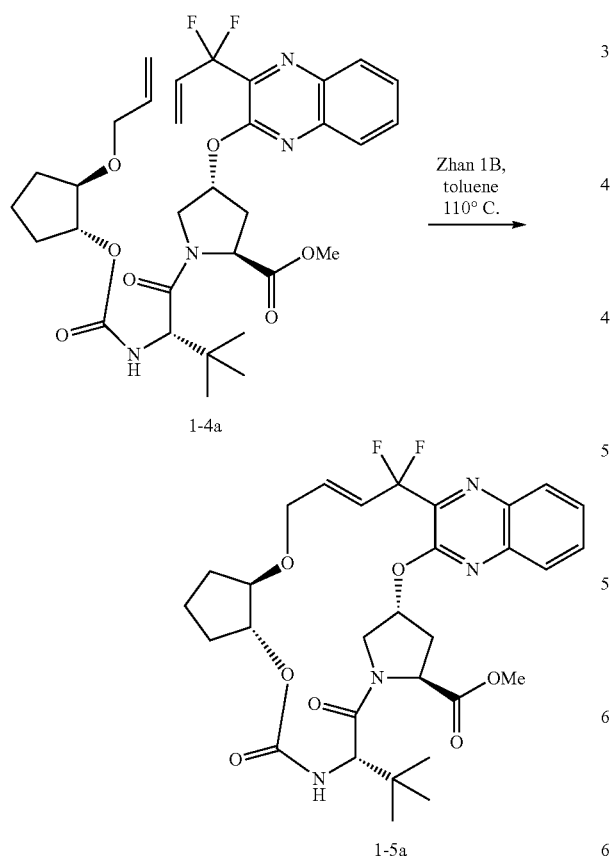

To a solution of the diene 1-4a (1.38 g, 2.188 mmol) in toluene under nitrogen atmosphere at 110° C. was added Zhan 1B catalyst (128 mg, 0.140 mmol) and the resulted solution was stirred at 110° C. for 37 h. Zhan 1B catalyst (70 mg×2) was added in two portions and the reaction was stopped until the disappearance of starting material by MS. The mixture was concentrated in vacuo and the residue was purified by flash chromatography on CombiFlash with Hexane to 40% EtOAc in hexane to afford the alkene 1-5a (0.768 g, 59%). MS-ESI m/z 603.20 (M+H)$^+$.

Step 1i

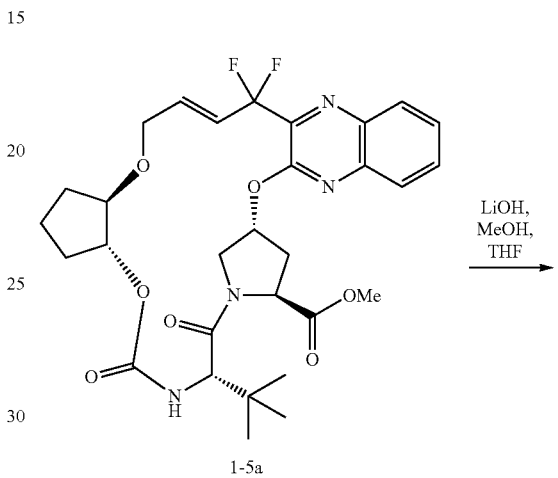

1-5a

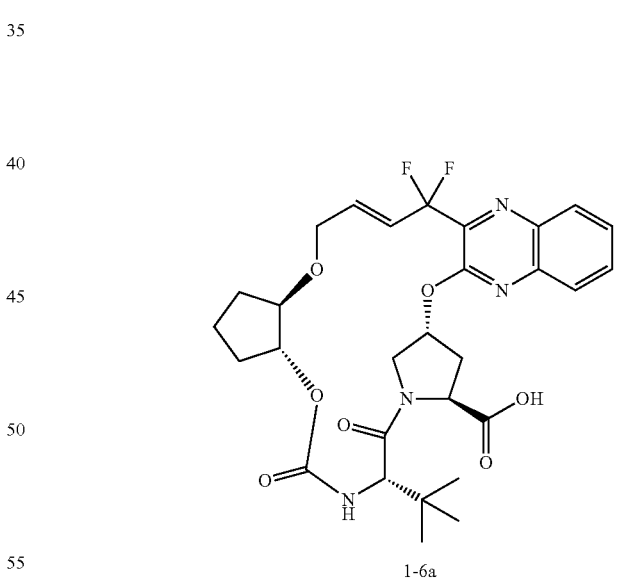

1-6a

To a solution of the ester 1-5a (1.38 g, 2.29 mmol) in MeOH (23 ml) and THF (46 ml) was added LiOH solution (22.9 ml, 1 N). The resulted mixture was stirred for 16 h and quenched with 1 N HCl. The mixture was extracted with DCM (3×), and the organic layer was combined, washed with brine, dried (Na$_2$SO$_4$) and concentrated in vacuo to afford the acid 1-6a. The acid was used to the next step without further purification.

Step 1j

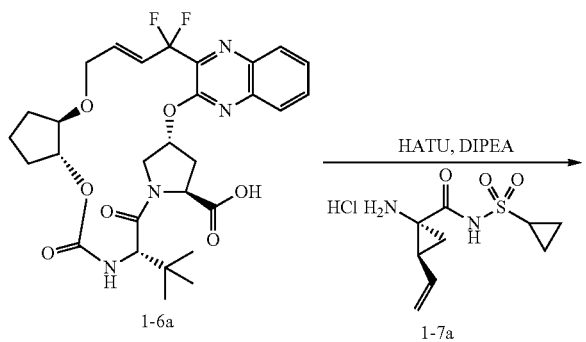

1-6a

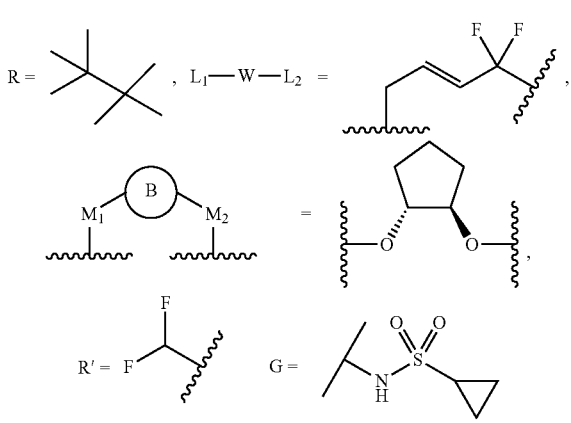

example 1

The acid 1-6a (crude product from step 1i) was dissolved in DCM (70 ml), and to this solution was added sulfonamide 1-7a (702 mg, 2.404 mmol), HATU (1.045 g, 2.748 mmol) and DIPEA (0.60 ml, 3.435 mmol). The mixture was stirred for 3 h, and then diluted with DCM. The organic layer was washed with 1 N HCl, water, brine, dried and concentrated in vacuo. The residue was first purified by flash chromatography on CombiFlash with Hexane to 50% EtOAc in hexane and then further purified by HPLC to afford the title compound (1.126 g, 60%). MS-ESI m/z 801.40 (M+H)$^+$.

Example 2

Compound of Formula VIII, Wherein

Step 2a

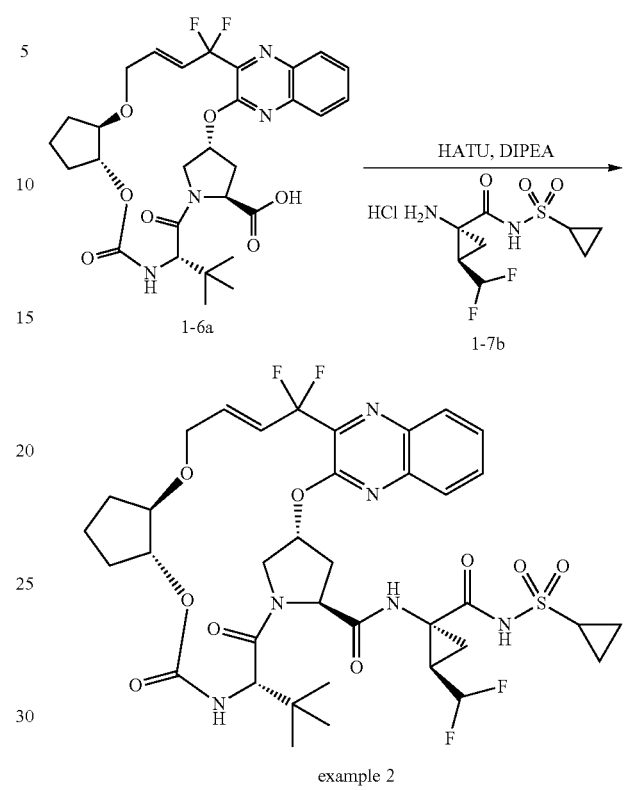

The acid 1-6a (19.5 mg, 0.0332 mmol) was dissolved in DCM (1.0 ml), and to this solution was added sulfonamide 1-7b (13.2 mg, 0.0432 mmol), HATU (18.9 mg, 0.0498 mmol) and DIPEA (11.5 ul, 0.0664 mmol). The mixture was stirred for 3 h, and then diluted with DCM. The organic layer was washed with 1 N HCl, water, brine, dried and concentrated in vacuo. The residue was purified by HPLC to afford the title compound. MS-ESI m/z 825.39 (M+H)$^+$.

Example 4

Compound of Formula VIII, Wherein

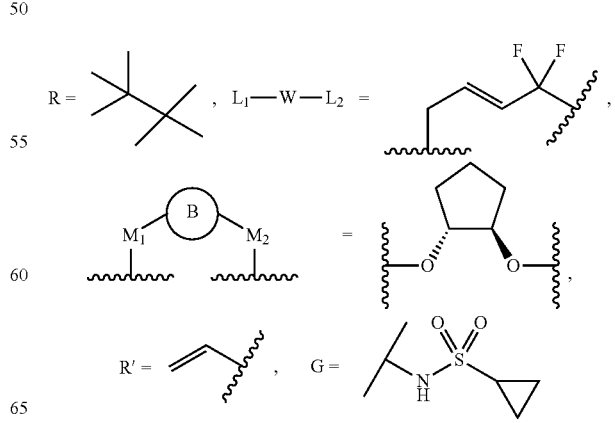

Step 4a

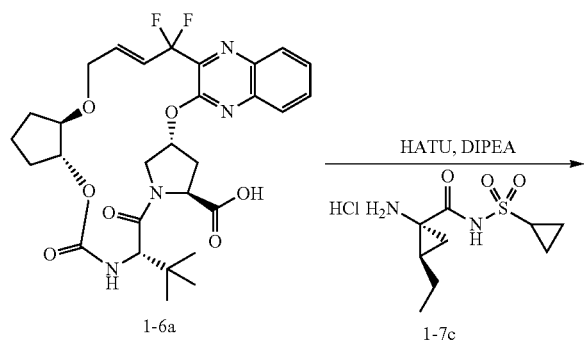

The acid 1-6a (21 mg, 0.0356 mmol) was dissolved in DCM (1.5 ml), and to this solution was added sulfonamide 1-7c (12.4 mg, 0.0463 mmol), HATU (17.6 mg, 0.0462 mmol) and DIPEA (12.4 ul, 0.0712 mmol). The mixture was stirred for 3 h, and then diluted with DCM. The organic layer was washed with 1 N HCl, water, brine, dried and concentrated in vacuo. The residue was purified by HPLC to afford the title compound. MS-ESI m/z 803.25 (M+H)$^+$.

Example 5

Compound of Formula VIII, Wherein

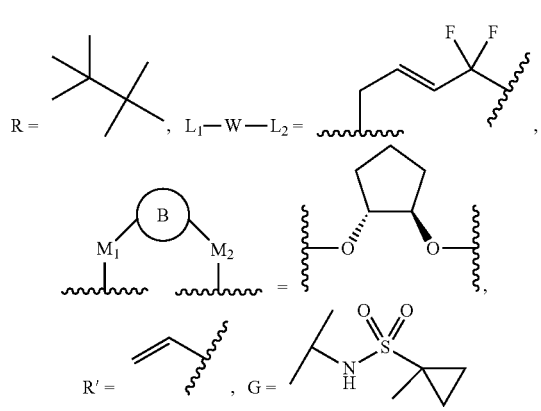

Step 5a

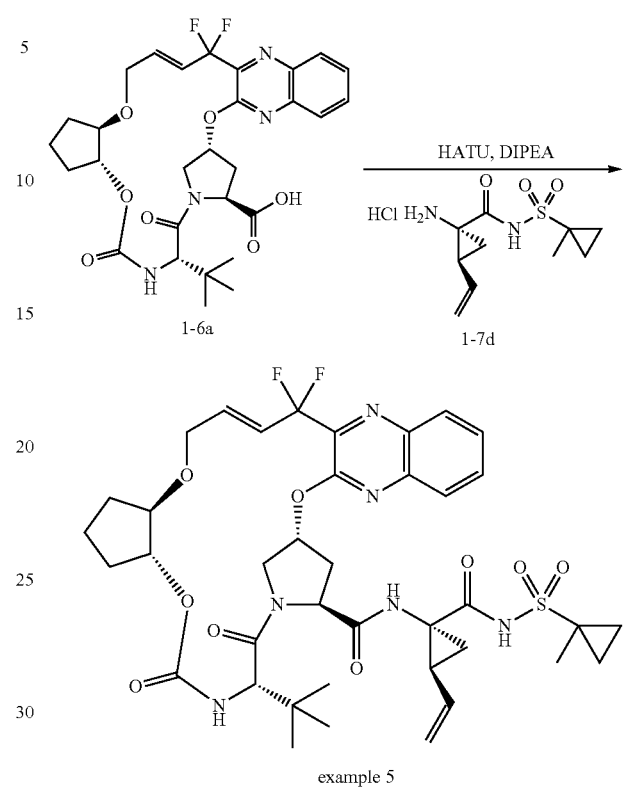

The acid 1-6a (19.5 mg, 0.0332 mmol) was dissolved in DMF (0.5 ml) and DCM (0.5 ml), and to this solution was added sulfonamide 1-7d (13.8 mg, 0.0465 mmol), HATU (18.9 mg, 0.0498 mmol) and DIPEA (11.5 ul, 0.0664 mmol). The mixture was stirred for 2 h and the solvent was removed in vacuo, the residue was purified by HPLC to afford the title compound. MS-ESI m/z 815.38 (M+H)$^+$.

Example 6

Compound of Formula VIII, Wherein

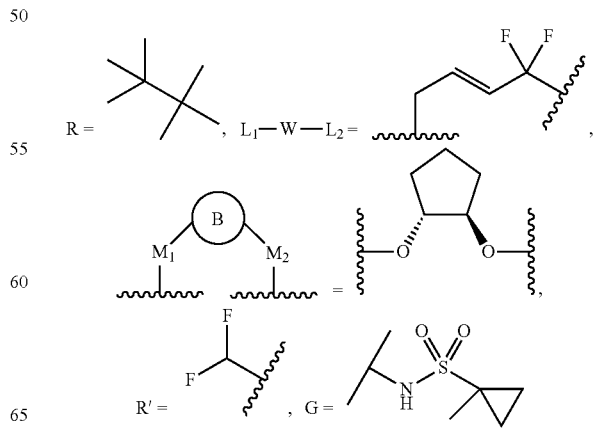

Step 6a

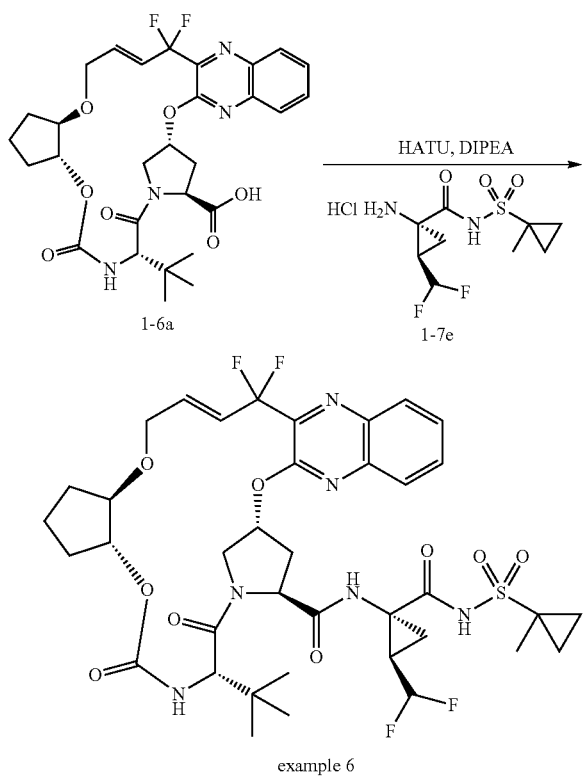

1-6a    1-7e example 6

The acid 1-6a (21 mg, 0.0356 mmol) was dissolved in DCM (1.5 ml), and to this solution was added sulfonamide 1-7e (13.0 mg, 0.0463 mmol), HATU (17.6 mg, 0.0462 mmol) and DIPEA (12.4 ul, 0.0712 mmol). The mixture was stirred for 3 h, and then diluted with DCM. The organic layer was washed with 1 N HCl, water, brine, dried and concentrated in vacuo. The residue was purified by HPLC to afford the title compound. MS-ESI m/z 839.41 (M+H)$^+$.

Example 8

Compound of Formula VIII, Wherein

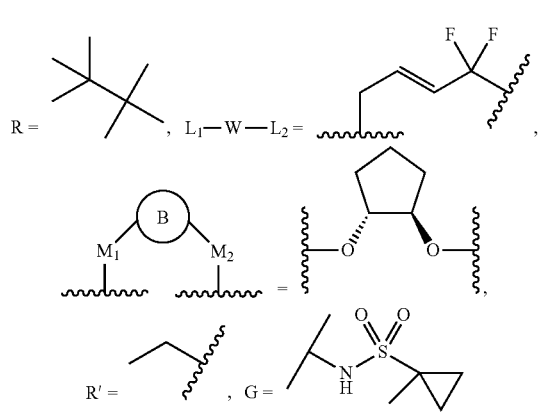

Step 8a

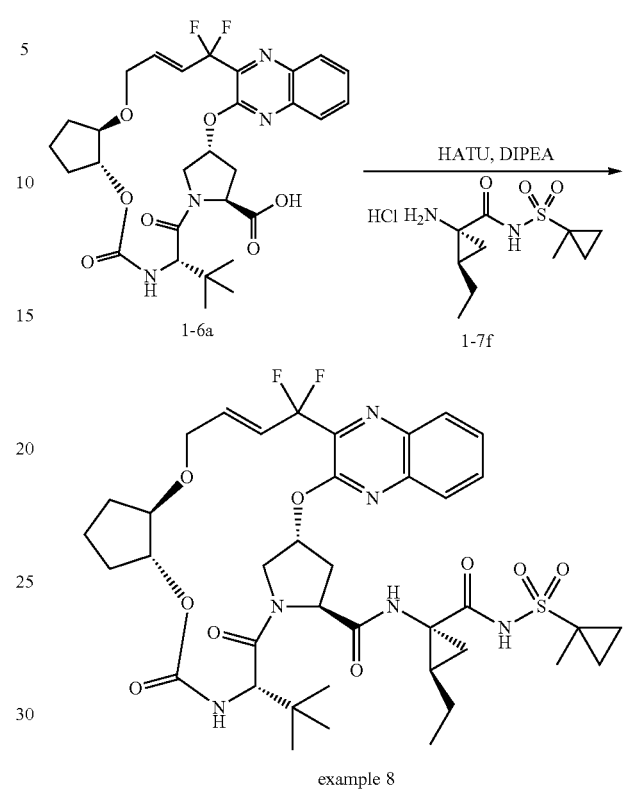

1-6a    1-7f example 8

The acid 1-6a (19.5 mg, 0.0332 mmol) was dissolved in DMF (0.5 ml) and DCM (0.5 ml), and to this solution was added sulfonamide 1-7f (13.8 mg, 0.0465 mmol), HATU (18.9 mg, 0.0498 mmol) and DIPEA (11.5 ul, 0.0664 mmol). The mixture was stirred for 2 h and the solvent was removed in vacuo, the residue was purified by HPLC to afford the title compound. MS-ESI m/z 817.37 (M+H)$^+$.

Example 34

Compound of Formula VIII, Wherein

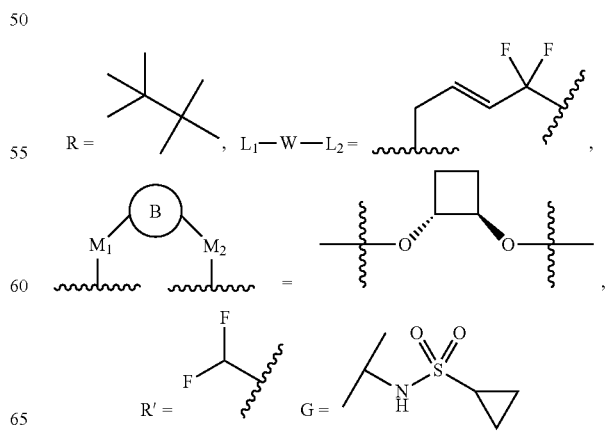

Step 34a

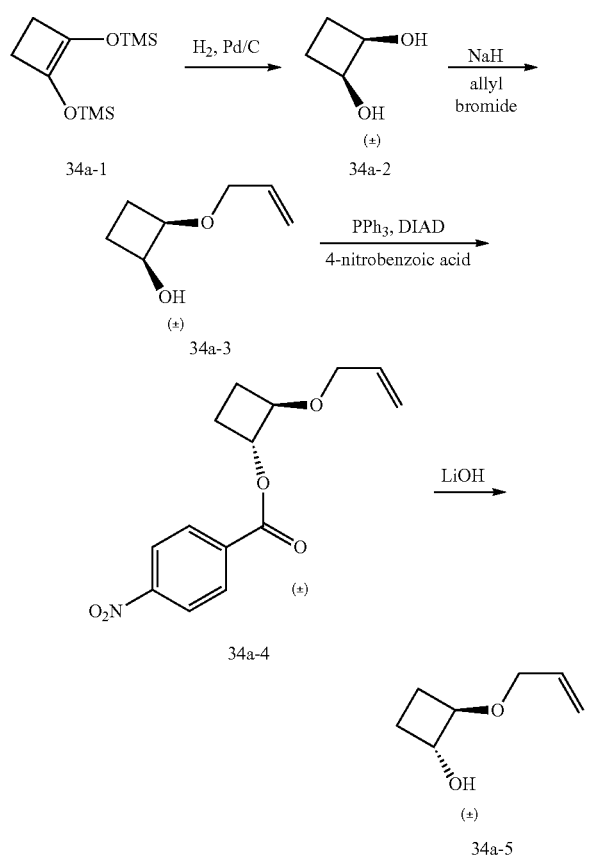

Step 34b

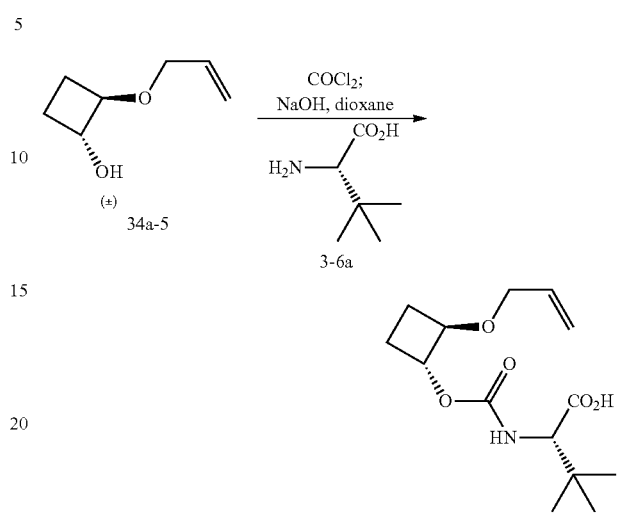

A mixture of compound 34a-1 (2.0 g, 8.678 mol), Pd/C (458 mg, 0.434 mmol, 10% wet) and THF (100 ml) was hydrogenated under 60 PSI for 15 h, and another portion of Pd/C (458 mg) was added, the mixture was stirred for another 20 h until the disappearance of starting material. The mixture was filtered, washed with ethyl acetate. The filtrate was concentrated in vacuo and the residue was purified by flash chromatography on CombiFlash with Hexane to 60% EtOAc in hexane to afford the diol 34a-2 (315 mg, 41%).

To the solution of diol 34a-2 (400 mg, 4.545 mmol) in DMF (8 ml) at 0° C. was added NaH (200 mg, 5.0 mmol, 60% dispersion in mineral oil). The resulted mixture was warmed up to rt and stirred for 40 min, the allyl bromide (0.42 ml, 5.0 mmol) was added. The mixture was stirred for 2 h, and quenched with NH$_4$Cl solution. The mixture was diluted with ethyl acetate, washed with water, brine, dried (Na$_2$SO$_4$) and concentrated in vacuo. The residue was purified by flash chromatography on CombiFlash with Hexane to 25% acetone in hexane to afford the alcohol 34a-3 (132 mg).

To the solution of alcohol 34a-3 (132 mg, 1.031 mmol), PPh$_3$ (810.9 mg, 3.092 mmol) and 4-nitrobenzoic acid (586 mg, 3.505 mmol) in THF (10 ml) was added DIAD (0.61 ml, 3.092 mmol). The resulted solution was stirred for 11 h, and the solvent was removed in vacuo. The residue was purified by flash chromatography on CombiFlash with Hexane to 40% EtOAc in hexane to afford the ester 34a-4 (161 mg, 56%).

To the solution of alcohol 34a-4 (161 mg, 0.581 mmol) in THF (4 ml) and MeOH (2 ml) was added LiOH (2 ml, 1 N). The mixture was stirred for 2.5 h and the mixture was extracted with EtOAc (3×). The organic layer was combined, washed with water, brine, dried (Na$_2$SO$_4$) and concentrated in vacuo to afford the alcohol 34a-5 (58 mg). This material was used directly to the next step without further purification.

To a solution of (1R,2R)-2-(allyloxy)cyclobutanol 34a-5 (58 mg, 0.453 mmol) in THF (2 ml) was added phosgene solution (0.48 ml, 0.906 mmol, 20% in toluene). The resulted solution was stirred for 4 h, and concentrated in vacuo. To the residue in dioxane (5 ml) was added L-tert-leucine 3-6a (71 mg, 0.544 mmol) and 1 N NaOH (0.59 ml, 0.59 mmol). The mixture was stirred for 14 h, and acidified with 1N HCl. The mixture was extracted with EtOAc (3×), and the organic layer was combined, washed with water, brine, dried and concentrated in vacuo to afford the acid 1-3b (117 mg). This material was used directly to next step without further purification.

Step 34c

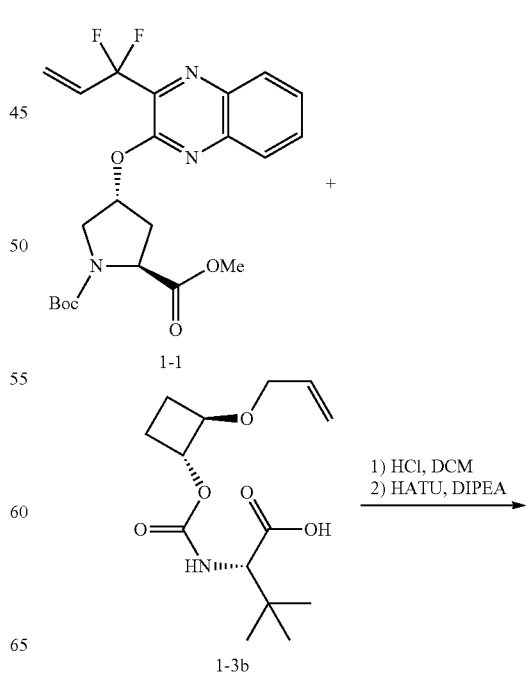

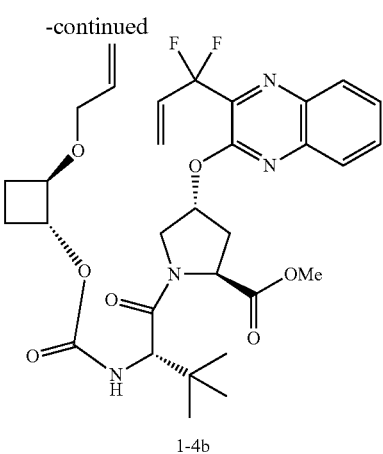

1-4b

To a solution of quinoxaline derivative 1-1 (224 mg, 0.498 mmol) in DCM (2 ml) was added HCl (3 ml, 4 N in dioxane). The resulted solution was stirred for 1.5 h and solvent was removed in vacuo. To the residue in DCM (8 ml) was added acid 1-3b (120 mg, 0.453 mmol), HATU (258 mg, 0.680 mmol) and DIPEA (0.17 ml, 0.996 mmol). The mixture was stirred for 3 h and concentrated in vacuo. The residue was dissolved in EtOAc and washed with 1 N HCl (2×), water, brine, dried ($Na_2SO_4$) and concentrated in vacuo. The residue was purified by flash chromatography on CombiFlash with Hexane to 35% EtOAc in hexane to afford diene 1-4b (115 mg). MS-ESI m/z 617.3 $(M+H)^+$.

Step 34d

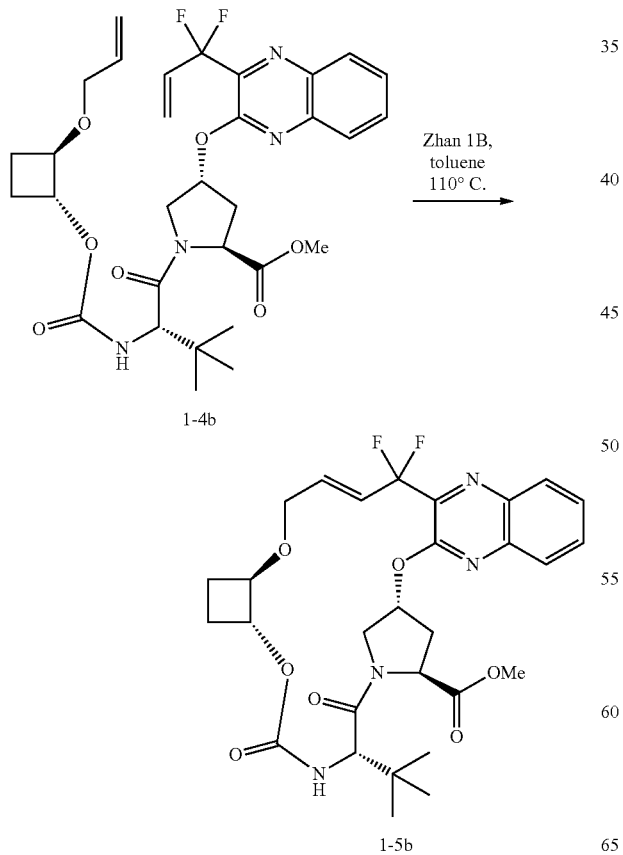

To a solution of the diene 1-4b (115 mg, 0.186 mmol) in toluene under nitrogen atmosphere at 110° C. was added Zhan 1B catalyst (14 mg, 0.0186 mmol) and the resulted solution was stirred at 110° C. for 19 h. The mixture was concentrated in vacuo and the residue was purified by flash chromatography on CombiFlash with Hexane to 35% EtOAc in hexane to afford the alkene 1-5b (38 mg). MS-ESI m/z 589.25 $(M+H)^+$.

Step 34e

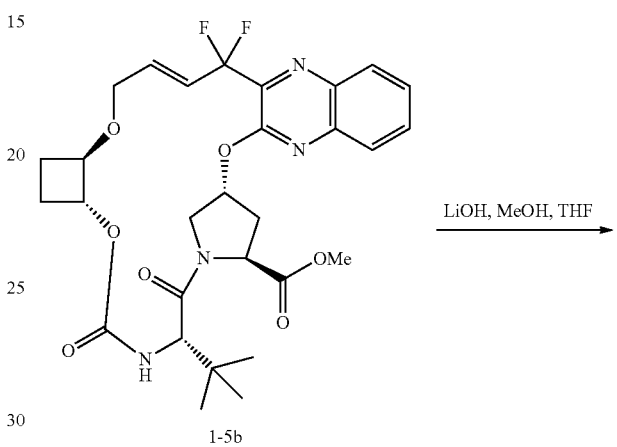

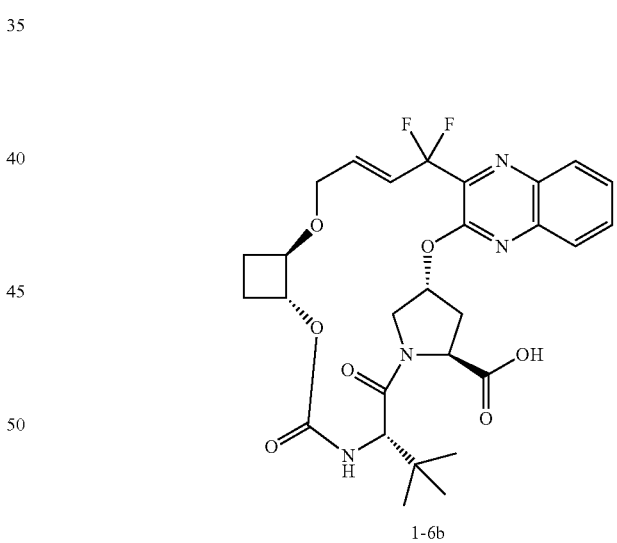

1-6b

To a solution of the ester 1-5b (38 mg, 0.0646 mmol) in MeOH (1 ml) and THF (2 ml) was added LiOH solution (1 ml, 1 N). The resulted mixture was stirred for 14 h and quenched with 1 N HCl. The mixture was extracted with ethyl acetate (3×), and the organic layer was combined, washed with brine, dried ($Na_2SO_4$) and concentrated in vacuo to afford the acid 1-6b. The acid was used to the next step without further purification. MS-ESI m/z 575.27 $(M+H)^+$.

Step 34f

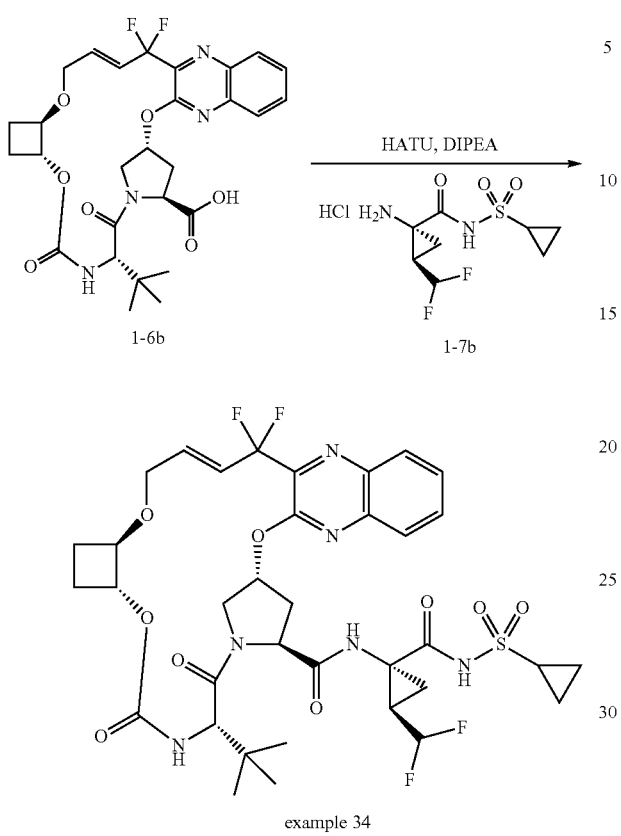

1-6b

Following procedure described in the preparation of example 2 (step 2a), acid 1-6b was converted to compound example 34. MS-ESI m/z 833.40 (M+H)⁺.

Example 36

Compound of Formula VIII, Wherein

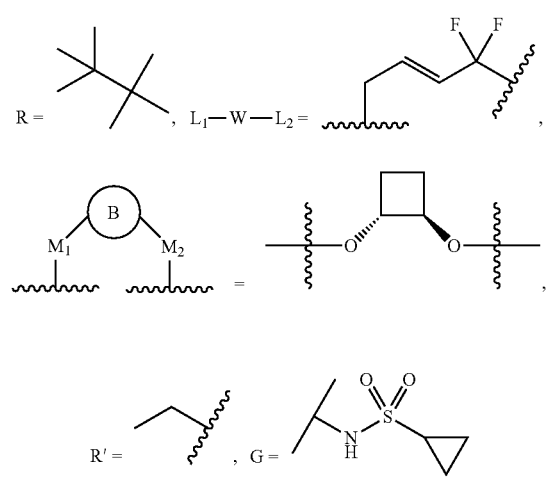

Following procedure described in the preparation of example 4 (step 4a), acid 1-6b was converted to compound example 36. MS-ESI m/z 789.45 (M+H)⁺.

Example 40

Compound of Formula VIII, Wherein

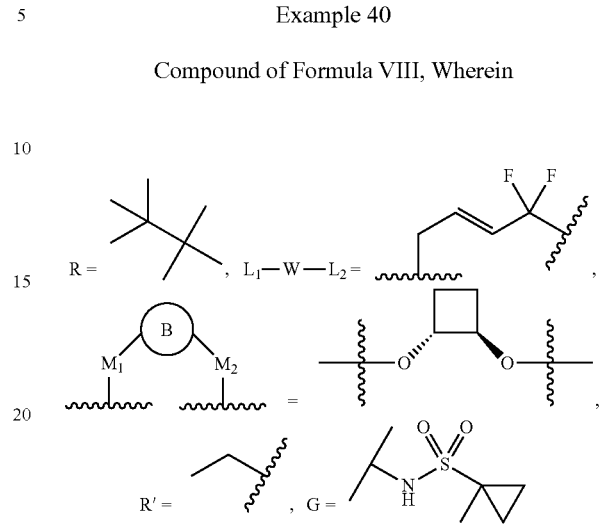

Following procedure described in the preparation of example 8 (step 8a), acid 1-6b was converted to compound example 40. MS-ESI m/z 803.47 (M+H)⁺.

Example 265

Compound of Formula X, Wherein

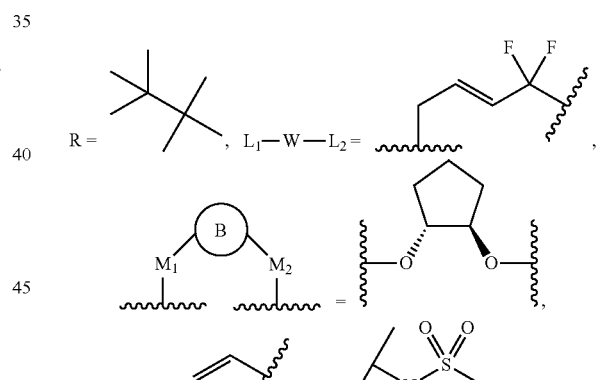

Step 265a

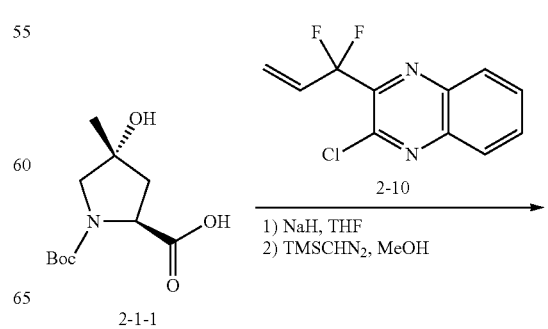

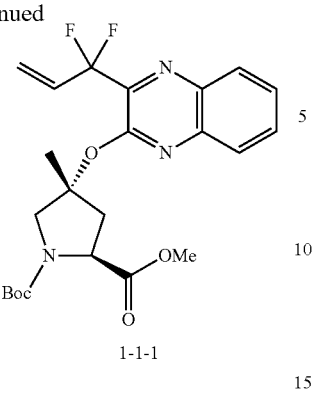

1-1-1

To a suspension of NaH (49 mg, 1.22 mmol, 60% in mineral oil) in THF was added a solution of 2-1-1 (0.1 g, 0.489 mmol) in THF (1.5 mL) at 0° C. After stirred at 0° C. for 45 min, a solution of 2-chloro-3-(1,1-difluoroallyl)quinoxaline 2-10 in THF (1 mL) was added and then the reaction mixture was heated at 60° C. for 3 h. Cooled to 0° C. and quenched with 2 N HCl at 0° C. The aqueous layer was extracted with DCM (3×), and the organic layer was combined, washed with water, brine, dried and concentrated in vacuo. To the residue in MeOH (5 ml) was added TMSCHN$_2$ (2 mL, 4 mmol, 2.0 M in Hexane) and the solution was stirred at rt for 30 min. Concentrated in vacuo. The residue was purified by flash chromatography with Hexane to 40% ethyl acetate in hexane to afford desired product 1-1-1 (82 mg, 43%). MS (ESI): m/z=464.21 [M+H].

Step 265b

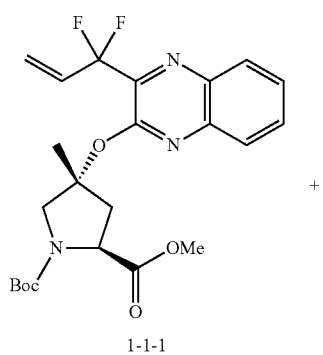

1-1-1

+

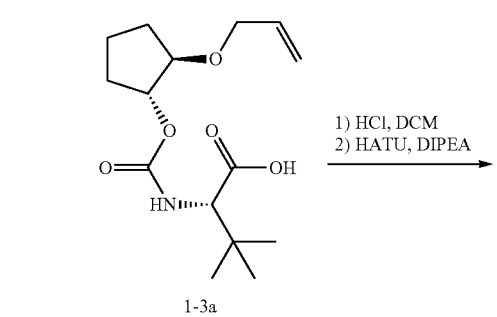

1-3a

1) HCl, DCM
2) HATU, DIPEA
→

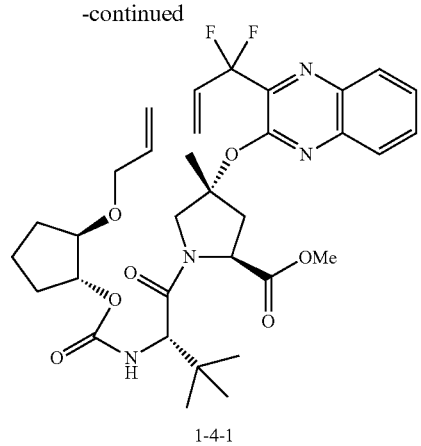

1-4-1

To a solution of quinoxaline derivative 1-1-1 (82 mg, 0.18 mmol) in DCM (3 mL) was added 4 N HCl (12 mL, in dioxane). The resulted solution was stirred for 2 h at 0° C. and solvent was removed in vacuo. To the residue in DCM (2 mL) was added acid 1-3a (69 mg, 0.23 mmol), HATU (133.8 mg, 0.352 mmol) and DIPEA (122.6 µL, 0.704 mmol). The mixture was diluted in DCM and washed with 10% citric acid, sat. NaHCO$_3$, brine, dried (Na$_2$SO$_4$) and concentrated in vacuo. The residue was purified by flash chromatography with Hexane to 40% EtOAc in hexane to afford diene 1-4-1 (129.5 mg, >99%). MS-ESI m/z 645.33 (M+H)$^+$.

Step 265c

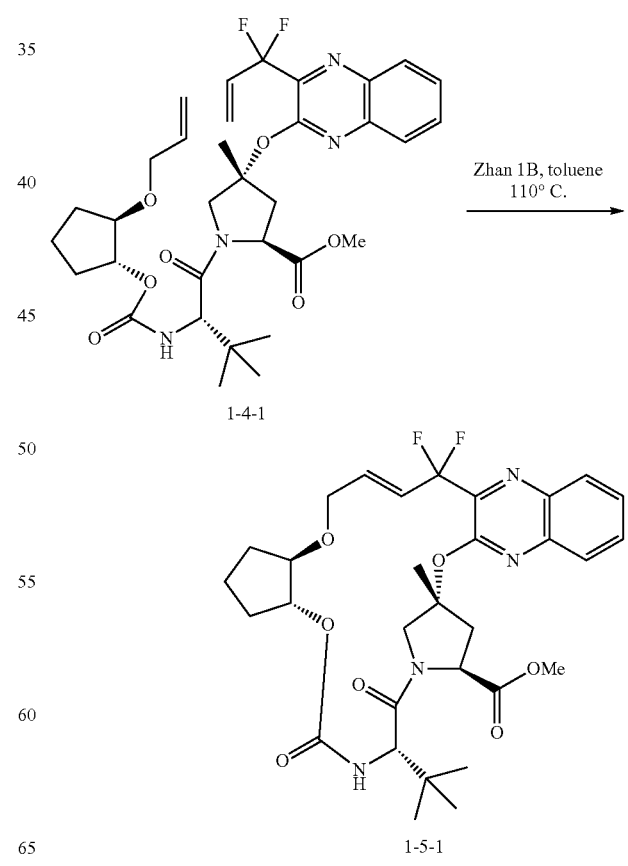

1-4-1

Zhan 1B, toluene
110° C.
→

1-5-1

To a solution of the diene 1-4-1 (110 mg, 0.17 mmol) in toluene under nitrogen atmosphere at 110° C. was added Zhan 1B catalyst (17.9 mg, 0.026 mmol) and the resulted solution was stirred at 110° C. for 5 h. The mixture was concentrated in vacuo and the residue was purified by flash chromatography with Hexane to 40% EtOAc in hexane to afford the alkene 1-5-1 (38 mg, 36%). MS-ESI m/z 617.32 (M+H)$^+$.

Step 265d

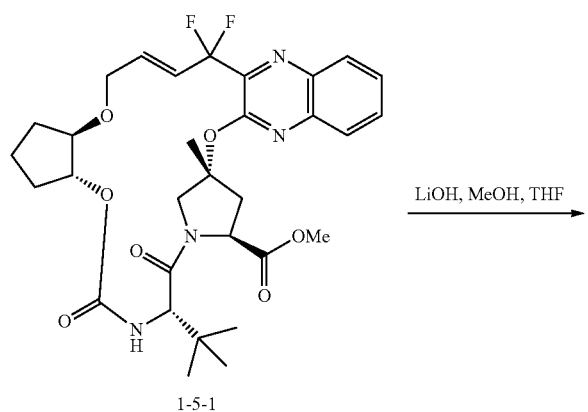

1-5-1

LiOH, MeOH, THF →

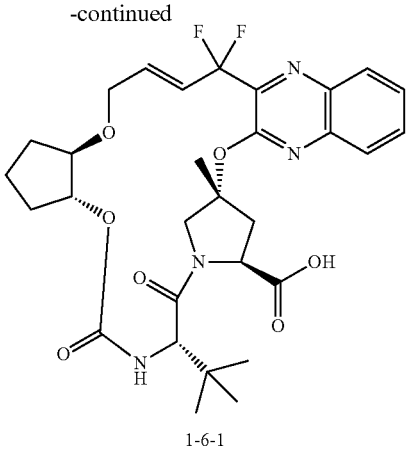

1-6-1

To a solution of the ester 1-5-1 (38 mg, 0.062 mmol) in MeOH (3 mL) and THF (6 mL) was added LiOH solution (3 mL, 1 N). The resulted mixture was stirred for 9 h at 0° C. ~rt and quenched with 1 N HCl at 0° C. The mixture was extracted with DCM (3×), and the organic layer was combined, washed with brine, dried (Na$_2$SO$_4$) and concentrated in vacuo to afford the acid 1-6-1. The acid was used to the next step without further purification.

Step 265e

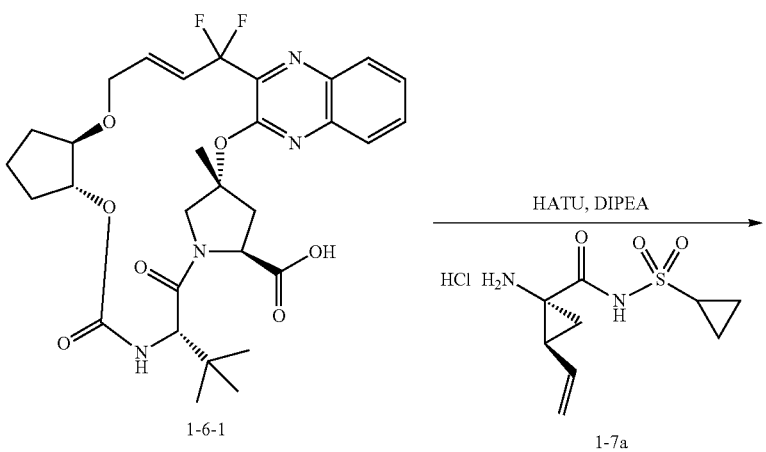

1-6-1

HATU, DIPEA →

1-7a

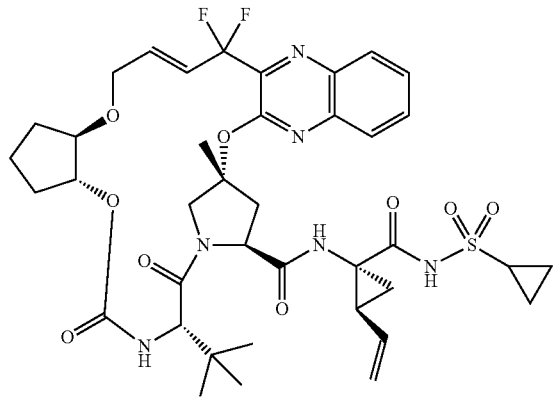

example 265

The acid 1-6-1 (9.8 mg, 0.0166 mmol) was dissolved in DCM (1.0 mL), and to this solution was added sulfonamide 1-7a (6.2 mg, 0.0216 mmol), HATU (9.5 mg, 0.0216 mmol) and DIPEA (5.8 μL, 0.0249 mmol). The mixture was stirred for 3 h, and then diluted with DCM. The organic layer was washed with 10% citric acid, sat. NaHCO$_3$, brine, dried (Na$_2$SO$_4$) and concentrated in vacuo. The residue was purified by preparative TLC 50% EtOAc in hexane afford the title compound (2.0 mg, 20%). MS-ESI m/z 815.30 (M+H)$^+$.

Example 266

Compound of Formula X, Wherein

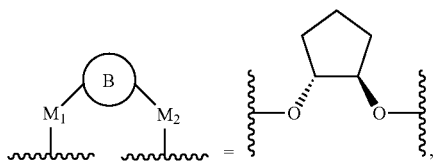

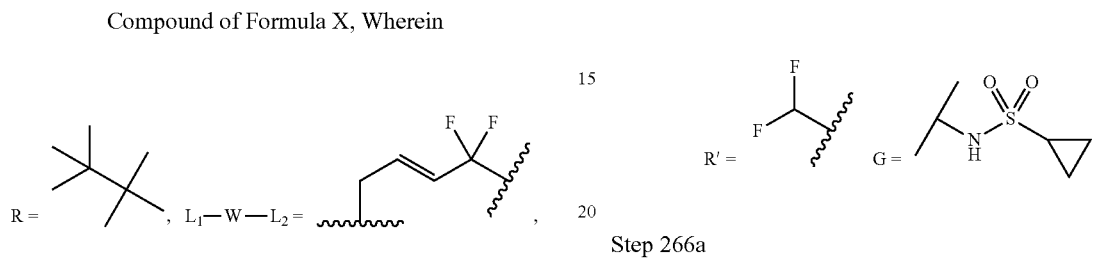

Step 266a

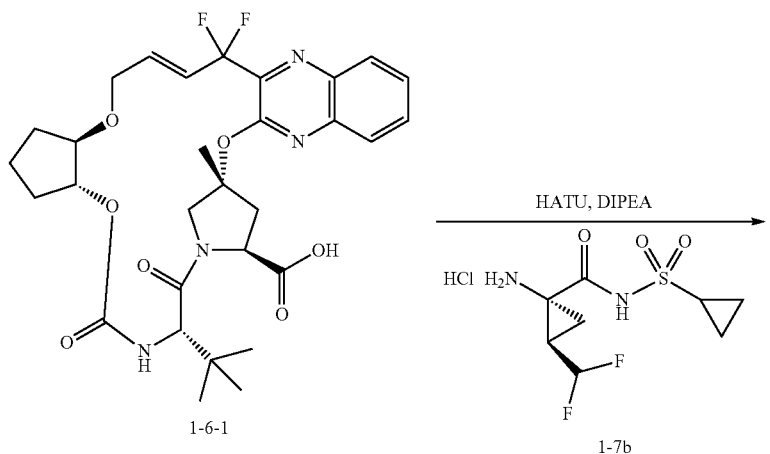

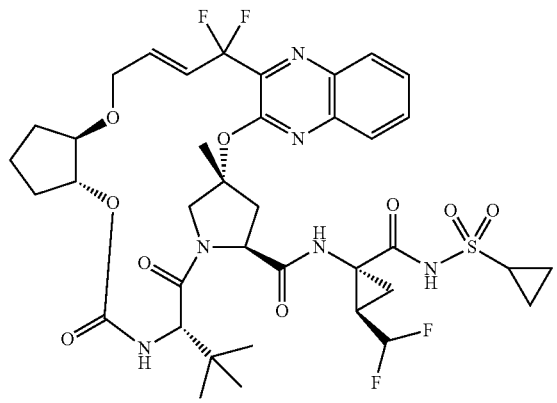

example 266

The acid 1-6-1 (crude product from step 266d) was dissolved in DCM (1 mL), and to this solution was added sulfonamide 1-7b (10.2 mg, 0.035 mmol), HATU (13.3 mg, 0.035 mmol) and DIPEA (12.2 µL, 0.07 mmol). The mixture was stirred for 3 h, and then diluted with DCM. The organic layer was washed with 10% citric acid, sat. NaHCO$_3$, brine, dried (Na$_2$SO$_4$) and concentrated in vacuo. The residue was purified by preparative TLC 50% EtOAc in hexane afford the title compound (3 mg, 30%). MS-ESI m/z 839.38 (M+H)$^+$.

Example 268

Compound of Formula X, Wherein

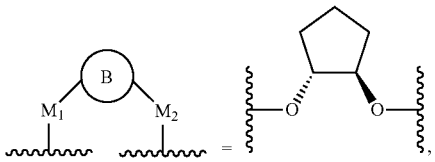

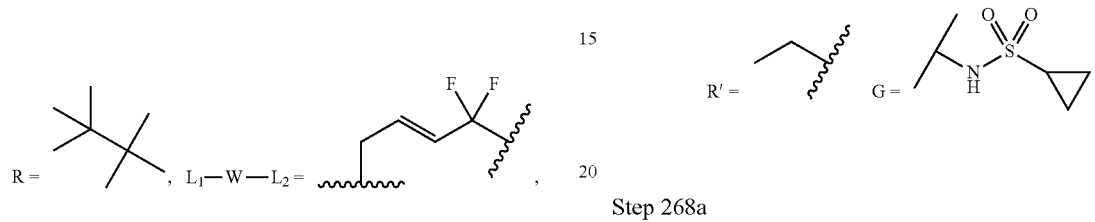

Step 268a

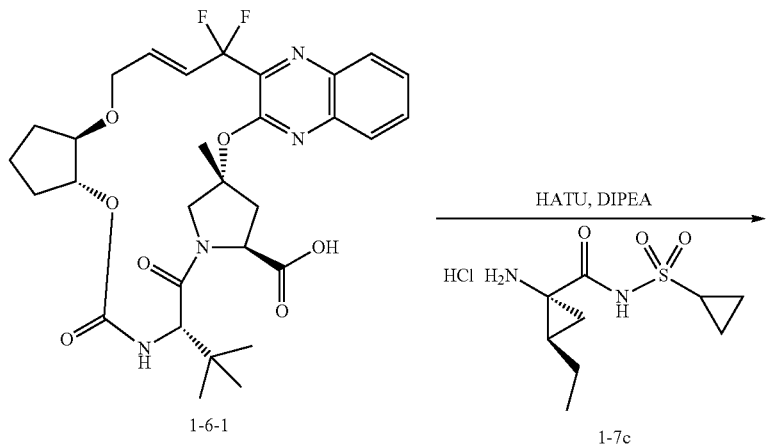

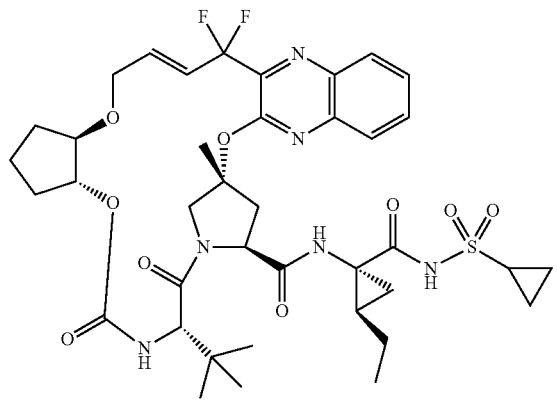

example 268

The acid 1-6-1 was dissolved in DCM (1 mL), and to this solution was added sulfonamide 1-7c (12.4 mg, 0.0463 mmol), HATU (17.6 mg, 0.0462 mmol) and DIPEA (12.4 uL, 0.0712 mmol). The mixture was stirred for 3 h, and then diluted with DCM. The organic layer was washed with 10% citric acid, sat. NaHCO₃, brine, dried (Na₂SO₄) and concentrated in vacuo. The residue was purified by preparative TLC 50% EtOAc in hexane afford the title compound (2.6 mg, 25%). MS-ESI m/z 816.91 (M+H)$^+$.

Example 273

Compound of Formula XI, Wherein

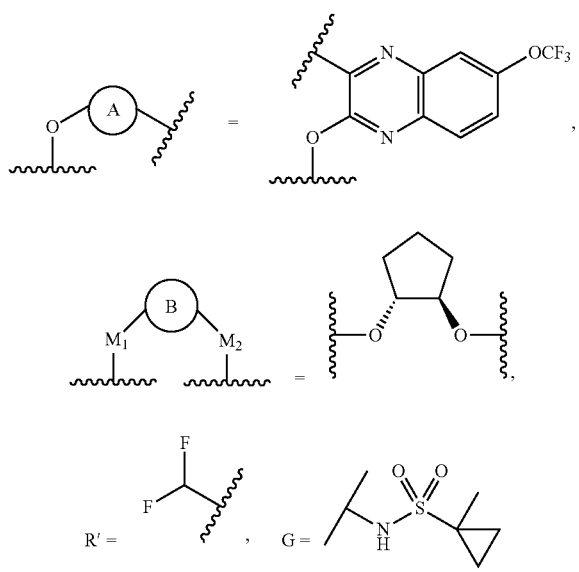

Step 273a

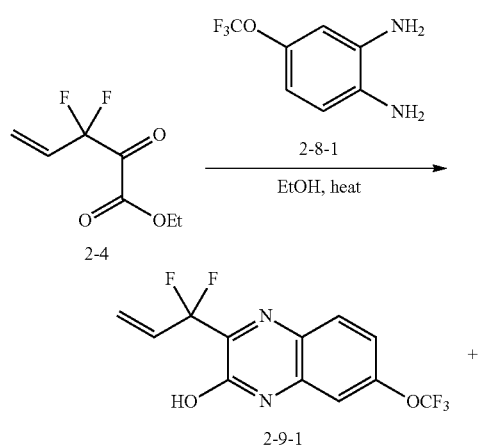

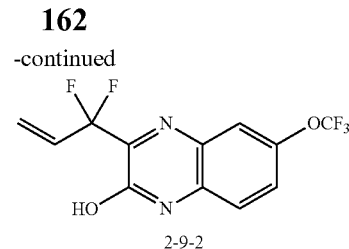

2-9-2

To the solution of ethyl 3,3-difluoro-2-oxopent-4-enoate 2-4 (0.417 g, 2.34 mmol) in EtOH (12 ml) was added 2-amino-4-(trifluoromethoxy)aniline 2-8-1 0.54 g, 2.81 mmol). The resulted mixture was heated to reflux for 14 h and then cool down to rt, the mixture was diluted by ethyl acetate, washed by 1M HCl, water, and brine. The solvent was removed and the crude product was purified by combiflash (12 g silica gel, 0-50% EA in Hexanes) to give 2-9-1 (0.228 g, 0.745 mmol, 31.8% yield) and 2-9-2 (0.358 g, 1.169 mmol, 49.9% yield).

Step 273b

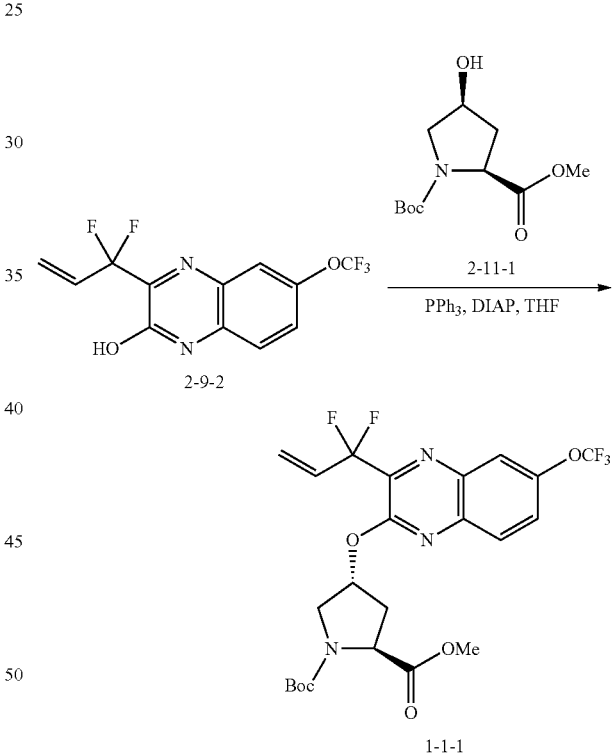

To the solution of 2-9-2 (0.228 g, 0.745 mmol), (2S,4S)-1-tert-butyl 2-methyl 4-hydroxypyrrolidine-1,2-dicarboxylate (0.219 g, 0.894 mmol) and Triphenylphosphine (0.293 g, 1.117 mmol) in THF (3.72 ml), the Diisopropyl azodicarboxylate (0.217 ml, 1.117 mmol) was added dropwise at room temperature. The mixture was stirred at room temperature for 2 h. The mixture was concentrated. The crude product was purified by combiflash (25 g silica gel, 0-40% ethyl acetate in Hexanes) to give 1-1-1 (0.320 g, 0.600 mmol, 81% yield). MS-ESI, m/z=534.45 (M+1)$^+$.

Step 273c

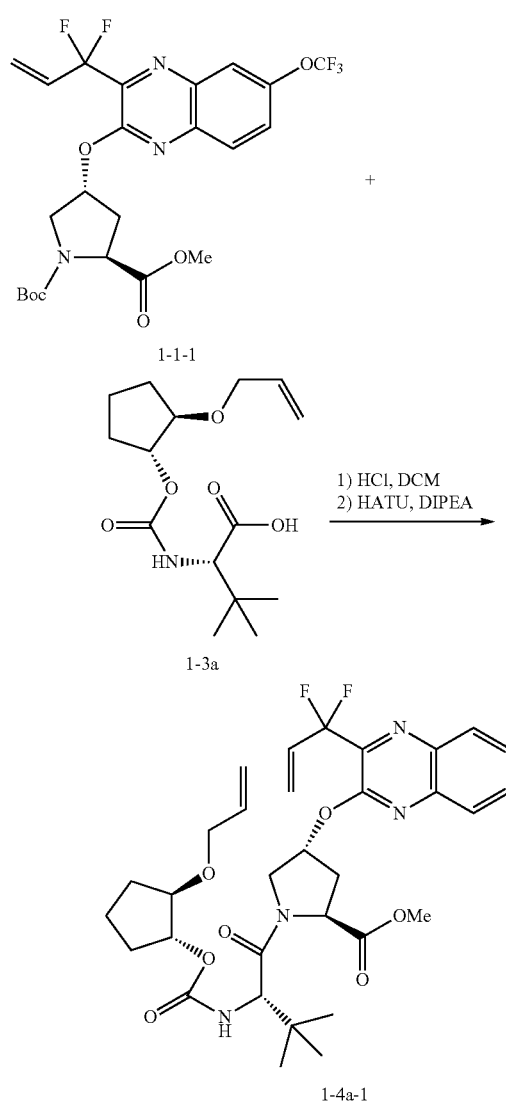

The compound 1-4a-1 was prepared by following the procedure described in the preparation of example 1 (step 1g). MS-ESI m/z 715.3 (M+H)⁺.

Step 273d

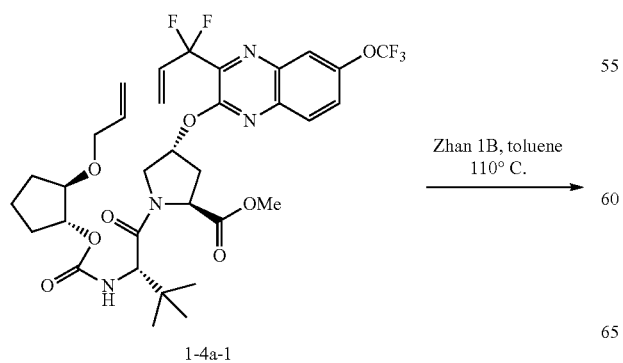

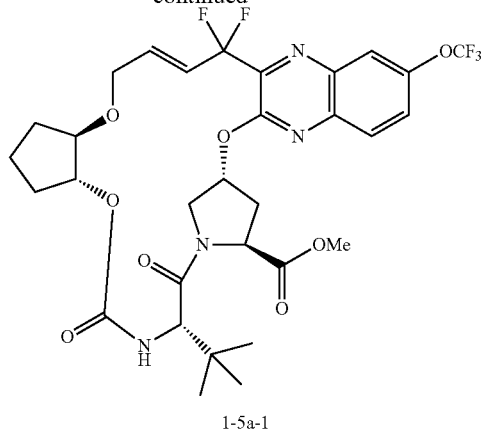

The compound 1-5a-1 was prepared by following the procedure described in the preparation of example 1 (step 1h). MS-ESI m/z 687.4 (M+H)⁺.

Step 273e

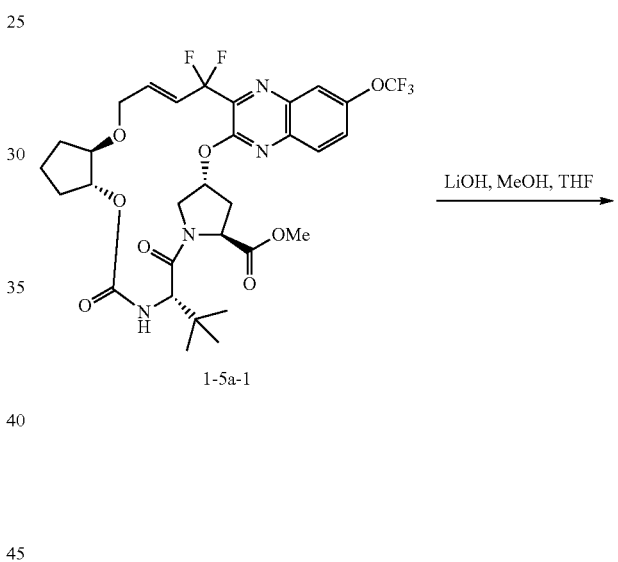

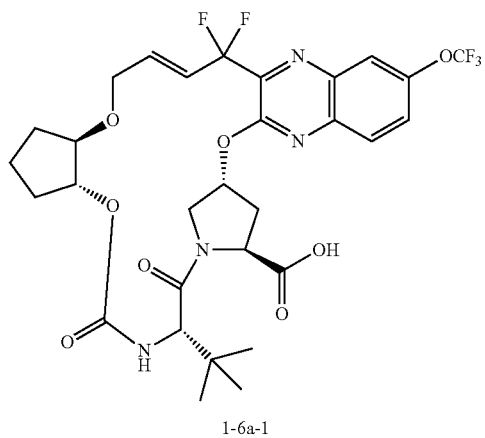

The compound 1-6a-1 was prepared by following the procedure described in the preparation of example 1 (step 1i). MS-ESI m/z 673.3 (M+H)⁺.

Step 273f
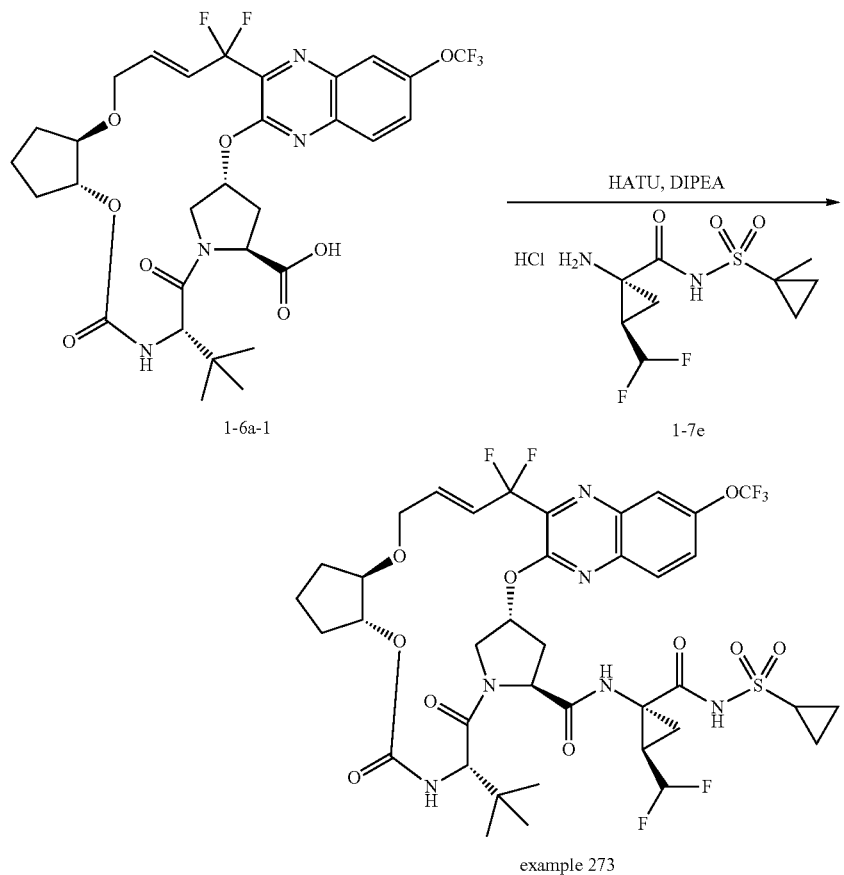
1-6a-1 1-7e
example 273
The compound of example 273 was prepared by following the procedure described in the preparation of example 1 (step 1j). MS-ESI m/z 923.4 (M+H)$^+$.
Example 274
Compound of Formula XI, Wherein
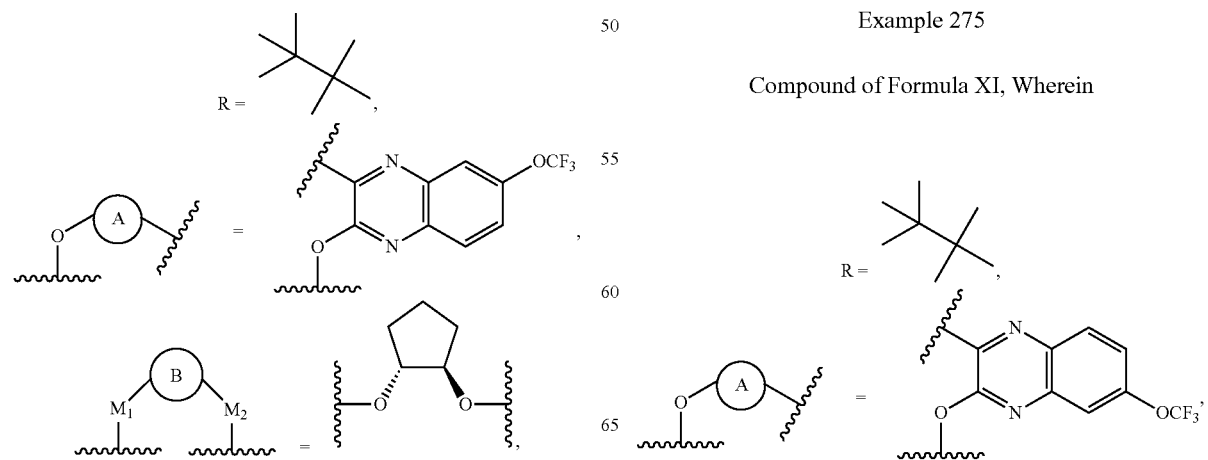
The compound of example 274 was prepared by following the procedure described in the preparation of example 273. MS-ESI m/z 899.3 (M+H)$^+$.
Example 275
Compound of Formula XI, Wherein -continued

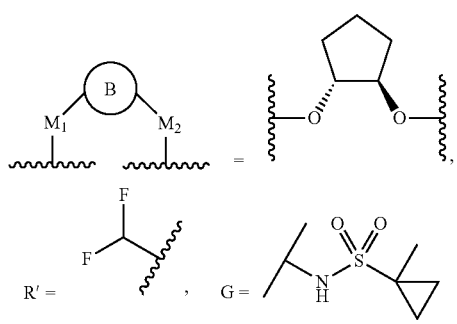

The compound of example 275 was prepared by following the procedure described in the preparation of example 273. MS-ESI m/z 923.4 (M+H)+.

Example 276

Compound of Formula XI, Wherein

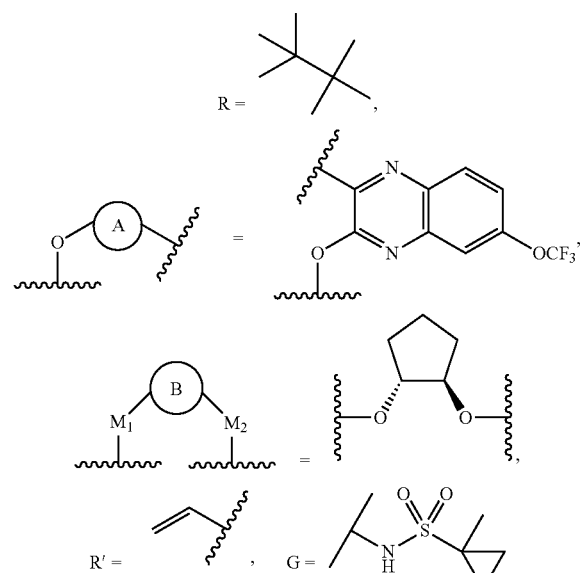

The compound of example 276 was prepared by following the procedure described in the preparation of example 273. MS-ESI m/z 899.3 (M+H)+.

Example 277

Compound of Formula XI, Wherein

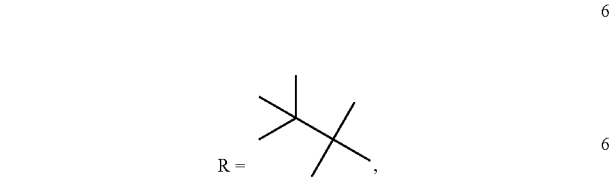

-continued

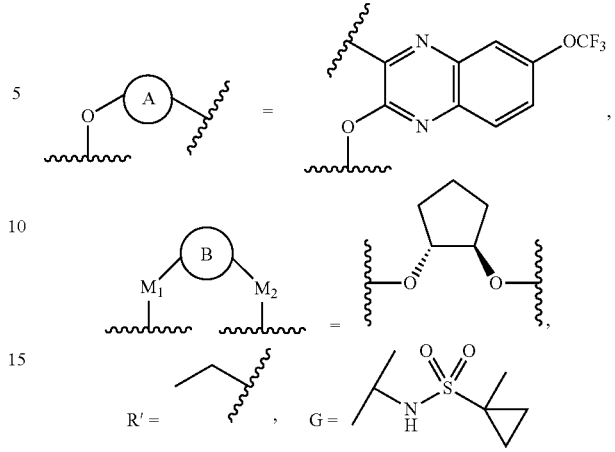

The compound of example 277 was prepared by following the procedure described in the preparation of example 273. MS-ESI m/z 833.4 (M+H)+.

Example 278

Compound of Formula XI, Wherein

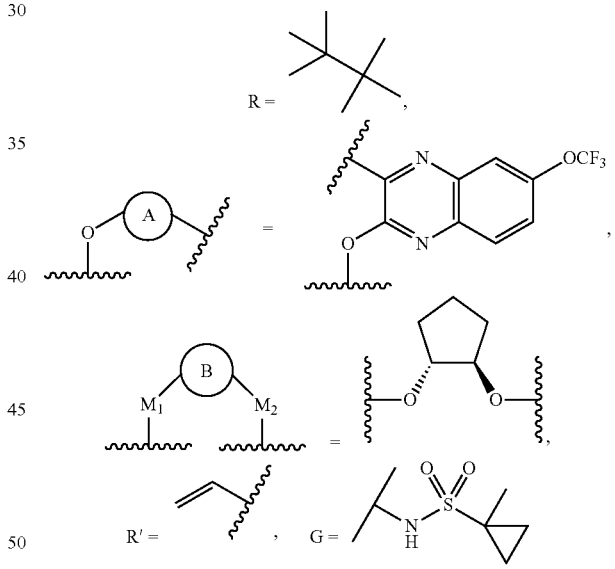

The compound of example 278 was prepared by following the procedure described in the preparation of example 273. MS-ESI m/z 831.4 (M+H)+.

Example 279

Compound of Formula XI, Wherein

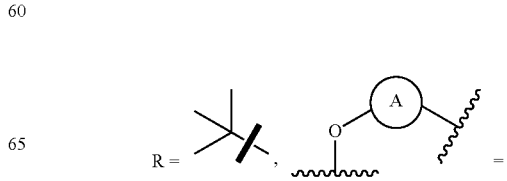

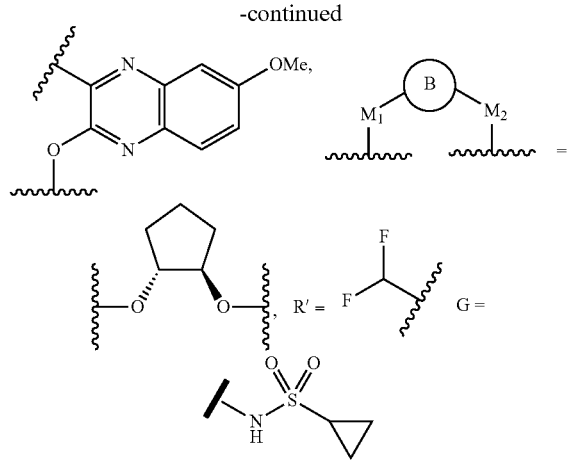

The compound of example 279 was prepared by following the procedure described in the preparation of example 273. MS-ESI m/z 855.4 (M+H)⁺.

Example 280

Compound of Formula XI, Wherein

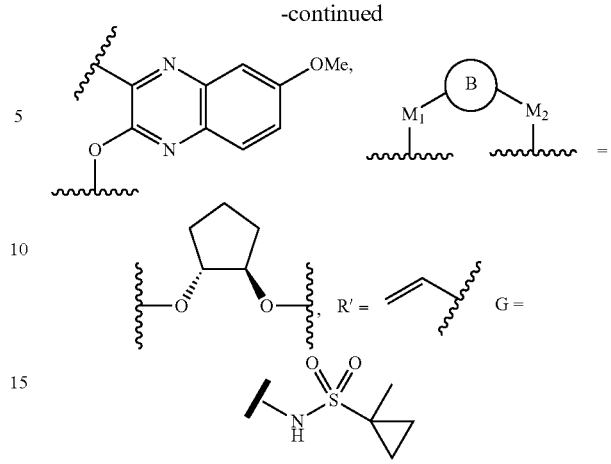

The compound of example 281 was prepared by following the procedure described in the preparation of example 273. MS-ESI m/z 845.4 (M+H)⁺.

Example 282

Compound of Formula XI, Wherein

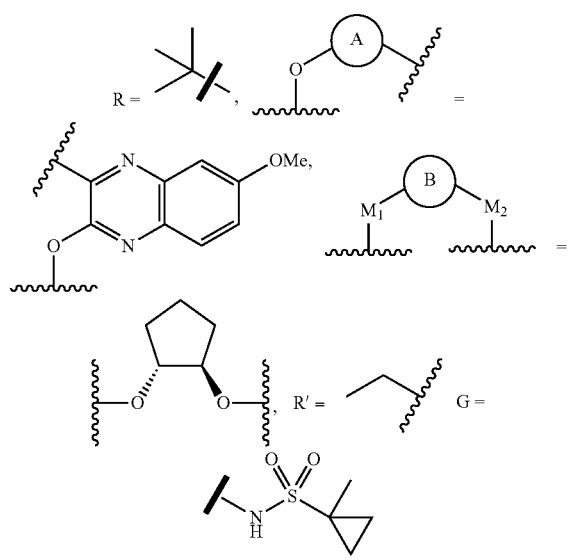

The compound of example 280 was prepared by following the procedure described in the preparation of example 273. MS-ESI m/z 847.4 (M+H)⁺.

Example 281

Compound of Formula XI, Wherein

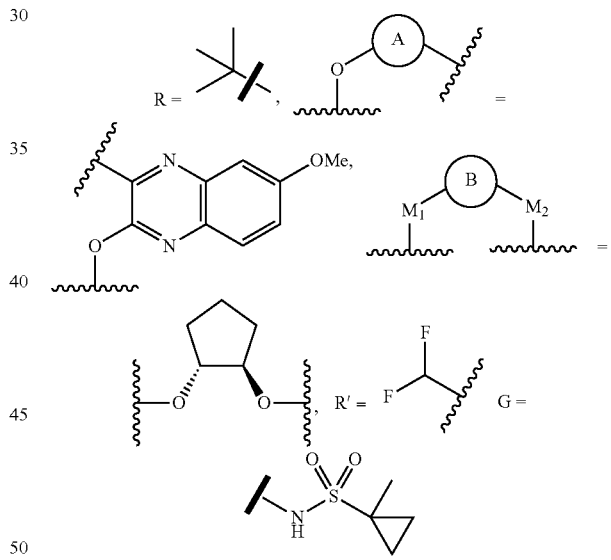

The compound of example 282 was prepared by following the procedure described in the preparation of example 273. MS-ESI m/z 869.4 (M+H)⁺.

Example 283

Compound of Formula XI, Wherein

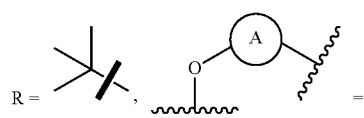

-continued

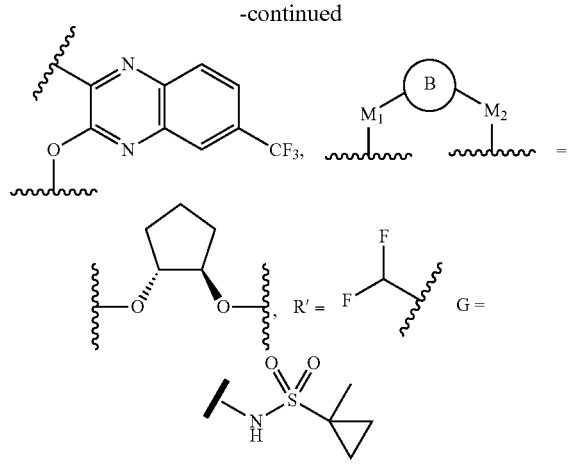

The compound of example 283 was prepared by following the procedure described in the preparation of example 273. MS-ESI m/z 906.3 (M+H)$^+$.

Example 284

Compound of Formula XI, Wherein

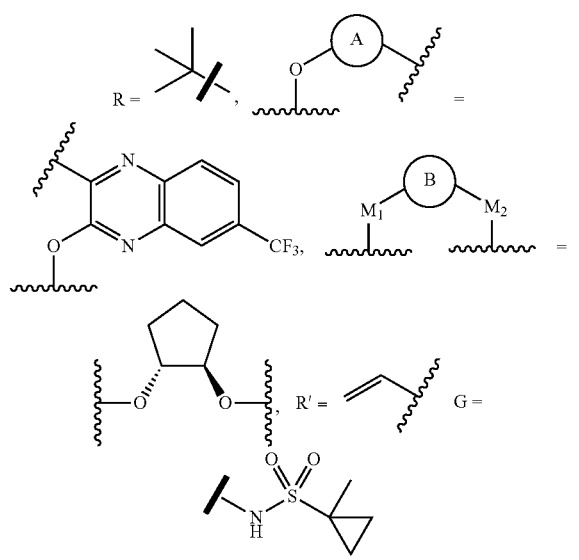

The compound of example 284 was prepared by following the procedure described in the preparation of example 273. MS-ESI m/z 883.4 (M+H)$^+$.

Example 285

Compound of Formula XI, Wherein

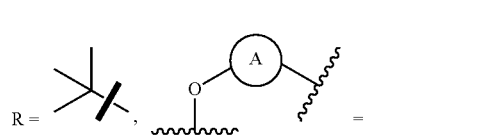

-continued

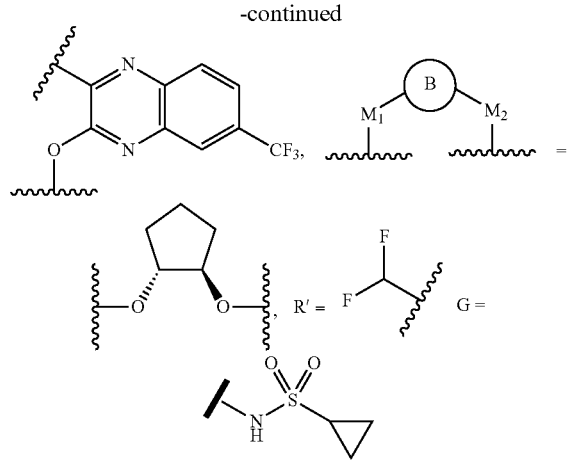

The compound of example 285 was prepared by following the procedure described in the preparation of example 273. MS-ESI m/z 893.3 (M+H)$^+$.

Example 286

Compound of Formula XI, Wherein

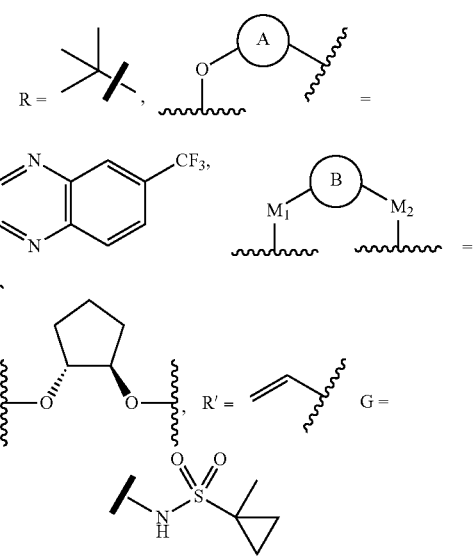

The compound of example 286 was prepared by following the procedure described in the preparation of example 273. MS-ESI m/z 883.4 (M+H)$^+$.

Example 287

Compound of Formula XI, Wherein

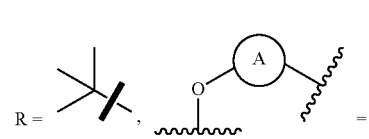

-continued

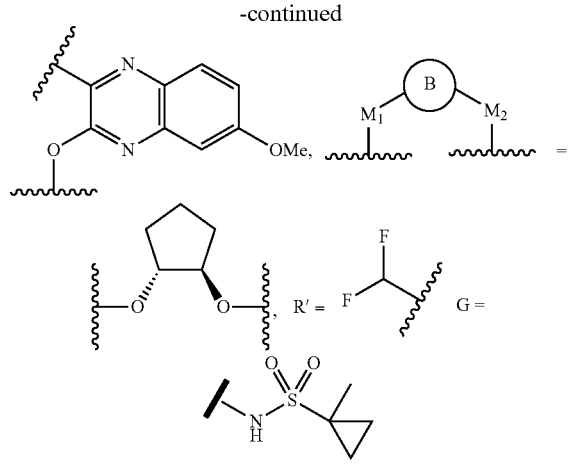

The compound of example 287 was prepared by following the procedure described in the preparation of example 273. MS-ESI m/z 868.4 (M+H)+.

Example 288

Compound of Formula XI, Wherein

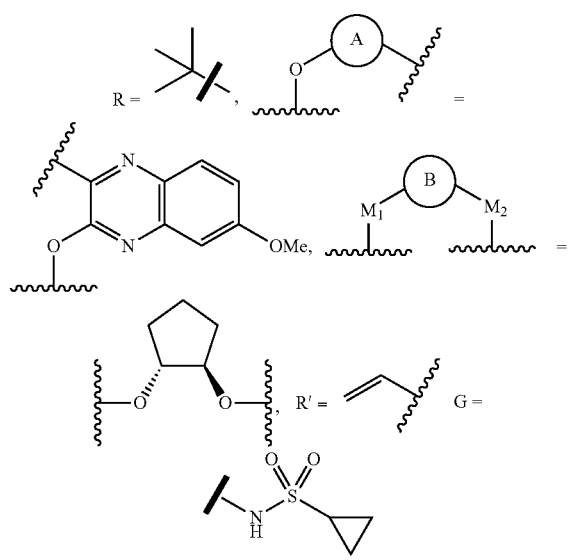

The compound of example 288 was prepared by following the procedure described in the preparation of example 273. MS-ESI m/z 831.4 (M+H)+.

Example 289

Compound of Formula XI, Wherein

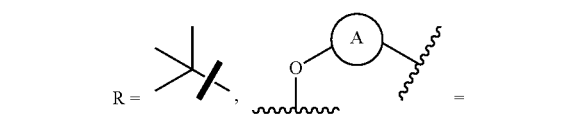

-continued

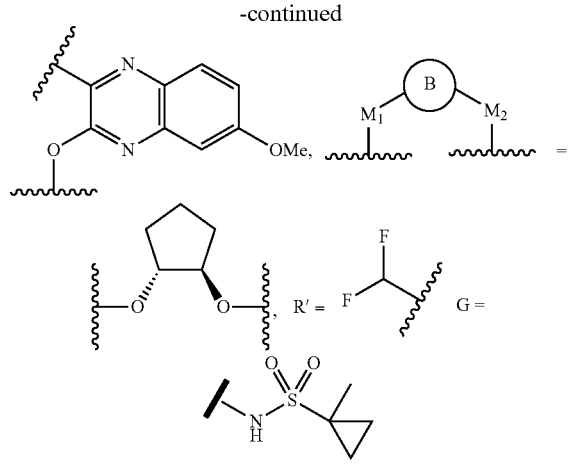

The compound of example 289 was prepared by following the procedure described in the preparation of example 273. MS-ESI m/z 845.4 (M+H)+.

Example 290

Compound of Formula XI, Wherein

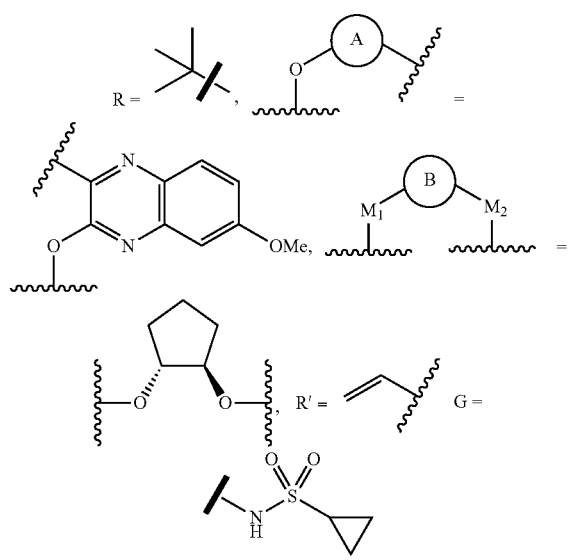

The compound of example 290 was prepared by following the procedure described in the preparation of example 273. MS-ESI m/z 889.4 (M+H)+.

Example 291

Compound of Formula XI, Wherein

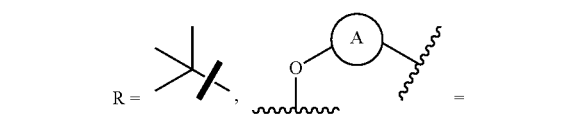

-continued

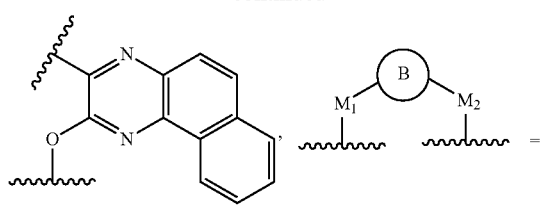

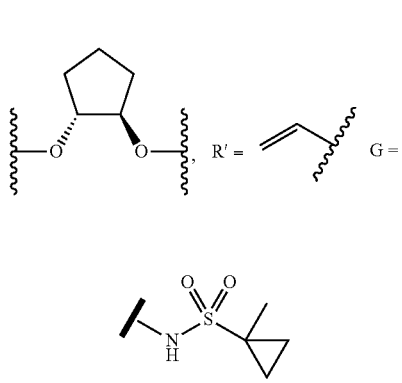

The compound of example 291 was prepared by following the procedure described in the preparation of example 273. MS-ESI m/z 865.4 (M+H)+.

Example 292

Compound of Formula XI, Wherein

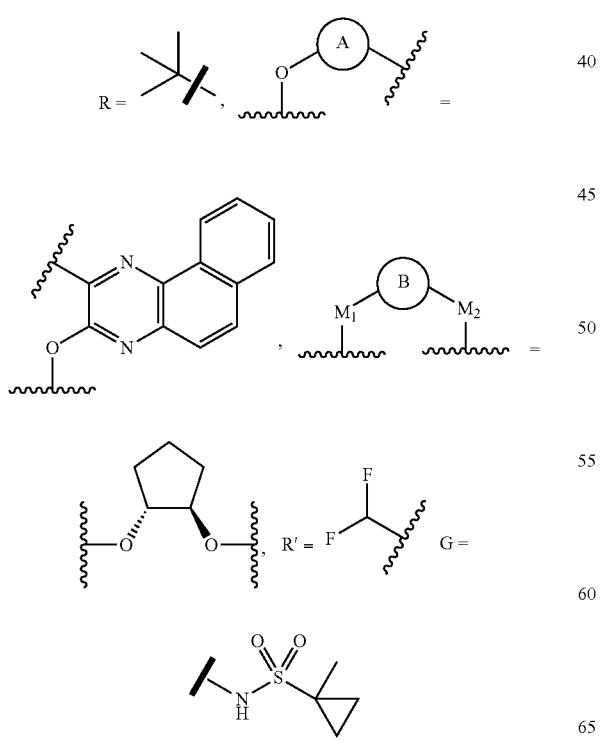

The compound of example 292 was prepared by following the procedure described in the preparation of example 273. MS-ESI m/z 889.4 (M+H)+.

Example 293

Compound of Formula XI, Wherein

The compound of example 293 was prepared by following the procedure described in the preparation of example 273. MS-ESI m/z 865.4 (M+H)+.

Example 294

Compound of Formula XI, Wherein

The compound of example 294 was prepared by following the procedure described in the preparation of example 273. MS-ESI m/z 833.4 (M+H)+.

Example 295

Compound of Formula XI, Wherein

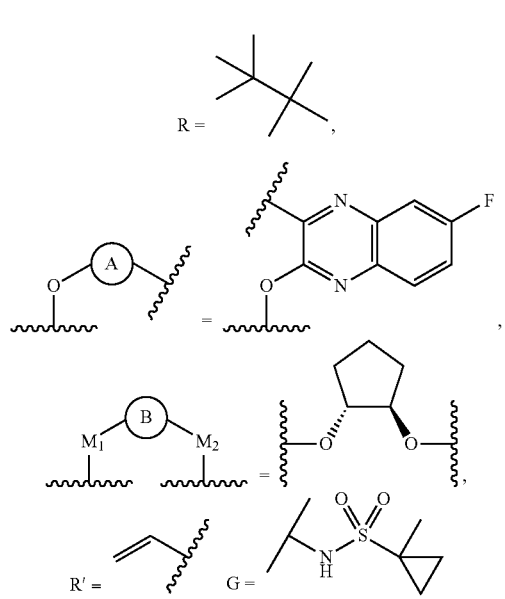

The compound of example 295 was prepared by following the procedure described in the preparation of example 273. MS-ESI m/z 833.4 (M+H)+.

Example 296

Compound of Formula XI, Wherein

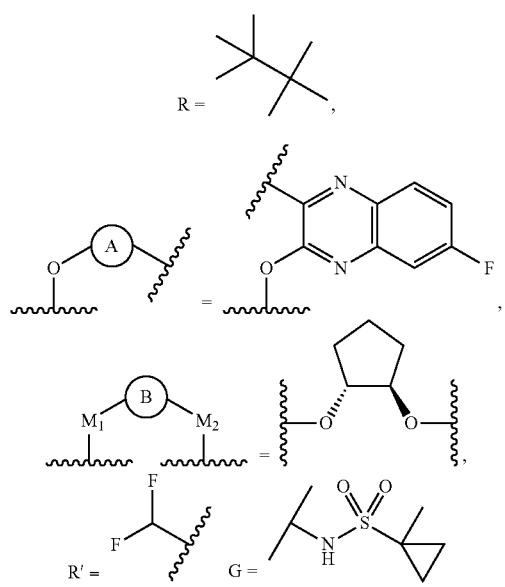

The compound of example 296 was prepared by following the procedure described in the preparation of example 273. MS-ESI m/z 857.3 (M+H)+.

Example 297

Compound of Formula XI, Wherein

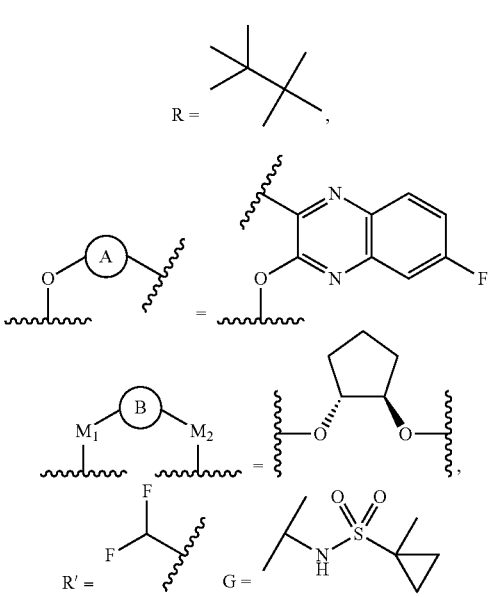

The compound of example 297 was prepared by following the procedure described in the preparation of example 273. MS-ESI m/z 843.3 (M+H)+.

The compounds of the present invention exhibit potent inhibitory properties against the HCV NS3 protease. The following examples describe assays in which the compounds of the present invention can be tested for anti-HCV effects.

Example 301

Biological Assays

Each compound's anti-HCV activity can be determined by measuring the activity of the luciferase reporter gene in the replicon in the presence of 5% FBS. The luciferase reporter gene, and selectable marker gene for replicons stably maintained in cell lines, is placed under the translational control of the poliovirus IRES instead of the HCV IRES, and HuH-7 cells are used to support the replication of the replicon.

The inhibitory activities of the compounds of the present invention can be evaluated using a variety of assays known in the art. For instance, stable subgenomic replicon cell lines can be used for compound characterization in cell culture, including those derived from genotypes 1a-H77, 1b-N and 1b-Con1, obtained from University of Texas Medical Branch, Galveston, Tex. (1a-H77 and 1b-N) or Apath, LLC, St. Louis, Mo. (1b-Con1). Chimeric replicons using the genotype 1a or 1b replicons with insertion of NS3 genes from isolates from humans infected with genotypes 1a or 1b can be used to measure inhibitory activity against a panel of the target protein from natural isolates. Chimeric replicons using the genotype 1a or 1b replicons with insertion of NS3 genes from isolates from humans infected with genotypes 3a, 4 or 6 can be used to measure inhibitory activity against representatives of those genotypes. The genotype 1a replicon construct contains the NS3-NS5B coding region derived from the H77 strain of HCV (1a-H77). The replicon also has a firefly luciferase reporter and a neomycin phosphotransferase (Neo) selectable marker. These two coding regions, separated by the FMDV 2a protease, comprise the first cistron of the bicistronic replicon construct, with the second cistron containing the NS3-NS5B coding region with addition of adaptive mutations E1202G, K1691R, K2040R and S2204I. The 1b-Con1 and 1b-N replicon constructs are identical to the 1a-H77 replicon, except that the HCV 5' UTR, 3' UTR, and NS3-NS5B coding region are derived from the 1b-Con1 or 1b-N strain, and the adaptive mutations are K1609E, K1846T and Y3005C for 1b-Con1 or A1098T, E1202G, and S2204I for 1b-N. In addition, the 1b-Con1 replicon construct contains a poliovirus IRES between the HCV IRES and the luciferase gene. Replicon cell lines can be maintained in Dulbecco's modified Eagles medium (DMEM) containing 10% (v/v) fetal bovine serum (FBS), 100 IU/ml penicillin, 100 mg/ml streptomycin (Invitrogen), and 200 mg/ml G418 (Invitrogen).

The inhibitory effects of the compounds of the invention on HCV replication can also be determined by measuring activity of the luciferase reporter gene encoded by subgenomic replicons not containing the Neo selectable marker, that are transiently expressed in cells. The adaptive mutations encoded by the 1a-H77, 1b-N and 1b-Con-1 replicons are the same as listed above. The 1b-Con1 replicon used for these transient assays contains the NS2-NS5B coding region rather than the NS3-5B coding region. These replicons may encode target NS3 genes as described for stable subgenomic replicons or they may encode amino acid variants that confer varying degrees of susceptibility to the drug. For example, variants could include R155K, D168E or D168V in a genotype 1a NS3 gene; R155K or D168V in a genotype 1b NS3 gene; S138T, A166T or Q168R in a genotype 3a NS3 gene. For example, cells can be transfected with the replicon by electroporation and seeded into 96 well plates at a density of 5000 cells per well in 100 µl DMEM containing 5% FBS. Compounds diluted in dimethyl sulfoxide (DMSO) to generate a 200× stock in a series of eight half-log dilutions can then be further diluted 100-fold in the medium containing 5% FBS and added to the cell culture plates already containing 100 µl of DMEM with 5% FBS. After an incubation period of either 3 or 4 days, 30 µl of Passive Lysis buffer (Promega) can be added to each well, with incubation for 15 minutes with rocking to lyse the cells. Luciferin solution (100 µl, Promega) can be added to each well, and luciferase activity can be measured with a luminometer. The percent inhibition of HCV RNA replication can be calculated for each compound concentration and the $EC_{50}$ value can be calculated using nonlinear regression curve fitting to the 4-parameter logistic equation and GraphPad Prism 4 software.

When tested using genotype 1a Huh-7 stable replicon assays, compounds of Examples 1, 4, 5, 6, 8, 275, 276, 283, 284, 287, 288, 289, 290, 291, 294, 295, 296, and 297 showed $EC_{50}$ values of less than 1 nM; compounds of Examples 2, 36, 40, 65, 89, 90, 273, 274, 280, 285, 292, 293, 298, and 299 showed $EC_{50}$ values of from 1 to 10 nM; and compounds of Example 34 showed $EC_{50}$ values of from 10 to 100 nM.

When tested using genotype 1b Con1 stable replicon assays, compounds of Examples 275, 276, 283, 290, 294, 295, and 296 showed $EC_{50}$ values of less than 1 nM; and compounds of Examples 1, 2, 4, 5, 6, 8, 34, 36, 40, 65, 89, 90, 273, 274, 279, 280, 281, 284, 285, 287, 288, 289, 291, 292, 293, 297, 298, and 299 showed $EC_{50}$ values of from 1 to 10 nM.

When tested using genotype 1a wild-type transient replicon assays, compounds of Examples 5, 6, 275, 276, 283, 284, 287, 288, 289, 291, 294, 295, and 297 showed $EC_{50}$ values of less than 0.1 nM; compounds of Examples 1, 2, 4, 8, 277, 280, 281, 282, 285, 286, 292, 293, 296, 298, and 299 showed $EC_{50}$ values of from 0.1 to 1 nM; and compounds of Examples 34, 36, and 40 showed $EC_{50}$ values of from 1 to 10 nM.

When tested using genotype 1a R155K transient replicon assays, compounds of Examples 2, 5, 6, 8, 275, 276, 281, 283, 284, 287, 288, 289, 291, 294, 295, 296, and 297 showed $EC_{50}$ values of less than 0.1 nM; compounds of Examples 1, 4, 277, 280, 282, 285, 286, 292, 293, and 299 showed $EC_{50}$ values of from 0.1 to 1 nM; and compounds of Examples 34, 40, 36, and 298 showed $EC_{50}$ values of from 1 to 10 nM.

When tested using genotype 1a D168E transient replicon assays, compounds of Examples 1, 2, 4, 5, 6, and 8 showed $EC_{50}$ values of less than 1 nM; and compounds of Examples 40, 298, and 299 showed $EC_{50}$ values of from 1 to 100 nM.

When tested using genotype 1a D168V transient replicon assays, compounds of Examples 2, 5, 6, 276, 281, 287, 288, 289, 291, 292, 295, 296, and 297 showed $EC_{50}$ values of less than 1 nM; compounds of Examples 1, 8, 275, 280, 282, 283, 284, and 293 showed $EC_{50}$ values of from 1 to 10 nM; and compounds of Examples 4, 36, 40, 277, 285, 286, 298, and 299 showed $EC_{50}$ values of from 10 nM to 1 µM.

When tested using genotype 1b wild-type transient replicon assays, compounds of Examples 1, 2, 4, 5, 6, 8, 275, 276, 281, 282, 283, 284, 285, 286, 287, 288, 289, 291, 292, 293, 294, 295, 296, and 297 showed $EC_{50}$ values of less than 1 nM; and compounds of Examples 34, 36, 40, 277, 280, 298, and 299 showed $EC_{50}$ values of from 1 to 10 nM.

When tested using genotype 1b R155K transient replicon assays, compounds of Examples 1, 2, 4, 5, 6, and 8 showed $EC_{50}$ values of less than 1 nM; and compounds of Examples 34, 36, 40, 298, and 299 showed $EC_{50}$ values of from 1 to 10 nM.

When tested using genotype 1b D168V transient replicon assays, compounds of Examples 1, 5, 6, 275, 276, and 282 showed $EC_{50}$ values of less than 1 nM; and compounds of Examples 2, 4, 8, 34, 36, 40, 280, 298, and 299 showed $EC_{50}$ values of from 1 to 100 nM.

When tested using genotype 3a wild-type stable replicon assays, compounds of Examples 1, 2, 5, 6, 275, 276, 280, 287, 288, 289, 290, 291, 294, and 296 showed $EC_{50}$ values of less than 10 nM; compounds of Examples 281, 282, 283, 284, 292, 293, 295, and 297 showed $EC_{50}$ values of from 10 to 100 nM; and compounds of Examples 273, 274, 277, 278, and 279 showed $EC_{50}$ values of from 100 nM to 1 µM.

When tested using genotype 3a wild-type transient replicon assays, compounds of Examples 2, 5, 6, 275, 276, 280, 283, 289, and 291 showed $EC_{50}$ values of less than 10 nM; compounds of Examples 1, 4, 8, 281, 282, 284, 285, and 293 showed $EC_{50}$ values of from 10 to 100 nM; and compounds of Examples 65, 90, 277, and 286 showed $EC_{50}$ values of from 100 nM to 1 μM.

When tested using genotype 3a A166T transient replicon assays, compounds of Examples 2, 5, and 6 showed $EC_{50}$ values of less than 100 nM; and compounds of Examples 1, 4, and 8 showed $EC_{50}$ values of from 100 to 500 nM.

When tested using genotype 3a Q168R transient replicon assays, compounds of Examples 5, 6, 275, 276, 280, 281, 282, 283, 289, 291, and 293 showed $EC_{50}$ values of less than 100 nM; and compounds of Examples 1, 2, 4, 8, 90, 277, 284, 285, and 286 showed $EC_{50}$ values of from 100 nM to 1 μM.

When tested using genotype 3a S138T transient replicon assays, compounds of Examples 5 and 6 showed $EC_{50}$ values of less than 100 nM; and compounds of Examples 1, 2, 4, 8, and 65 showed $EC_{50}$ values of from 100 nM to 1 μM.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

While this invention has been particularly shown and described with references to preferred embodiments thereof, it will be understood by those skilled in the art that various changes in form and details may be made therein without departing from the scope of the invention encompassed by the appended claims.

-continued
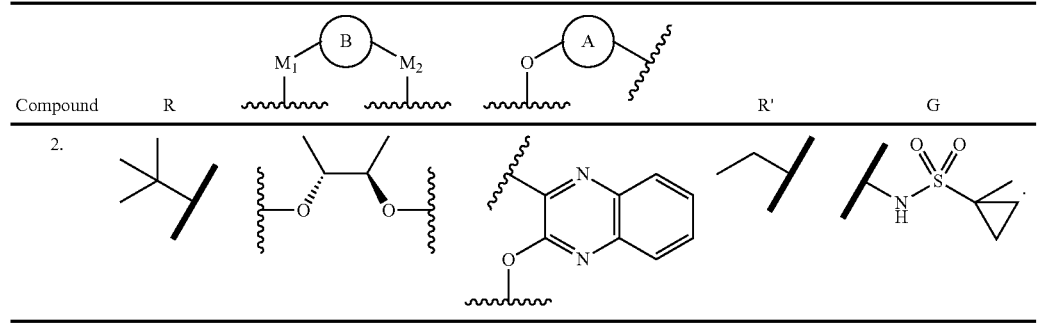

What is claimed:
1. A compound of Formula I:

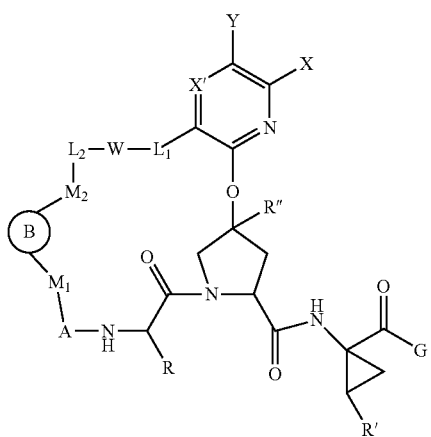

or a pharmaceutically acceptable salt thereof, wherein
A is absent, —(C=O)—, —S(O)$_2$-, —C(=N—OR$_1$)— or —C(=N—CN)—;

(B) is

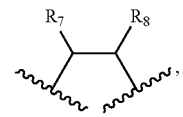

wherein $R_7$ and $R_8$ are each independently $C_1$-$C_8$ alkyl or $C_2$-$C_8$ alkenyl and are each independently optionally substituted with one or more halo;

$M_1$ and $M_2$ are each independently O or $NR_1$;

each $R_1$ is independently selected at each occurrence from the group consisting of:
(i) hydrogen;
(ii) aryl; substituted aryl; heteroaryl; or substituted heteroaryl;
(iii) heterocycloalkyl or substituted heterocycloalkyl; and
(iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;

$L_1$ and $L_2$ are each independently selected from —$C_1$-$C_8$ alkylene, —$C_2$-$C_8$alkenylene, or —$C_2$-$C_8$alkynylene each containing 0, 1, 2, or 3 heteroatoms selected from O, S, or N; substituted —$C_1$-$C_8$ alkylene, substituted —$C_2$-$C_8$alkenylene, or substituted —$C_{2-C8}$ alkynylene each containing 0, 1, 2, or 3 heteroatoms selected from O, S or N; —$C_3$-$C_{12}$cycloalkylene, or substituted —$C_3$-$C_{12}$ cycloalkylene each containing 0, 1, 2, or 3 heteroatoms selected from O, S or N; —$C_3$-$C_{12}$cycloalkenylene, and substituted —$C_3$-$C_{12}$cycloalkenylene each containing 0, 1, 2, or 3 heteroatoms selected from O, S or N;

W is absent, —O—, —S—, —NH—, —N(Me)-, —C(O)NH—, or —C(O)N(Me)-;

X and Y taken together with the carbon atoms to which they are attached to form a cyclic moiety which selected from aryl, substituted aryl, heteroaryl, substituted heteroaryl, heterocyclic, substituted heterocylic, carbocyclic, and substituted carbocyclic;

X' is N or —C(R$_2$)—, where R$_2$ is selected from the group consisting of:
(i) hydrogen, halogen, CN, CF$_3$, NO$_2$, OR$_3$, SR$_3$, —NHS(O)$_2$—R$_3$, —NH(SO$_2$)NR$_4$R$_5$, NR$_4$R$_5$, CO$_2$R$_3$, COR$_3$, CONR$_4$R$_5$, N(R$_1$)COR$_3$; aryl; substituted aryl; heteroaryl; or substituted heteroaryl;
(ii) heterocycloalkyl or substituted heterocycloalkyl; and
(iii) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$alkenyl, or substituted —$C_2$-$C_8$ alkynyl each containing 0, 1, 2, or 3 heteroatoms selected from O, S or N;

—$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;

each $R_3$ is independently selected from $C_1$-$C_8$ alkyl, —$C_2$-$C_8$alkenyl, or —$C_2$-$C_8$ alkynyl each containing 0, 1, 2, or 3 heteroatoms selected from O, S or N, substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; and —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl; heterocylic; substituted heterocyclic; aryl; substituted aryl; heteroaryl; or substituted heteroaryl;

each $R_4$ and $R_5$ are independently selected from H and $R_3$, or $R_4$ and $R_5$ combined together with the N they are attached to form a heterocyclic ring;

R and R' are each independently selected from the group consisting of:

(i) —$C_1$-$C_8$alkyl, —$C_2$-$C_8$alkenyl, or —$C_2$-$C_8$ alkynyl each containing 0, 1, 2, or 3 heteroatoms selected from O, S, or N; substituted —$C_1$-$C_8$alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, r substituted —$C_3$-$C_{12}$cycloalkyl; —$C_4$-$C_{12}$ alkylcycloalkyl, substituted —$C_4$-$C_{12}$ alkylcycloalkyl; —$C_3$-$C_{12}$ cycloalkenyl, substituted —$C_3$-$C_{12}$ cycloalkenyl; —$C_4$-$C_{12}$ alkylcycloalkenyl, or substituted —$C_4$-$C_{12}$ alkylcycloalkenyl;

(ii) aryl; substituted aryl; heteroaryl; or substituted heteroaryl;

(iii) heterocycloalkyl or substituted heterocycloalkyl; and (iv) hydrogen or deuterium;

G is selected from —OH, —NHS(O)$_2$—$R_3$, —NH(SO$_2$)NR$_4$R$_5$, and NR$_4$R$_5$; and R" is selected from hydrogen, methyl, ethyl, and allyl.

2. The compound of claim 1, wherein the compound is of Formula II:

(II)

or a pharmaceutically acceptable salt thereof, where $X_1$-$X_4$ are independently selected from —CR$_6$ and N, wherein each $R_6$ is independently selected from:

(i) hydrogen; halogen; —NO$_2$; —CN; or N$_3$;

(ii) -M-R$_3$, wherein M is O, S, NH;

(iii) NR$_4$R$_5$;

(iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$alkyl, substituted —$C_2$-$C_8$ alkenyl, or substituted —$C_2$-$C_8$alkynyl each containing 0, 1, 2, or 3 heteroatoms selected from O, S or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl;

(v) aryl; substituted aryl; heteroaryl; or substituted heteroaryl; and (vi) heterocycloalkyl or substituted heterocycloalkyl;

X', $L_1$, W, $L_2$, Ⓑ , $M_2$, A, R, R', R", $R_3$ $R_4$ $R_5$ and G are as defined in claim 1.

3. The compound of claim 1, wherein the compound is of Formula III or IV:

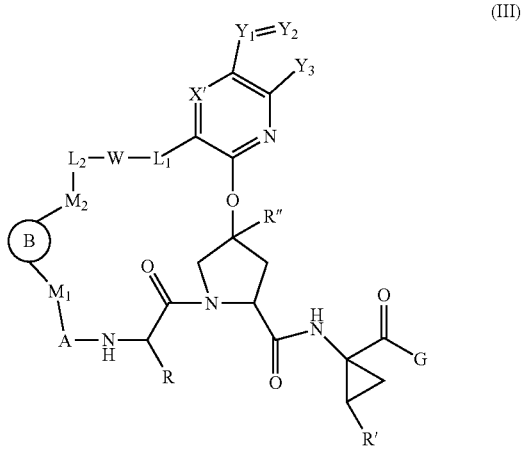

(III)

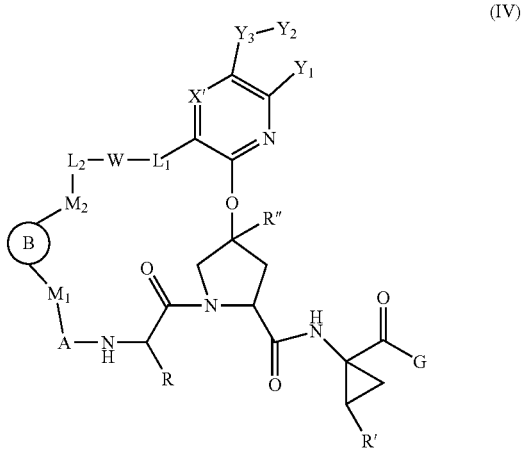

(IV)

or a pharmaceutically acceptable salt thereof, where each $Y_1$ and $Y_2$ are independently selected from CR$_6$, N, and each $Y_3$ is selected from NR$_6$, S and O;

each $R_6$ is independently selected from:
(i) hydrogen; halogen; $-NO_2$; $-CN$; or $N_3$;
(ii) -M-$R_3$, wherein M is O, S, or NH;
(iii) $NR_4R_5$;
(iv) $-C_1$-$C_8$ alkyl, $-C_2$-$C_8$ alkenyl, or $-C_2$-$C_8$ alkynyl each containing 0, 1, 2, or 3 heteroatoms selected from O, S, or N; substituted $-C_1$-$C_8$ alkyl, substituted $-C_2$-$C_8$ alkenyl, or substituted $-C_2$-$C_8$ alkynyl each containing 0, 1, 2, or 3 heteroatoms selected from O, S or N; $-C_3$-$C_{12}$ cycloalkyl, substituted $-C_3$-$C_{12}$ cycloalkyl; $-C_3$-$C_{12}$ cycloalkenyl, or substituted $-C_3$-$C_{12}$ cycloalkenyl;
(v) aryl; substituted aryl; heteroaryl; or substituted heteroaryl; and
(vi) heterocycloalkyl or substituted heterocycloalkyl;
X', $L_1$, W, $L_2$, $M_1$, ⓑ, $M_2$, A, R, R', R", $R_3$ $R_4$ $R_5$ and G are as defined in claim 1.

4. The compound of claim 1, wherein the compound is of Formula V:

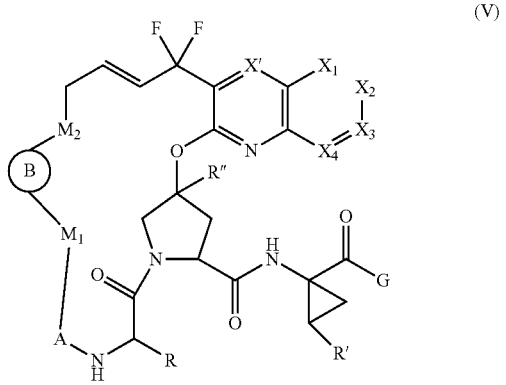

(V)

or a pharmaceutically acceptable salt thereof, wherein
$X_1$-$X_4$ are independently selected from $-CR_6$ and N, wherein each $R_6$ is independently selected from:
(i) hydrogen; halogen; $-NO_2$; $-CN$; or $N_3$;
(ii) -M-$R_3$, where M is O, S, or NH;
(iii) $NR_4R_5$;
(iv) $-C_1$-$C_8$ alkyl, $-C_2$-$C_8$ alkenyl, or $-C_2$-$C_8$ alkynyl each containing 0, 1, 2, or 3 heteroatoms selected from O, S, or N; substituted $-C_1$-$C_8$ alkyl, substituted $-C_2$-$C_8$ alkenyl, or substituted $-C_2$-$C_8$ alkynyl each containing 0, 1, 2, or 3 heteroatoms selected from O, S or N; $-C_3$-$C_{12}$ cycloalkyl, substituted $-C_3$-$C_{12}$ cycloalkyl; $-C_3$-$C_{12}$ cycloalkenyl, or substituted $-C_3$-$C_{12}$cycloalkenyl;
(v) aryl; substituted aryl; heteroaryl; or substituted heteroaryl; and
(vi) heterocycloalkyl or substituted heterocycloalkyl;
X', $L_1$, W, $L_2$, $M_1$, ⓑ, $M_2$, A, R, R', R", $R_3R_4$, $R_5$ and G are as defined in claim 1.

5. The compound of claim 1, wherein the compound is of Formula VI:

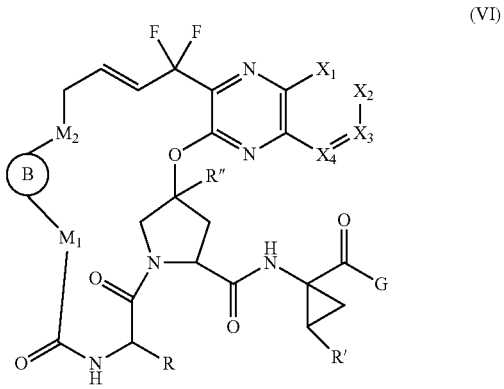

(VI)

or a pharmaceutically acceptable salt thereof, wherein
$X_1$-$X_4$ are independently selected from $-CR_6$ and N, wherein each $R_6$ is independently selected from:
(i) hydrogen; halogen; $-NO_2$; $-CN$; or $N_3$;
(ii) -M-$R_3$, wherein M is O, S, or NH;
(iii) $NR_4R_5$;
(iv) $-C_1$-$C_8$ alkyl, $-C_2$-$C_8$ alkenyl, or $-C_2$-$C_8$ alkynyl each containing 0, 1, 2, or 3 heteroatoms selected from O, S, or N; substituted $-C_1$-$C_8$ alkyl, substituted $-C_2$-$C_8$ alkenyl, or substituted $-C_2$-$C_8$ alkynyl each containing 0, 1, 2, or 3 heteroatoms selected from O, S or N; $-C_3$-$C_{12}$ cycloalkyl, substituted $-C_3$-$C_{12}$ cycloalkyl; $-C_3$-$C_{12}$ cycloalkenyl, or substituted $-C_3$-$C_{12}$ cycloalkenyl;
(v) aryl; substituted aryl; heteroaryl; or substituted heteroaryl; and
(vi) heterocycloalkyl or substituted heterocycloalkyl;
$L_1$, W, $L_2$, $M_1$, ⓑ, $M_2$, A, R, R', R", $R_3$, $R_4$, $R_5$ and G are as defined in claim 1.

6. The compound of claim 1, wherein the compound is of Formula VII:

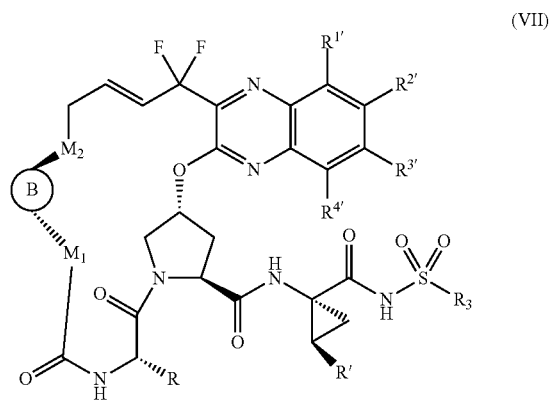

(VII)

or a pharmaceutically acceptable salt thereof, wherein
$R^{1'}$, $R^{2'}$, $R^{3'}$ and $R^{4'}$ are each independently $R_6$, or $R^{1'}$ and $R^{2'}$, $R^{2'}$ and $R^{3'}$, or $R^{3'}$ and $R^{4'}$ are taken together with the carbon atoms to which they are attached to form an aromatic or heteroaromatic or cyclic or heterocyclic ring;

each R$_6$ is independently selected from:
- (i) hydrogen; halogen; —NO$_2$; —CN; or N$_3$;
- (ii) -M-R$_3$, wherein M is O, S, or NH;
- (iii) NR$_4$R$_5$;
- (iv) —C$_1$-C$_8$ alkyl, —C$_2$-C$_8$ alkenyl, or —C$_2$-C$_8$ alkynyl each containing 0, 1, 2, or 3 heteroatoms selected from O, S, or N; substituted —C$_1$-C$_8$ alkyl, substituted —C$_2$-C$_8$ alkenyl, or substituted —C$_2$-C$_8$ alkynyl each containing 0, 1, 2, or 3 heteroatoms selected from O, S or N; —C$_3$-C$_{12}$ cycloalkyl, substituted —C$_3$-C$_{12}$ cycloalkyl; —C$_3$-C$_{12}$ cycloalkenyl, or substituted —C$_3$-C$_{12}$ cycloalkenyl;
- (v) aryl; substituted aryl; heteroaryl; or substituted heteroaryl; and
- (vi) heterocycloalkyl or substituted heterocycloalkyl;

L$_1$, W, L$_{2,M1}$, (B), M$_2$, A, R, R', R", R$_3$, R$_4$, R$_5$ and G are as defined in claim 1.

7. The compound of claim 6, wherein (a) R$^{1'}$, R$^{2'}$, R$^{3'}$ and R$^{4'}$ are hydrogen; (b) R$^{4'}$ and R$^{4'}$ are hydrogen; and one of R$^{2'}$ and R$^{3'}$ is hydrogen, and the other is selected from halo, methyl optionally substituted with one or more halo, or —O—methyl optionally substituted with one or more halo; or (c) R$^{1'}$ and R$^{2'}$, or R$^{2'}$ and R$^{3'}$, or R$^{3'}$ and R$^{4'}$, taken together with carbon atoms to which they are attached, form a 5- or 6-membered carbocycle or heterocycle, and the rest of R$^{1'}$, R$^{2'}$, R$^{3'}$ and R$^{4'}$ are hydrogen.

8. The compound of claim 6, wherein R$_3$ is

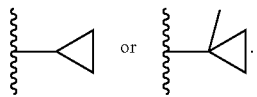

9. The compound of claim 6, wherein R' is

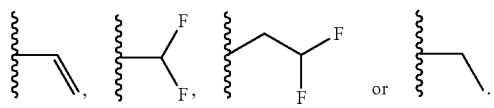

10. The compound of claim 6, wherein R is

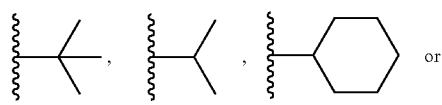

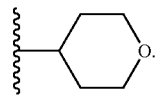

11. A pharmaceutical composition comprising the compound according to claim 1 or a pharmaceutically acceptable salt thereof, in combination with a pharmaceutically acceptable carrier or excipient.

12. A method of treating a hepatitis C viral infection in a subject, comprising administering to the subject a therapeutically effective amount of the pharmaceutical composition according to claim 11.

13. A method of inhibiting the replication of hepatitis C virus, the method comprising contacting the virus with a hepatitis C viral NS3 protease inhibitory amount of the compound of claim 1.

14. The method of claim 12, further comprising administering concurrently an additional anti-hepatitis C virus agent.

15. The compound of claim 1, represented by Formula XI, (XI)

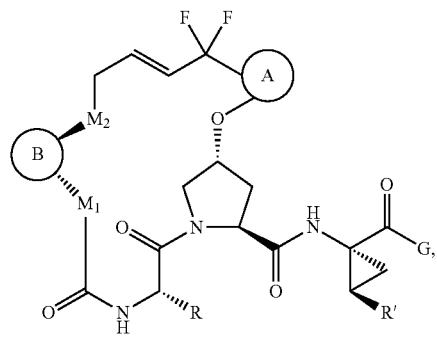

or a pharmaceutically acceptable salt thereof, wherein R,

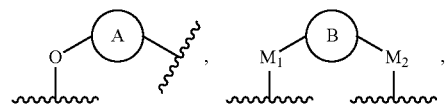

R' and G are delineated for each compound in the table below:

| Compound | R | M$_1$—(B)—M$_2$ | O—(A)—$\zeta$ | R' | G |
|---|---|---|---|---|---|
| 1. | *tert*-butyl | —O—CH(CH$_3$)—CH(CH$_3$)—O— | quinoxaline-O— | vinyl | —NH—S(O)$_2$—cyclopropyl |